US012589167B2

(12) United States Patent
Schmidt et al.

(10) Patent No.: US 12,589,167 B2
(45) Date of Patent: Mar. 31, 2026

(54) AAV GENE THERAPY VECTOR WITH PODOCYTE-SPECIFIC PROMOTER

(71) Applicants: The University of Bristol, Bristol (GB); SYNCONA IP HOLDCO (3) LIMITED, London (GB)

(72) Inventors: Dominic Schmidt, London (GB); Valeryia Kuzmuk, London (GB); Moin Saleem, Bristol (GB); Gavin Welsh, Bristol (GB)

(73) Assignees: The University of Bristol, Bristol (GB); Syncona IP Holdco (3) Limited, London (GB)

( * ) Notice: Subject to any disclaimer, the term of this patent is extended or adjusted under 35 U.S.C. 154(b) by 321 days.

(21) Appl. No.: 17/909,839

(22) PCT Filed: Mar. 12, 2021

(86) PCT No.: PCT/GB2021/050633
§ 371 (c)(1),
(2) Date: Sep. 7, 2022

(87) PCT Pub. No.: WO2021/181118
PCT Pub. Date: Sep. 16, 2021

(65) Prior Publication Data
US 2024/0197917 A1      Jun. 20, 2024

(30) Foreign Application Priority Data

Mar. 12, 2020     (GB) ..................................... 2003618

(51) Int. Cl.
*A61K 48/00*          (2006.01)
*C07K 14/78*          (2006.01)
*C12N 15/86*          (2006.01)
(52) U.S. Cl.
CPC .......... *A61K 48/0058* (2013.01); *C07K 14/78* (2013.01); *C12N 15/86* (2013.01); *C07K 2319/42* (2013.01); *C12N 2750/14143* (2013.01); *C12N 2750/14145* (2013.01); *C12N 2830/008* (2013.01); *C12N 2830/50* (2013.01)
(58) Field of Classification Search
None
See application file for complete search history.

(56) References Cited

U.S. PATENT DOCUMENTS

| | | | |
|---|---|---|---|
| 2006/0281090 A1 | 12/2006 | Lieber et al. | |
| 2010/0221317 A1 | 9/2010 | Reiser et al. | |
| 2010/0256057 A1 | 10/2010 | Kim et al. | |
| 2014/0087002 A1 | 3/2014 | Saaristo | |
| 2021/0380969 A1* | 12/2021 | Nonnenmacher .. | C12N 15/1058 |
| 2023/0175016 A1 | 6/2023 | Griffith et al. | |

FOREIGN PATENT DOCUMENTS

| | | | | |
|---|---|---|---|---|
| CA | 3079553 A1 | 4/2019 | | |
| CN | 107011424 A | 8/2017 | | |
| RU | 2675861 C1 | 12/2018 | | |
| WO | WO-98/17815 A1 | 4/1998 | | |
| WO | WO-2005/012351 A2 | 2/2005 | | |
| WO | WO-2006/088950 A2 | 8/2006 | | |
| WO | WO-2009/061448 A2 | 5/2009 | | |
| WO | WO-2012/019122 A2 | 2/2012 | | |
| WO | WO-2015/022447 A1 | 2/2015 | | |
| WO | WO-2016/014781 A1 | 1/2016 | | |
| WO | WO-2018071831 A1 * | 4/2018 | ................ | A61P 3/10 |
| WO | WO-2018/197873 A1 | 11/2018 | | |
| WO | WO-2018/220211 A1 | 12/2018 | | |
| WO | WO-2020/086735 A1 | 4/2020 | | |
| WO | WO-2020068261 A1 * | 4/2020 | ......... | C07K 14/4741 |
| WO | WO-2020/096492 A1 | 5/2020 | | |
| WO | WO-2020/148548 A1 | 7/2020 | | |
| WO | WO-2021/181118 A1 | 9/2021 | | |
| WO | WO-2022/003357 | 1/2022 | | |
| WO | WO-2022/189811 | 9/2022 | | |

OTHER PUBLICATIONS

Holthöfer, et al. Nephrin localizes at the podocyte filtration slit area and is characteristically spliced in the human kidney. American Journal of Pathology. Nov. 1999; 155(5):1681-87. (Year: 1999).*
Wang, et al. Adeno-associated virus vector as a platform for gene therapy delivery. Nature Reviews Drug Discovery. May 2019; 18:358-78. (Year: 2019).*
Tryggvason and Patrakka. Genetic Diseases of the Kidney. 2009. Academic Press. Chapter 4: Alport's Disease and thin basement membrane nephropathy; 77-96. (Year: 2009).*
U.S. Appl. No. 18/280,699, The University of Bristol et al.
Ausubel et al. Short Protocols in Molecular Biology, 4th edition, (1999) ibid, pp. 7-58 to 7-60.
Birke et al., AAV-mediated expression of human PRELP inhibits complement activation, choroidal neovascularization and deposition of membrane attack complex in mice, Gene Ther., 21(5):507-13 (2014).
Database accession No. EMB-0633771110, Adeno-Associated Virus Gene Therapy Prevents Progression of Kidney Disease in Genetic Human and Mouse Models of Nephrotic Syndrome, 2019.
Ding et al., Adeno-associated virus gene therapy prevents progression of kidney disease in genetic human and mouse models of nephrotic syndrome, Abstract: SA-OR057, Glomerular Diseases: Technologies, Mechanisms, and Therapeutics, Washington, DC (2019).
Ding et al., Investigating Adeno-Associated Virus as a Vector for Gene Therapy for Steroid-Resistant Nephrotic Syndrome, Doctoral Thesis, The University of Bristol, Nov. 28, 2019 [abstract\.
Eremina et al., VEGF inhibition and renal thrombotic microangiopathy, N Engl J Med., 358(11):1129-36 (2008).
Funk et al., Endothelial cell-specific collagen type IV-alpha3 expression does not rescue Alport syndrome in Col4alpha3–/– mice, Am. J Physiol. Renal Physiol., 316:830-837 (2019).

(Continued)

*Primary Examiner* — Allison M Fox
*Assistant Examiner* — Gina Pronzati
(74) *Attorney, Agent, or Firm* — MARSHALL, GERSTEIN & BORUN LLP

(57) ABSTRACT

A viral vector, wherein the viral vector comprises a COL4A3, COL4A4 or COL4A5 transgene.

28 Claims, 16 Drawing Sheets
Specification includes a Sequence Listing.

(56) References Cited

OTHER PUBLICATIONS

Guo et al., WT1 activates a glomerular-specific enhancer identified from the human nephrin gene, J. Am. Soc. Nephrol., 15911):2851-6 (2004).

International Application No. PCT/GB2021/051668, International Search Report and Written Opinion, mailed Oct. 15, 2021.

International Application No. PCT/GB2022/050649, International Search Report and Written Opinion, mailed Jun. 24, 2022.

Kajander et al., Dual interaction of factor H with C3d and glycosaminoglycans in host-nonhost discrimination by complement, Proc. Natl. Acad. Sci. USA, 108(7):2897-902 (2011).

Keir et al., Current evidence for the role of complement in the pathogenesis of Shiga toxin haemolytic uraemic syndrome, Pediatr. Nephrol., 29(10):1895-902 (2014).

Keir et al., VEGF regulates local inhibitory complement proteins in the eye and kidney, J. Clin. Invest., 127(1):199-214 (2017).

Lin et al., Feasibility of Repairing Glomerular Basement Membrane Defects in Alport Syndrome, J Am Soc Nephrol., 25:687-692 (2014).

Merle et al., Complement System Part I—Molecular Mechanisms of Activation and Regulation, Front. Immunol., 6:262 (2015).

Mühlig et al., Podocytes Produce and Secrete Functional Complement C3 and Complement Factor H, Front. Immunol., 11:1833 (2020).

Noris et al., Atypical hemolytic-uremic syndrome, N Engl. J. Med., 361(17):1676-87 (2009).

Ristola et al., Regulation of nephrin gene by the Ets transcription factor, GA-binding protein, Nephrol. Dial. Transplant., 28(4):846-55 (2013).

Ristola et al., Transcription of nephrin-Neph3 gene pair is synergistically activated by WT1 and NF-?B and silenced by DNA methylation, Nephrol. Dial. Transplant., 27(5):1737-45 (2012).

Saleem et al., A conditionally immortalized human podocyte cell line demonstrating nephrin and podocin expression, J. Am. Soc. Nephrol., 13(3):630-8 (2002).

Satchell et al., Conditionally immortalized human glomerular endothelial cells expressing fenestrations in response to VEGF, Kidney Int., 69(9):1633-40 (2006).

Willows et al., The role of complement in kidney disease, Clin. Med. (London), 20(2):156-60 (2020).

Ausubel et al., Current Protocols in Molecular Biology, Ch. 9, 13 and 16, John Wiley & Sons (1995 and periodic supplements).

Ayuso et al., Production, Purification and Characterization of Adeno-Associated Vectors, Curr. Gene Ther., 10(6):423-36 (2010).

Chiang et al., Endoplasmic reticulum stress signal impairs erythropoietin production: a role for ATF4, Am. J. Physiol. Cell Physiol., 304(4):C342-53 (2013).

Linkkeri et al., Structure of the Gene for Congenital Nephrotic Syndrome of the Finnish Type (NPHS1) and Characterization of Mutations, Am. J. Hum. Genet., 64(1):51-61 (1999).

Merten et al., Production of lentiviral vectors, Mol. Ther. Methods Clin. Dev., 3:16017 (2016).

Nadeau et al., Production of adenovirus vector for gene therapy, Biotechnol. Adv., 20(7-9):475-89 (2003).

NCBI Database accession No. NP_001014975.1, complement factor H isoform b precursor [*Homo sapiens*] (Dec. 4, 2023).

Perocheau et al., Age-Related Seroprevalence of Antibodies Against AAV-LK03 in a UK Population Cohort, Hum. Gene Ther., 30(1):79-87 (2019).

Piekarowicz et al., A Muscle Hybrid Promoter as a Novel Tool for Gene Therapy, Mol. Ther. Methods Clin. Dev., 15:157-69 (2019).

Ristola et al., Regulation of Neph3 gene in podocytes—key roles of transcription factors NF-?B and Sp1, BMC Mol. Biol., 10:83 (2009).

Rossant et al., Expression of a retinoic acid response element-hsplacZ transgene defines specific domains of transcriptional activity during mouse embryogenesis, Genes Dev., 5(8):1333-44 (1991).

Tabassum et al., Structural characterization and mutational assessment of podocin—A novel drug target to nephrotic syndrome—An in silico approach, Interdiscip. Sci., 6(1):32-9 (2014).

UniProtKB Database accession No. P05155 (Aug. 13, 1987).

UniProtKB Database accession No. P05156 (Aug. 13, 1987).

UniProtKB Database accession No. P08174 (Aug. 1, 1988).

UniProtKB Database accession No. P08603 (Aug. 1, 1988).

UniProtKB Database accession No. P10909 (Jul. 1, 1989).

UniProtKB Database accession No. P13987 (Jan. 1, 1990).

UniProtKB Database accession No. P15529 (Apr. 1, 1990).

UniProtKB Database accession No. P17927 (Nov. 1, 1990).

UniProtKB Database accession No. P20851 (Feb. 1, 1991).

UniProtKB Database accession No. Q96PZ7 (Nov. 28, 2003).

UniProtKB, Database accession No. Q01955 (Oct. 1, 1996).

Vaughn et al., How do mesangial and endothelial cells form the glomerular tuft?, J. Am. Soc. Nephrol., 19(1):24-33 (2008).

Akil, Dual and triple AAV delivery of large therapeutic gene sequences into the inner ear, Hear Res., 394:107912 (Sep. 2020).

Altschul et al., Basic Local Alignment Search Tool, J. Mol. Biol., 1990, p. 403-410.

Ausubel et al., Chapter 18: Bioinformatics, Short Protocols in Molecular Biology, Fourth Edition, John Wiley & Sons, Inc. (1999).

Devereux et al., A comprehensive set of sequence analysis programs for the VAX, Nucl. Acid Res., 12:387-395 (1984).

Ding et al., 241 Adeno-associated virus vector gene therapy ameliorates nephrosis in a podocin-deficient mouse model of nephrotic syndrome, UK Kidney Week (Jun. 2019).

Heikkilä et al., Adenovirus-mediated transfer of type IV collagen alpha5 chain cDNA into swine kidney in vivo: deposition of the protein into the glomerular basement membrane, Gene Ther., 8(11):882-90 (Jun. 2001).

International Search Report and Written Opinion, mailed Jun. 29, 2021, in International (PCT) Application No. PCT/GB2021/050633.

Kodippili et al., Dual AAV Gene Therapy for Duchenne Muscular Dystrophy with a 7-kb Mini-Dystrophin Gene in the Canine Model, Hum Gene Ther. Mar. 2018;29(3):299-311.

Lisowski et al., Selection and evaluation of clinically relevant AAV variants in a xenograft liver model, Nature, 2014, 506(7488), pp. 382-386.

Luo et al., Hepatorenal correction in murine glycogen storage disease type I with a double-stranded adeno-associated virus vector, Mol. Ther., 19:1961-70 (2011).

Madeira et al., The EMBL-EBI search and sequence analysis tools APIs in 2019, Nucleic acids research, 47(W1):W636-W641 (2019).

McClements et al., Adeno-associated Virus (AAV) Dual Vector Strategies for Gene Therapy Encoding Large Transgenes, Yale J Biol Med., 90(4):611-623 (2017).

Moeller et al., Two gene fragments that direct podocyte-specific expression in transgenic mice, J Am. Soc. Nephrol., 13:1561-7 (2002).

Ni et al., Podocyte culture: tricks of the trade, Nephrology, 2012, vol. 17(6), pp. 525-531.

Oleggini et al., Rare functional variants of podocin (NPHS2) promoter in patients with nephrotic syndrome, Gene Expression, 13(I):59-66 (2006).

Picconi et al., Kidney-specific expression of GFP by in-utero delivery of pseudotyped adeno-associated virus 9, Molecular Therapy Methods & Clinical Development, 1, 14014 (2014).

Rocca et al., rAAV9 combined with renal vein injection is optimal for kidney-targeted gene delivery: conclusion of a comparative study, Gene therapy, 21:618-628 (2014).

Rutledge et al., Infectious clones and vectors derived from adeno-associated virus (AAV) serotypes other than AAV type 2, 998. Journal of Virology, 1998, 72(1), pp. 309-319.

Schambach et al., Woodchuck hepatitis virus post-transcriptional regulatory element deleted from X protein and promoter sequences enhances retroviral vector titer and expression, Gene Therapy, 13, 641 (2005).

Schievenbusch et al., Combined Paracrine and Endocrine AAV9 mediated Expression of Hepatocyte Growth Factor for the Treatment of Renal Fibrosis, Molecular Therapy, 18:1302-1309 (2010).

Tatusova et al., BLAST 2 Sequences, a new tool for comparing protein and nucleotide sequences, FEMS Microbiol. Lett., vol. 174, No. 2, p. 247-250 (1999).

(56) References Cited

OTHER PUBLICATIONS

Tatusova et al., Erratum to BLAST 2 Sequences, a new tool for comparing protein and nucleotide sequences, FEMS Microbiol. Lett., vol. 177, No. 1, p. 187-188 (1999).

Trempe et al., Alternate mRNA splicing is required for synthesis of adeno-associated virus VP1 capsid protein, J. Virol., 62(9), pp. 3356-3363 (1988).

Wang et al., Efficient CFTR expression from AAV vectors packaged with promoters—the second generation, Gene Therapy, 6(4), pp. 667-675 (1999).

Wong et al., Identification and characterization of a glomerular-specific promoter from the human nephrin gene, Am. J. Physiol. Renal Physiol., 279(6):F1027-1032 (2000).

Badri et al., Optimization of radiation dosing schedules for proneural glioblastoma, J Math Biol., 72(5):1301-1336 (Apr. 2016).

Baylot et al., TCTP Has a Crucial Role in the Different Stages of Prostate Cancer Malignant Progression, Results Probl Cell Differ., 64:255-261 (2017).

Ding et al., Adeno-associated virus gene therapy prevents progression of kidney disease in genetic human and mouse models of nephrotic syndrome, Supplement for Kidney Week 2019; Journal of the American Society of Nephrology (Nov. 5, 2019).

Epifanova et al., Viral vectors for delivering genetic material into a cell and their use in neurobiology, Modern technologies in medicine, 9(1):162-174 (2017).

Favre et al., Critical aspects of viral vectors for gene transfer into the kidney, Journal of the American Society of Nephrology, 11:S149-153 (Nov. 2000).

Fraizer et al., Transcriptional Regulation of the Human Wilms' Tumor Gene (WT1), J. Biol. Chem., vol. 269(12) pp. 8892-8900 (Mar. 25, 1994).

GenBank Accession No. NM_004646, *Homo sapiens* NPHS1 adhension molecule, nephrin (NPHS1), mRNA, dated Apr. 30, 2025.

Heidet et al., Glomerular Expression of Type IV Collagen Chains in Normal and X-Linked Alport Syndrome Kidneys, Am J Pathol., 156(6):1901-1910 (Jun. 2000).

Java et al., Role of complement receptor 1 (CR1; CD35) on epithelial cells: A model for understanding complement-mediated damage in the kidney, Mol Immunology, 67(200) pp. 584-595 (Oct. 2015).

Loeb et al., Enhanced Expression of Transgenes from Adeno-Associated Virus Vectors with the Woodchuck Hepatitis Virus Posttranscriptional Regulatory Element: Implications for Gene Therapy, Human Gene Therapy, 10(14):2295-2305 (Sep. 1999).

Okazaki et al., Development of a model of early-onset IgA nephropathy, Journal of the American Society of Nephrology, 23(8):1364-1374 (Aug. 2012).

Plant et al., Detection of Mutations in COL4A5 in Patients With Alport Syndrome, Hum. Mutat., 13(2):124-132 (1999).

Russian Patent Application No. 2022124683, Search Report, dated Sep. 27, 2024.

Salvadori et al., Complement involvement in kidney disease: from physiopathology to therapeutical targeting, World Journal of Nephrology, vol. 4(2) pp. 169-184 (May 6, 2015).

Storey et al., COL4A3/COL4A4 mutations and features in individuals with autosomal recessive Alport syndrome, J Am Soc Nephrol., 24(12):1945-1954 (Dec. 2013).

Van der Ploeg et al., Pompe's disease, Lancet., 372(9646):1342-1353 (Oct. 2008).

Xia et al., FOXC2 Autoregulates Its Expression in the Pulmonary Endotherlium After Endotoxin Stimulation in a Histone Acetylation-Dependent Manner, Frontiers in Cell and Developmental Biology, vol. 9 article 657662 (May 4, 2021).

* cited by examiner

Cacctgaggtcaggagttcgagaccagcgtggccaacatgatgaaaccccgtctctagtaaaaatacaaaaat
tagccaggcatggtgctatatacctgtagcaccagctacttgggagacagaggtgggagaattacttgaacctg
ggaggttcaagccatgggaggtggaagttgcagtgagccgagatgccactgcactccagcctgagcaacaga
gcaagactatctcaagaaaagaaagaaagaaagaaagagacttgccaaggtcatgtatcagggcaaggaag
agctggggggcccagctggctgctcccctgctgagctgggagaccaccttgatctgacttctcccatcttcccagc
ctaagccaggccctggggtcacggaggctggggaggcaccgaggaacgcgcctggcatgtgctgacagggg
attttatgctccagctgggccagctgggaggagcctgctgggcagaggccagagctgggggctctggaaggta
cctggggggaggttgcactgtgagaatgagctcaagctgggtcagagagcagggctgactctgccagtgcctgc
atcagcctcatcgctctcctaggctcctggcctgctggactctgggctgcaggtccttcttgaaaggctgtgagta
gtgagacaaggagcaggagtgaggggtggcaggagagaagatagagattgagagagagagagagagag
acagagagagaggaagagacagagacaaaaggagagagaacggcttagacaaggagagaaagatggaaa
gataaagagactgggcgcagtggctcacgcctgtaatcccaacacttggggaggccaaggtgggaggatggc
ttgaaggaaagagtctgagatcaacctggccaacatagtgagaccccgtctctaaaaaaaaaagaaaaaaa
aaagaaaaagaaaaaaaagtttttttaaagagacagagaaagagactcagagattgagactgagagcaag
acagagagagatactcacagggaagaggggaagaggaaaacgagaaagggaggagagtaacggaaagag
ataaaaaagaaaagcaggtggcagagacacacagagagggacccagagaaagccagacagacgcaggtg
gctggcagcgggcgctgtgggggtcacagtaggggggacctgtg

FIG. 1

Figures 2, 3:
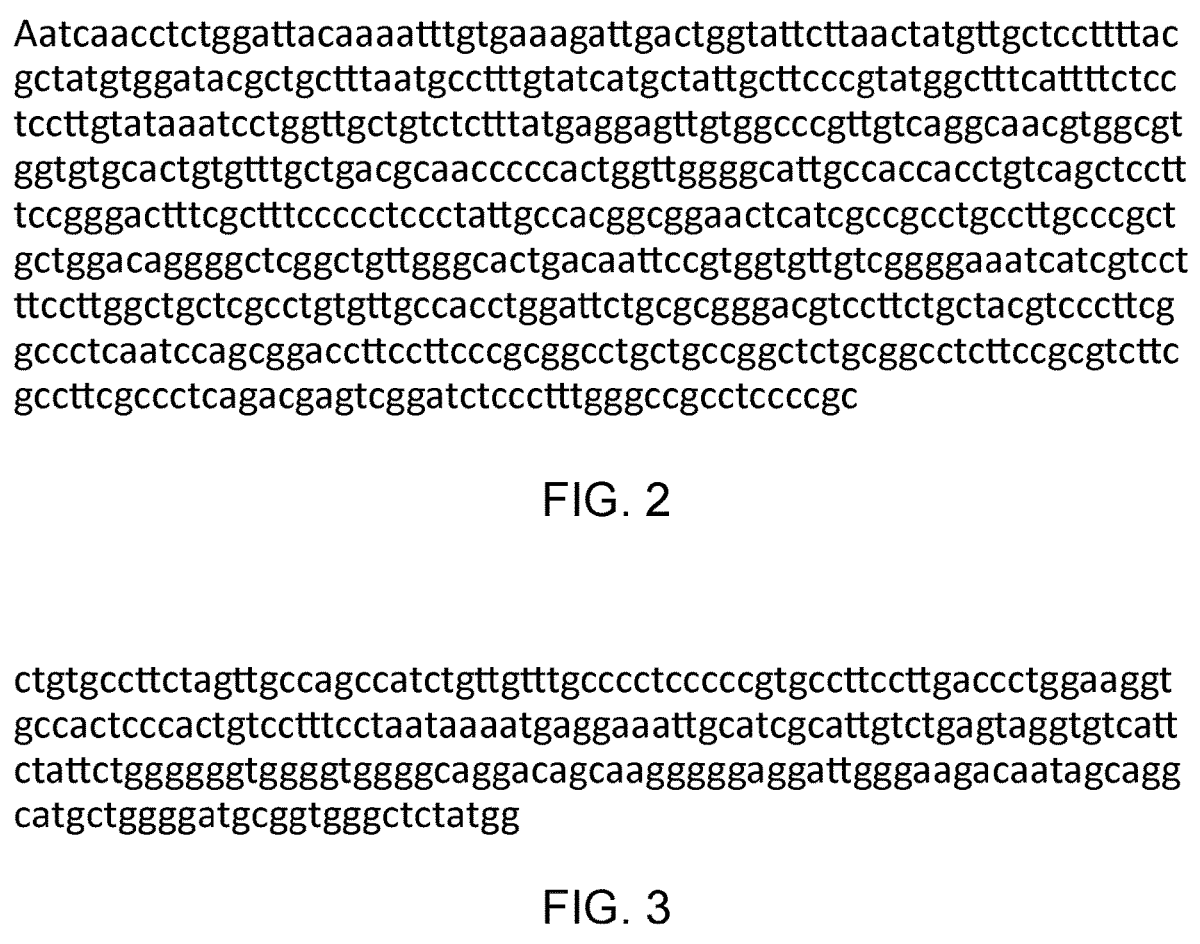

Aatcaacctctggattacaaaatttgtgaaagattgactggtattcttaactatgttgctccttttac
gctatgtggatacgctgctttaatgcctttgtatcatgctattgcttcccgtatggctttcattttctcc
tccttgtataaatcctggttgctgtctctttatgaggagttgtggcccgttgtcaggcaacgtggcgt
ggtgtgcactgtgtttgctgacgcaaccccccactggttggggcattgccaccacctgtcagctcctt
tccgggactttcgctttccccctccctattgccacggcggaactcatcgccgcctgccttgcccgct
gctggacaggggctcggctgttgggcactgacaattccgtggtgttgtcggggaaatcatcgtcct
ttccttggctgctcgcctgtgttgccacctggattctgcgcgggacgtccttctgctacgtcccttcg
gccctcaatccagcggaccttccttcccgcggcctgctgccggctctgcggcctcttccgcgtcttc
gccttcgccctcagacgagtcggatctccctttgggccgcctccccgc

FIG. 2 ctgtgccttctagttgccagccatctgttgtttgcccctcccccgtgccttccttgaccctggaaggt
gccactcccactgtcctttcctaataaaatgaggaaattgcatcgcattgtctgagtaggtgtcatt
ctattctggggggtggggtggggcaggacagcaaggggggaggattgggaagacaatagcagg
catgctggggatgcggtgggctctatgg

D
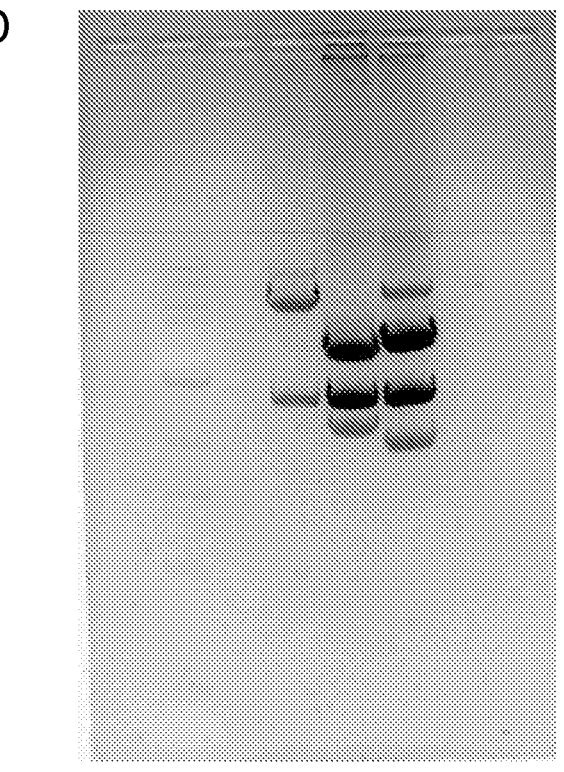
E
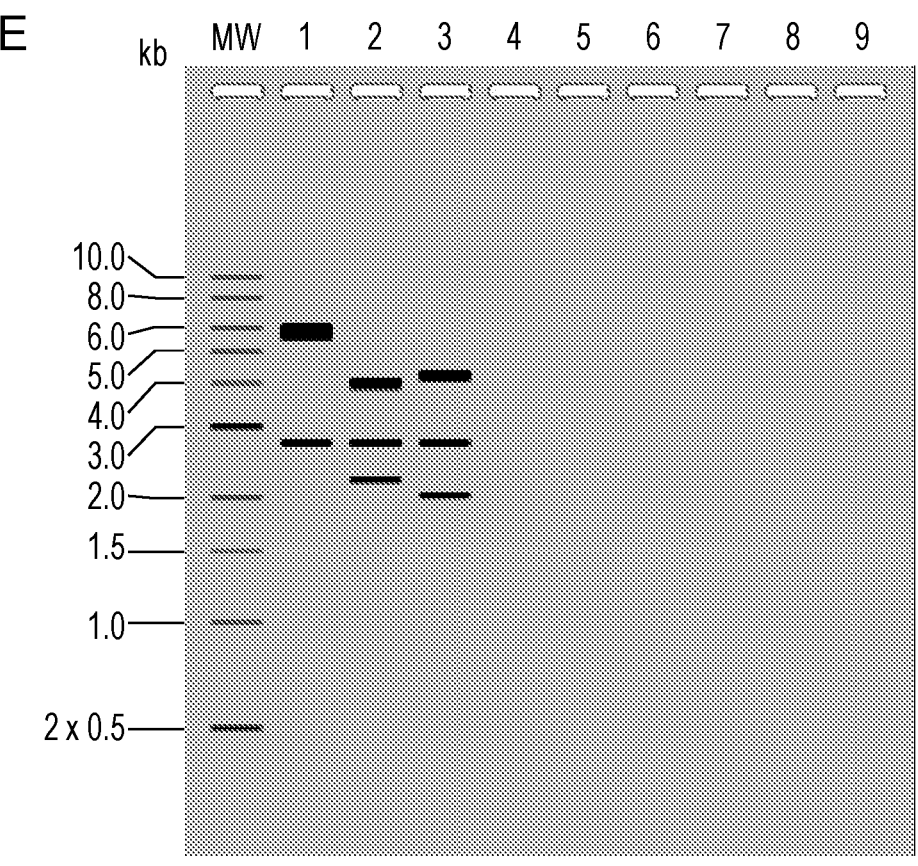
0.8% agarose
FIG. 4 (Continued)

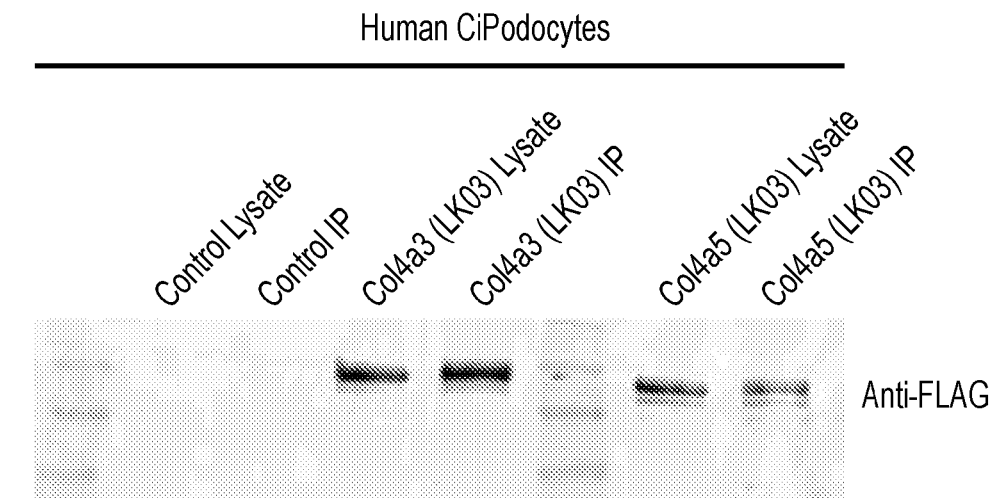
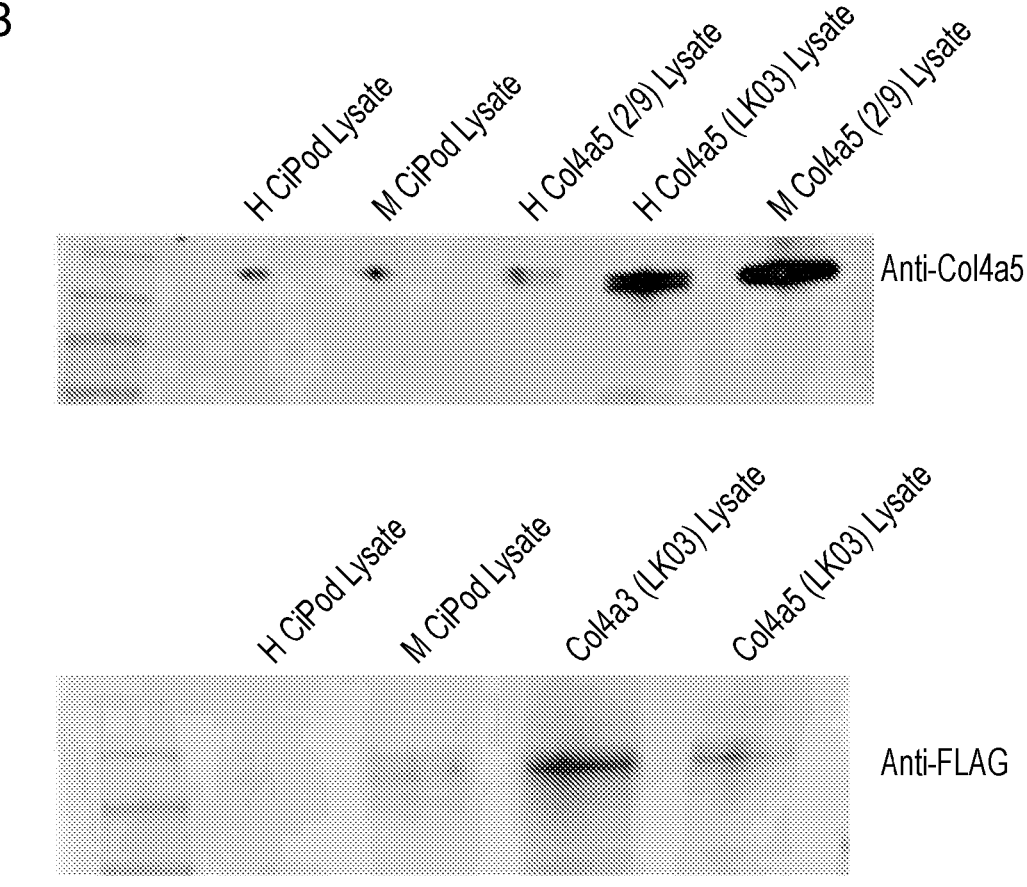
FIG. 5

C

Human CiPod Control    Human CiPod+Col4a5 AAV

Minimal Nephrin Promoter (hNPHS1)
A 1252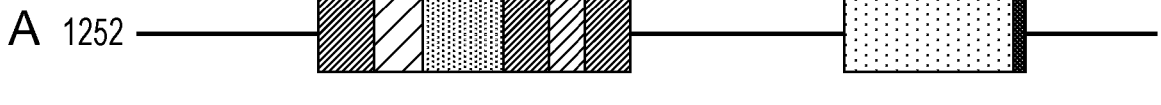
B 822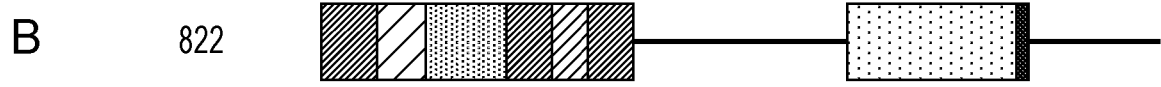
C 268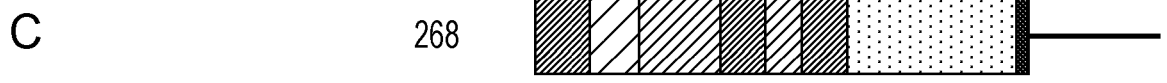
D
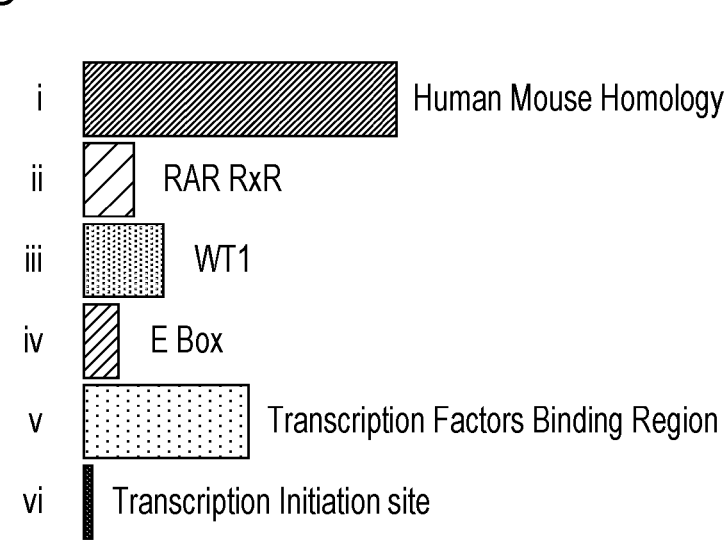
i — Human Mouse Homology
ii — RAR RxR
iii — WT1
iv — E Box
v — Transcription Factors Binding Region
vi — Transcription Initiation site
FIG. 6

A pACE_hNPHS1prom (NeBuilder)
3991 bp

Tn7R

GmR

Pc promoter loxP

To remove part 1

WT1

E Box

To remove part 2

'ITR hNPHS1 promoter ori

Tn7L

SV40 poly (A) signal

Transcription factors binding region

500

1000

1500

2000

2500

3000

3500

(2102) ClaI (2496..2511)ClaI_Lenti_hNPHS1_For (2548..2572)TF_EBox_Rev (3127..3154)Transcription_factor_For (3294..3314)BamH1_Lenti_hNPHS1_Rev (3349) BamHI

B pLenti_hNPHS1_GFP BLAST VAL
8530 bp

A pACE_hNPHS1prom (NeBuilder) (val primers)
3991 bp (2102) ClaI (2496..2511)Cla1_Lenti_hNPHS1_For
(2548..2572)TF_EBox_Rev (3127..3154)Transcription_factor_For
(3294..3314)BamH1_Lenti_hNPHS1_Rev
(3349) BamHI

B

A
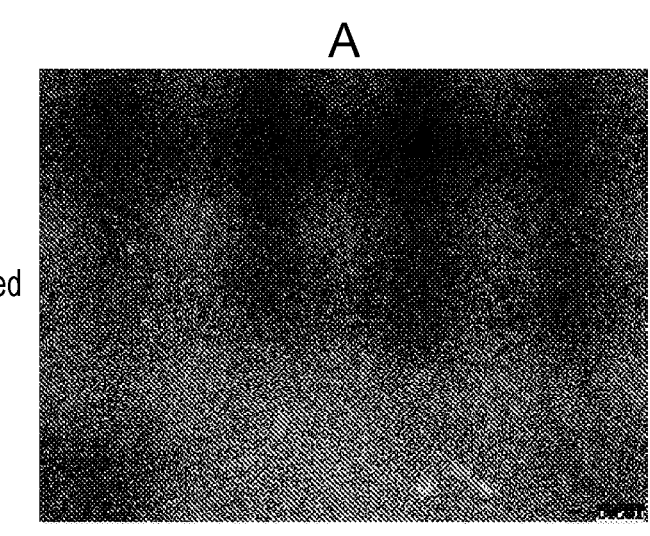
Untransduced
B
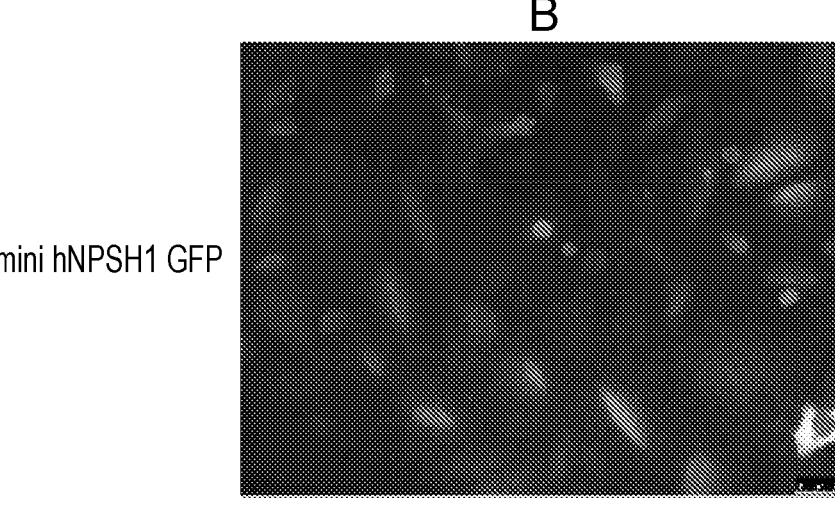
mini hNPSH1 GFP
C
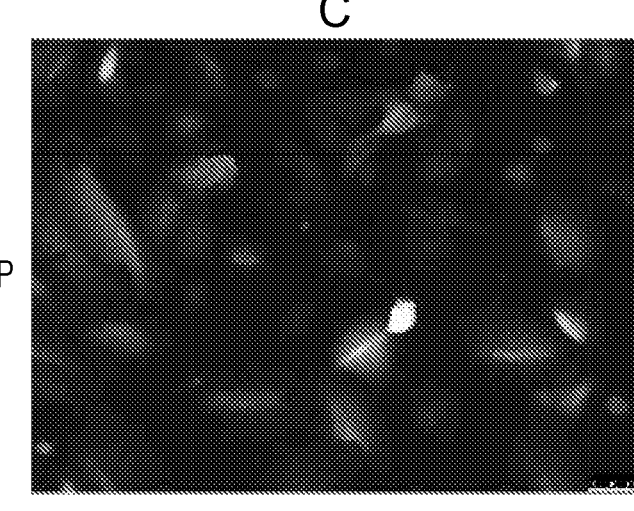
FL hNPSH1 GFP
FIG. 9

AAV GENE THERAPY VECTOR WITH PODOCYTE-SPECIFIC PROMOTER

CROSS-REFERENCES TO RELATED APPLICATIONS

This application is a U.S. national phase of International (PCT) Application No. PCT/GB2021/050633, filed on 12 Mar. 2021, which claims priority benefit of Application No. 2003618.2, filed on Mar. 12, 2020, in the United Kingdom.

INCORPORATION BY REFERENCE OF MATERIAL SUBMITTED ELECTRONICALLY

Incorporated by reference in its entirety is a computer-readable sequence listing identified as follows: 100,343 byte text file named "58023_Seqlisting.txt"; created on Jun. 23, 2021.

FIELD OF INVENTION

The present invention relates to viral vector comprising a COL4A3, COL4A4 or COL4A5 transgene and kidney specific promoters, as well as use of the viral vectors in treating Alport syndrome.

BACKGROUND TO THE INVENTION

Alport syndrome (AS) is a genetic condition affecting approximately 1 in 5,000-10,000 of all individuals in continental Europe and the USA. AS is also known as familial nephritis, hereditary nephritis, thin basement membrane disease and thin basement membrane nephropathy. The condition usually presents during childhood and is associated with a spectrum of phenotypes that include a progressive loss of kidney function, and can also include hearing loss and eye abnormalities.

AS is caused by pathogenic variants in the COL4A3, COL4A4 and COL4A5 genes, which result in abnormalities of the collagen IV α345 network of basement membranes. The condition can be transmitted in an X-linked, autosomal dominant, or autosomal recessive pattern, with X-linked being the common while autosomal recessive and autosomal dominant account for around 15% and 20% of cases respectively.

In the absence of treatment, renal disease progresses from microhematuria to proteinuria, progressive renal insufficiency and end-stage renal disease in all males with the X-linked form, and in all males and females with the autosomal recessive form.

AS can be diagnosed by genetic testing and current treatments include angiotensin converting enzyme (ACE) inhibitors or angiotensin receptor blockers (ARB) to delay onset of end-stage kidney disease. However, at present there is no way to prevent end-stage renal failure, with a renal transplant being the only option.

There are significant challenges to overcome in developing a successful gene therapy for AS. The first is that the COL4A5, COL4A3 and COL4A4 proteins are 1685, 1670 and 1690 amino acids each, rendering them challenging for transport by an adeno-associated virus (AAV) vector, due to limited AAV cargo capacity. The second significant challenge is to successfully deliver the gene therapy to podocyte cells in the glomerulus of the kidney, which produce collagen IV in the glomerular basement membrane.

The present invention aims to provide a novel gene therapy vector that can efficiently deliver a COL4A3, COL4A4 or COL4A5 transgene to podocytes and thereby provide a therapy for the treatment of Alport syndrome.

SUMMARY OF THE INVENTION

The present invention provides a viral vector, wherein the viral vector comprises a COL4A3, COL4A4 or COL4A5 transgene. The viral vector can be used to target podocytes within the glomerulus of the kidney in order to treat Alport syndrome.

Without being bound by theory, the present inventors believe that podocytes offer a highly tractable target for gene therapy approaches in kidney disease and that by targeting COL4A3, COL4A4 or COL4A5 to podocytes the collagen IV α345 network of the glomerular basement membrane can be changed and at least partially normalised.

In one aspect, present invention provides a viral vector, wherein the viral vector comprises a COL4A3, COL4A4 or COL4A5 transgene.

The COL4A3 transgene may encode a COL4A3 polypeptide which comprises or consists of the polypeptide sequence having at least 70% identity to SEQ ID NO: 1, or a fragment thereof; the COL4A4 transgene may encode a COL4A4 polypeptide which comprises or consists of the polypeptide sequence having at least 70% identity to SEQ ID NO: 2, or a fragment thereof; and/or the COL4A5 transgene may encode a COL4A5 polypeptide which comprises or consists of the polypeptide sequence having at least 70% identity to SEQ ID NO: 3, or a fragment thereof. In some embodiments, the COL4A3 transgene encodes a full-length COL4A3 polypeptide, the COL4A4 transgene encodes a full-length COL4A4 polypeptide; and/or the COL4A5 transgene encodes a full-length COL4A5 polypeptide. Suitably, the COL4A3, COL4A4 or COL4A5 transgene is human and/or comprises a hemagglutinin (HA) tag.

Preferably, the viral vector comprises a podocyte-specific promoter. Suitably, the podocyte-specific promoter is minimal nephrin promoter NPHS1 or podocin promoter NPHS2. In some embodiments, the podocyte-specific promoter is minimal nephrin promoter NPHS1.

The present inventors have developed a minimal nephrin promoter which is shorter than known minimal nephrin promoters and surprisingly capable of driving transgene expression in podocytes. The promoter also surprisingly retains podocyte-specificity. Such a minimal nephrin promoter can be used to minimise the cargo size and aid packaging of full length COL4A3, COL4A4 or COL4A5. Accordingly, the minimal nephrin promoter NPHS1 may comprise or consist of the nucleotide sequence shown as SEQ ID NO: 10, or a variant which is at least 70% identical to SEQ ID NO: 10.

Suitably, the viral vector is an adeno-associated virus (AAV). Suitably, the AAV vector is in the form of an AAV vector particle. In some embodiments, the AAV vector particle is a podocyte-specific AAV vector. In some embodiments, the AAV vector is AAV serotype 2/9, LK03 or 3B.

In some embodiments, the COL4A3, COL4A4 or COL4A5 transgene is a mini-gene.

In some embodiments, the viral vector additionally comprises a Woodchuck hepatitis post-transcriptional regulatory element (WPRE). In some embodiments, the viral vector does not comprise Woodchuck hepatitis post-transcriptional regulatory element (WPRE).

In some embodiments, the viral vector additionally comprises a Kozak sequence between the promoter and the COL4A3, COL4A4 or COL4A5 transgene.

Suitably, the viral vector additionally comprises a polyadenylation signal such as bovine growth hormone (bGH) polyadenylation signal or an early SV40 polyadenylation signal. In some embodiments, the polyadenylation signal is an early SV40 polyadenylation signal.

In one aspect, the present invention provides a viral vector gene therapy, wherein the viral vector comprises a COL4A3, COL4A4 or COL4A5 transgene.

In preferred embodiments, the viral vector is a viral vector according to the present invention.

In one aspect, the present invention provides a viral vector gene therapy, wherein the gene therapy comprises:

a first viral vector comprising at least a portion of a COL4A3, COL4A4 or COL4A5 transgene; and a second viral vector comprising at least a portion of a corresponding COL4A3, COL4A4 or COL4A5 transgene.

In preferred embodiments, the first viral vector is a viral vector according to the present invention, and/or the second viral vector is a viral vector according to the present invention.

In one aspect, the present invention provides a viral vector or viral vector gene therapy according to the present invention, for use in treating or preventing Alport Syndrome.

Suitably, the viral vector or viral vector gene therapy is administered to a human patient. In some embodiments, the viral vector or viral vector gene therapy is administered systemically. In some embodiments, the viral vector or viral vector gene therapy is administered by intravenous injection. In some embodiments, the viral vector or viral vector gene therapy is administered by injection into the renal artery.

Viral Vectors

Adeno-Associated Viral (AAV) Vectors

The viral vector may be an adeno-associated virus (AAV) and suitable AAV vector serotypes include 2/9, LK03 and 3B.

The viral vector may be in the form of an AAV vector particle.

The AAV vector particle may be encapsidated by capsid proteins. The serotype may facilitate the transduction of podocytes, for example specific transduction of podocytes. Preferably, the AAV vector particle is a podocyte-specific vector particle. The AAV vector particle may be encapsidated by a podocyte-specific capsid. The AAV vector particle may comprise a podocyte-specific capsid protein. Targeted transduction to the podocytes should remove the impact of liver tropism, following systemic application.

Suitably, the AAV vector particles may be transcapsidated forms wherein an AAV genome or derivative having an ITR of one serotype is packaged in the capsid of a different serotype. The AAV vector particle also includes mosaic forms wherein a mixture of unmodified capsid proteins from two or more different serotypes makes up the viral capsid. The AAV vector particle also includes chemically modified forms bearing ligands adsorbed to the capsid surface. For example, such ligands may include antibodies for targeting a particular cell surface receptor.

Where a derivative comprises capsid proteins i.e. VP1, VP2 and/or VP3, the derivative may be a chimeric, shuffled or capsid-modified derivative of one or more naturally occurring AAVs. In particular, the invention encompasses the provision of capsid protein sequences from different serotypes, clades, clones, or isolates of AAV within the same vector (i.e. a pseudotyped vector). The AAV vector may be in the form of a pseudotyped AAV vector particle.

Chimeric, shuffled or capsid-modified derivatives will be typically selected to provide one or more desired functionalities for the AAV vector. Thus, these derivatives may display increased efficiency of gene delivery, decreased immunogenicity (humoral or cellular), an altered tropism range and/or improved targeting of podocytes compared to an AAV vector comprising a naturally occurring AAV genome. Increased efficiency of gene delivery may be effected by improved receptor or co-receptor binding at the cell surface, improved internalisation, improved trafficking within the cell and into the nucleus, improved uncoating of the viral particle and improved conversion of a single-stranded genome to double-stranded form. Increased efficiency may also relate to an altered tropism range or targeting of podocytes, such that the vector dose is not diluted by administration to tissues where it is not needed.

Chimeric capsid proteins include those generated by recombination between two or more capsid coding sequences of naturally occurring AAV serotypes. This may be performed for example by a marker rescue approach in which non-infectious capsid sequences of one serotype are co-transfected with capsid sequences of a different serotype, and directed selection is used to select for capsid sequences having desired properties. The capsid sequences of the different serotypes can be altered by homologous recombination within the cell to produce novel chimeric capsid proteins.

Chimeric capsid proteins also include those generated by engineering of capsid protein sequences to transfer specific capsid protein domains, surface loops or specific amino acid residues between two or more capsid proteins, for example between two or more capsid proteins of different serotypes.

Shuffled or chimeric capsid proteins may also be generated by DNA shuffling or by error-prone PCR. Hybrid AAV capsid genes can be created by randomly fragmenting the sequences of related AAV genes e.g. those encoding capsid proteins of multiple different serotypes and then subsequently reassembling the fragments in a self-priming polymerase reaction, which may also cause crossovers in regions of sequence homology. A library of hybrid AAV genes created in this way by shuffling the capsid genes of several serotypes can be screened to identify viral clones having a desired functionality. Similarly, error prone PCR may be used to randomly mutate AAV capsid genes to create a diverse library of variants which may then be selected for a desired property.

The sequences of the capsid genes may also be genetically modified to introduce specific deletions, substitutions or insertions with respect to the native wild-type sequence. In particular, capsid genes may be modified by the insertion of a sequence of an unrelated protein or peptide within an open reading frame of a capsid coding sequence, or at the N- and/or C-terminus of a capsid coding sequence. The unrelated protein or peptide may advantageously be one which acts as a ligand for a particular cell type, thereby conferring improved binding to a target cell or improving the specificity of targeting of the vector to a particular cell population. The unrelated protein may also be one which assists purification of the viral particle as part of the production process, i.e. an epitope or affinity tag. The site of insertion will typically be selected so as not to interfere with other functions of the viral particle e.g. internalisation, trafficking of the viral particle.

The capsid protein may be an artificial or mutant capsid protein. The term "artificial capsid" as used herein means Suitably, the AAV vector particle may be encapsidated by AAV9 VP1, VP2, and VP3 capsid proteins.

Suitably, the AAV9 VP1 capsid protein may comprise or consist of the amino acid sequence shown as SEQ ID NO: 31, or a variant which is at least 90% identical to SEQ ID NO: 31.

```
Exemplary AAV9 VP1 capsid protein (SEQ ID NO: 31):
MAADGYLPDWLEDNLSEGIREWWALKPGAPQPKANQQHQDNARGLVLPGYKYLGPGNGLDKGEPVNAAD

AAALEHDKAYDQQLKAGDNPYLKYNHADAEFQERLKEDTSFGGNLGRAVFQAKKRLLEPLGLVEEAAKT

APGKKRPVEQSPQEPDSSAGIGKSGAQPAKKRLNFGQTGDTESVPDPQPIGEPPAAPSGVGSLTMASGG

GAPVADNNEGADGVGSSSGNWHCDSQWLGDRVITTSTRTWALPTYNNHLYKQISNSTSGGSSNDNAYFG

YSTPWGYFDFNRFHCHFSPRDWQRLINNNWGFRPKRLNFKLFNIQVKEVTDNNGVKTIANNLTSTVQVF

TDSDYQLPYVLGSAHEGCLPPFPADVFMIPQYGYLTLNDGSQAVGRSSFYCLEYFPSQMLRTGNNFQFS

YEFENVPFHSSYAHSQSLDRLMNPLIDQYLYYLSKTINGSGQNQQTLKFSVAGPSNMAVQGRNYIPGPS

YRQQRVSTTVTQNNNSEFAWPGASSWALNGRNSLMNPGPAMASHKEGEDRFFPLSGSLIFGKQGTGRDN

VDADKVMITNEEEIKTTNPVATESYGQVATNHQSAQAQAQTGWVQNQGILPGMVWQDRDVYLQGPIWAK

IPHTDGNFHPSPLMGGFGMKHPPPQILIKNTPVPADPPTAFNKDKLNSFITQYSTGQVSVEIEWELQKE

NSKRWNPEIQYTSNYYKSNNVEFAVNTEGVYSEPRPIGTRYLTRNL
``` that the capsid particle comprises an amino acid sequence which does not occur in nature or which comprises an amino acid sequence which has been engineered (e.g. modified) from a naturally occurring capsid amino acid sequence. In other words the artificial capsid protein comprises a mutation or a variation in the amino acid sequence compared to the sequence of the parent capsid from which it is derived where the artificial capsid amino acid sequence and the parent capsid amino acid sequences are aligned.

The capsid protein may comprise a mutation or modification relative to the wild type capsid protein which improves the ability to transduce podocytes relative to an unmodified or wild type viral particle. Improved ability to transduce podocytes may be measured for example by measuring the expression of a transgene, e.g. GFP, carried by the AAV vector particle, wherein expression of the transgene in podocytes correlates with the ability of the AAV vector particle to transduce podocytes.

AAV9 Serotype

The AAV 2/9 serotype has shown significant tropism for newborn and adult mouse kidney, localising to the glomeruli and tubules (Luo et al., 2011; Picconi et al., 2014; Schievenbusch et al., 2010), and AAV2/9 vector combined with renal vein injection has been shown to be suitable for kidney-targeted gene delivery (Rocca et al., 2014). AAV 2/9 is therefore one suitable vector for use in the viral vector of the present invention.

The AAV vector particle may comprise an AAV9 capsid protein. Suitably, the AAV vector particle may be encapsidated by AAV9 capsid proteins.

The AAV vector particle may comprise an AAV9 VP1 capsid protein, an AAV9 VP2 capsid protein, and/or an AAV9 VP3 capsid protein. Suitably, the AAV vector particle may be encapsidated by AAV9 VP1 capsid proteins, AAV9 VP2 capsid proteins, and/or AAV9 VP3 capsid proteins.

Suitably, the variant may be at least 95%, at least 96%, at least 97%, at least 98% or at least 99% identical to SEQ ID NO: 31.

Suitably, the AAV9 VP2 and VP3 capsid proteins may be N-terminal truncations of SEQ ID NO: 31, or N-terminal truncations of a variant which is at least 90% identical, at least 95%, at least 96%, at least 97%, at least 98% or at least 99% identical to SEQ ID NO: 31.

AAV LK03 Serotype

Synthetic AAV capsids such as LK03 can also be suitable vectors for use in the viral vector of the present invention. This vector has been shown to transduce human primary hepatocytes at high efficiency in vitro and in vivo. However, until now it has not been utilised in kidney-targeted gene delivery. Surprisingly, AAV-LK03 vectors can achieve high transduction of close to 100% in human podocytes in vitro and can be used to transduce podocytes specifically in vitro (see PCT/GB2020/050097).

The AAV-LK03 cap sequence consists of fragments from seven different wild-type serotypes (AAV1, 2, 3B, 4, 6, 8, 9) and is described in Lisowski, L., et al., 2014. Nature, 506(7488), pp. 382-386, although AAV-3B represents 97.7% of the cap gene sequence and 98.9% of the amino acid sequence.

The AAV vector particle may comprise an LK03 capsid protein. Suitably, the AAV vector particle may be encapsidated by LK03 capsid proteins.

The AAV vector particle may comprise an LK03 VP1 capsid protein, an LK03 VP2 capsid protein, and/or an LK03 VP3 capsid protein. Suitably, the AAV vector particle may be encapsidated by LK03 VP1 capsid proteins, LK03 VP2 capsid proteins, and/or LK03 VP3 capsid proteins. Suitably, the AAV vector particle may be encapsidated by LK03 VP1, VP2, and VP3 capsid proteins.

Suitably, the LK03 VP1 capsid protein may comprise or consist of the amino acid sequence shown as SEQ ID NO: 32, or a variant which is at least 90% identical to SEQ ID NO: 32.

Exemplary LK03 VP1 capsid protein (SEQ ID NO: 32):
MAADGYLPDWLEDNLSEGIREWWALQPGAPKPKANQQHQDNARGLVLPGYKYLGPGNGLDKGEPVNAAD

AAALEHDKAYDQQLKAGDNPYLKYNHADAEFQERLKEDTSFGGNLGRAVFQAKKRLLEPLGLVEEAAKT

APGKKRPVDQSPQEPDSSSGVGKSGKQPARKRLNFGQTGDSESVPDPQPLGEPPAAPTSLGSNTMASGG

GAPMADNNEGADGVGNSSGNWHCDSQWLGDRVITTSTRTWALPTYNNHLYKQISSQSGASNDNHYFGYS

TPWGYFDFNRFHCHFSPRDWQRLINNNWGFRPKKLSFKLFNIQVKEVTQNDGTTTIANNLTSTVQVFTD

SEYQLPYVLGSAHQGCLPPFPADVEMVPQYGYLTLNNGSQAVGRSSFYCLEYFPSQMLRTGNNFQFSYT

FEDVPFHSSYAHSQSLDRLMNPLIDQYLYYLNRTQGTTSGTTNQSRLLFSQAGPQSMSLQARNWLPGPC

YRQQRLSKTANDNNNSNFPWTAASKYHLNGRDSLVNPGPAMASHKDDEEKFFPMHGNLIFGKEGTTASN

AELDNVMITDEEEIRTTNPVATEQYGTVANNLQSSNTAPTTRTVNDQGALPGMVWQDRDVYLQGPIWAK

IPHTDGHFHPSPLMGGFGLKHPPPQIMIKNTPVPANPPTTFSPAKFASFITQYSTGQVSVEIEWELQKE

NSKRWNPEIQYTSNYNKSVNVDFTVDTNGVYSEPRPIGTRYLTRPL

Suitably, the variant may be at least 95%, at least 96%, at least 97%, at least 98% or at least 99% identical to SEQ ID NO: 32.

Suitably, the LK03 VP2 and VP3 capsid proteins may be N-terminal truncations of SEQ ID NO: 32, or N-terminal truncations of a variant which is at least 90% identical, at least 95%, at least 96%, at least 97%, at least 98% or at least 99% identical to SEQ ID NO: 32.

AAV3B Serotype

AAV-3B is also known for its human hepatocyte tropism and is another a suitable vector for use in the viral vector of the present invention. To date it has not been utilised in kidney-targeted gene delivery.

The AAV vector particle may comprise an AAV3B capsid protein. Suitably, the AAV vector particle may be encapsidated by AAV3B capsid proteins.

Two distinct AAV3 isolates (AAV3A and AAV3B) have been cloned. In comparison with vectors based on other AAV serotypes, it is thought that AAV3 vectors inefficiently transduce most cell types. However, AAV3B may efficiently transduce podocytes. AA3B has been described in Rutledge, E. A., et al., 1998. Journal of virology, 72(1), pp. 309-319.

The AAV vector particle may comprise an AAV3B VP1 capsid protein, an AAV3B VP2 capsid protein, and/or an AAV3B VP3 capsid protein. Suitably, the AAV vector particle may be encapsidated by AAV3B VP1 capsid proteins, AAV3B VP2 capsid proteins, and/or AAV3B VP3 capsid proteins. Suitably, the AAV vector particle may be encapsidated by AAV3B VP1, VP2, and VP3 capsid proteins.

Suitably, the AAV3B VP1 capsid protein may comprise or consist of the amino acid sequence shown as SEQ ID NO: 33, or a variant which is at least 90% identical to SEQ ID NO: 33.

Exemplary AAV3B VP1 capsid protein (SEQ ID NO: 33):
MAADGYLPDWLEDNLSEGIREWWALKPGVPQPKANQQHQDNRRGLVLPGYKYLGPGNGLDKGEPVNEAD

AAALEHDKAYDQQLKAGDNPYLKYNHADAEFQERLQEDTSFGGNLGRAVFQAKKRILEPLGLVEEAAKT

APGKKRPVDQSPQEPDSSSGVGKSGKQPARKRLNFGQTGDSESVPDPQPLGEPPAAPTSLGSNTMASGG

GAPMADNNEGADGVGNSSGNWHCDSQWLGDRVITTSTRTWALPTYNNHLYKQISSQSGASNDNHYFGYS

TPWGYFDFNRFHCHFSPRDWQRLINNNWGFRPKKLSFKLFNIQVKEVTQNDGTTTIANNLTSTVQVFTD

SEYQLPYVLGSAHQGCLPPFPADVEMVPQYGYLTLNNGSQAVGRSSFYCLEYFPSQMLRTGNNFQFSYT

FEDVPFHSSYAHSQSLDRLMNPLIDQYLYYLNRTQGTTSGTTNQSRLLFSQAGPQSMSLQARNWLPGPC

YRQQRLSKTANDNNNSNFPWTAASKYHLNGRDSLVNPGPAMASHKDDEEKFFPMHGNLIFGKEGTTASN

AELDNVMITDEEEIRTTNPVATEQYGTVANNLQSSNTAPTTRTVNDQGALPGMVWQDRDVYLQGPIWAK

IPHTDGHFHPSPLMGGFGLKHPPPQIMIKNTPVPANPPTTFSPAKFASFITQYSTGQVSVEIEWELQKE

NSKRWNPEIQYTSNYNKSVNVDFTVDINGVYSEPRPIGTRYLTRN

Suitably, the variant may be at least 95%, at least 96%, at least 97%, at least 98% or at least 99% identical to SEQ ID NO: 33.

Suitably, the AAV3B VP2 and VP3 capsid proteins may be N-terminal truncations of SEQ ID NO: 33, or N-terminal truncations of a variant which is at least 90% identical, at least 95%, at least 96%, at least 97%, at least 98% or at least 99% identical to SEQ ID NO: 33.

AAV Genome

The AAV vector or AAV vector particle may comprise an AAV genome or a fragment or derivative thereof.

An AAV genome is a polynucleotide sequence, which may encode functions needed for production of an AAV particle. These functions include those operating in the replication and packaging cycle of AAV in a host cell, including encapsidation of the AAV genome into an AAV particle. Naturally occurring AAVs are replication-deficient and rely on the provision of helper functions in trans for completion of a replication and packaging cycle. Accordingly, the AAV genome used in the present invention is typically replication-deficient.

The AAV genome may be in single-stranded form, either positive or negative-sense, or alternatively in double-stranded form. The use of a double-stranded form allows bypass of the DNA replication step in the target cell and so can accelerate transgene expression. The maximum packaging capacity of the single-stranded form is larger than the double-stranded form. Suitably, the AAV genome is in single-stranded form.

AAVs occurring in nature may be classified according to various biological systems. The AAV genome may be from any naturally derived serotype, isolate or clade of AAV.

AAV may be referred to in terms of their serotype. A serotype corresponds to a variant subspecies of AAV which, owing to its profile of expression of capsid surface antigens, has a distinctive reactivity which can be used to distinguish it from other variant subspecies. Typically, an AAV vector particle having a particular AAV serotype does not efficiently cross-react with neutralising antibodies specific for any other AAV serotype. AAV serotypes include AAV1, AAV2, AAV3, AAV4, AAV5, AAV6, AAV7, AAV8, AAV9, AAV10 and AAV11. In some embodiments, the AAV vector of the invention may be an AAV3B, LK03, AAV9, or AAV8 serotype.

AAV may also be referred to in terms of clades or clones. This refers to the phylogenetic relationship of naturally derived AAVs, and typically to a phylogenetic group of AAVs which can be traced back to a common ancestor, and includes all descendants thereof. Additionally, AAVs may be referred to in terms of a specific isolate, i.e. a genetic isolate of a specific AAV found in nature. The term genetic isolate describes a population of AAVs which has undergone limited genetic mixing with other naturally occurring AAVs, thereby defining a recognisably distinct population at a genetic level.

Typically, the AAV genome of a naturally derived serotype, isolate or clade of AAV comprises at least one inverted terminal repeat sequence (ITR). An ITR sequence acts in cis to provide a functional origin of replication and allows for integration and excision of the vector from the genome of a cell. ITRs may be the only sequences required in cis next to the therapeutic gene.

The AAV genome may also comprise packaging genes, such as rep and/or cap genes which encode packaging functions for an AAV particle. A promoter may be operably linked to each of the packaging genes. Specific examples of such promoters include the p5, p19 and p40 promoters. For example, the p5 and p19 promoters are generally used to express the rep gene, while the p40 promoter is generally used to express the cap gene. The rep gene encodes one or more of the proteins Rep78, Rep68, Rep52 and Rep40 or variants thereof. The cap gene encodes one or more capsid proteins such as VP1, VP2 and VP3 or variants thereof. These proteins make up the capsid of an AAV particle, which determines the AAV serotype. VP1, VP2, and VP3 may be produced by alternate mRNA splicing (Trempe, J. P. and Carter, B. J., 1988. Journal of virology, 62(9), pp. 3356-3363). Thus, VP1, VP2 and VP3 may have identical sequences, but wherein VP2 is truncated at the N-terminus relative to VP1, and VP3 is truncated at the N-terminus relative to VP2.

The AAV genome may be the full genome of a naturally occurring AAV. For example, a vector comprising a full AAV genome may be used to prepare an AAV vector or vector particle.

Preferably, the AAV genome is derivatised for the purpose of administration to patients. Such derivatisation is standard in the art and the invention encompasses the use of any known derivative of an AAV genome, and derivatives which could be generated by applying techniques known in the art. The AAV genome may be a derivative of any naturally occurring AAV. Suitably, the AAV genome is a derivative of AAV1, AAV2, AAV3, AAV4, AAV5, AAV6, AAV7, AAV8, AAV9, AAV10, or AAV11. Suitably, the AAV genome is a derivative of AAV2.

Derivatives of an AAV genome include any truncated or modified forms of an AAV genome which allow for expression of a transgene from an AAV vector of the invention in vivo. Typically, it is possible to truncate the AAV genome significantly to include minimal viral sequence yet retain the above function. This is preferred for safety reasons to reduce the risk of recombination of the vector with wild-type virus, and also to avoid triggering a cellular immune response by the presence of viral gene proteins in the target cell.

The following portions could therefore be removed in a derivative of the invention: one inverted terminal repeat (ITR) sequence, the replication (rep) and capsid (cap) genes. However, derivatives may additionally include one or more rep and/or cap genes or other viral sequences of an AAV genome. Naturally occurring AAV integrates with a high frequency at a specific site on human chromosome 19, and shows a negligible frequency of random integration, such that retention of an integrative capacity in the AAV vector may be tolerated in a therapeutic setting.

The invention additionally encompasses the provision of sequences of an AAV genome in a different order and configuration to that of a native AAV genome. The invention also encompasses the replacement of one or more AAV sequences or genes with sequences from another virus or with chimeric genes composed of sequences from more than one virus. Such chimeric genes may be composed of sequences from two or more related viral proteins of different viral species.

Mini-Gene Approach

At almost 1700 amino acids, COL4A3, COL4A4 and COL4A5 are challenging to package into an AAV vector in their full length form due to AAV packaging constraints. However, the present inventors have developed a minimal nephrin promoter which is shorter than known minimal nephrin promoters and surprisingly capable of driving transgene expression in podocytes. Such a minimal nephrin promoter can be used to minimise the cargo size and aid packaging of full length COL4A3, COL4A4 or COL4A5.

One alternative option to packaging full length COL4A3, COL4A4 or COL4A5 may be to provide the COL4A3, COL4A4 or COL4A5 transgene as a mini-gene. The mini-gene approach has been successfully employed in the development of gene therapies for the treatment of Duchenne's muscular dystrophy (Kodippili et al 2018). In this approach the transgene is truncated so as to fit the vector, without losing the activity of the protein encoded by the transgene.

COL4A3, COL4A4 and COL4A5 proteins are approximately 170-185 kDa homologous polypeptides containing collagenous Gly-X-Y repeat sequences frequently interrupted by non-collagenous sequences and forming a triple helix repeat. Each polypeptide also contains a large globular non-collagenous domain at the carboxyl-terminal end. Approximately 200-300 amino acids should be removed from each of the COL4A3, COL4A4 and COL4A5 poly-peptides to produce a truncated transgene suitable for a mini-gene approach. The amino acids may be removed from the triple helix repeat. Preferably the amino acids are not removed from the non-collagenous region.

A COL4A5 mini-gene with an N-terminal HA tag or N-terminal MyC tag may be ligated into AAV2/9, AAVLK03 and AAVL3 vectors containing a human minimal nephrin promoter (NPHS2).

Viral Vector Gene Therapy

The present invention provides a viral vector gene therapy, wherein the viral vector comprises a COL4A3, COL4A4 or COL4A5 transgene.

The viral vector used in the viral vector gene therapy may be any viral vector of the present invention described herein. Accordingly, it will be understood that when a viral vector is referred to herein, this may also refer to a viral vector gene therapy unless context dictates otherwise.

Dual Vector Approach

An alternative option for the viral vector gene therapy may be to use a dual vector approach. In this approach, the viral vector gene therapy comprises a first viral vector comprising at least a portion of a COL4A3, COL4A4 or COL4A5 transgene; and an optional a podocyte-specific promoter; and a second viral vector comprising at least a portion of a corresponding COL4A3, COL4A4 or COL4A5 transgene; and an optional a podocyte-specific promoter. In other words, the transgene is divided into two separate sequences, each of which can be incorporated into a viral vector gene therapy as described herein. AAV dual vector approaches are described in. e.g., McClements and Maclaren 2017, incorporated herein by reference. The transgene sequences used in the dual vector approach may have overlapping exonic or intronic sequences, which when trans-duced will combine through, e.g., homologous recombina-tion, to reform a single transgene sequence. Alternatively, the two sequences may not overlap and will instead be combined by, e.g., an intein protein trans-splicing approach. It is also possible to incorporate in one of the two vectors a splice donor signal and in the second vector a splice acceptor signal that allow after ITR mediated head-to-tail concate-merisation trans-splicing resulting in a mature mRNA. It is further possible to combine these approaches into various hybrid approaches that, e.g., combines recombination with trans-splicing.

The first viral vector may be a viral vector according to the present invention as described herein, and/or the second viral vector may be a viral vector according to the present invention as described herein. In preferred embodiments, the first viral vector and the second viral vector are both viral vectors according to the present invention as described herein.

COL4A3, COL4A4 and COL4A5 Transgenes

The COL4A3, COL4A4 or COL4A5 transgene may com-prise an intron or intronic sequences, which can be used to improve gene expression. An intron or intronic sequences may be used in either the mini-gene or dual vector approach. In the dual vector approach this can allow for recombination of the first and second portions of the transgene via homolo-gous sequences of an intron. This is particularly useful when the dual vector approach is combined with a splice donor and acceptor method as using an exonic sequence would lead to part of the protein being spliced out, which is usually not desirable.

The COL4A3, COL4A4 or COL4A5 transgene may encode a COL4A3, COL4A4 or COL4A5 polypeptide, or a fragment or derivative thereof.

The COL4A3, COL4A4 or COL4A5 polypeptide or a fragment or derivative thereof may be capable of forming a collagen IV α345 network. Suitably, the fragment has about 200-300 amino acids removed.

In some embodiments, the COL4A3, COL4A4 or COL4A5 polypeptide is a full-length polypeptide.

Preferably, the COL4A3, COL4A4 or COL4A5 polypep-tide is human. An example human COL4A3 is the COL4A3 having the UniProtKB accession number Q01955. An example human COL4A4 is the COL4A3 having the Uni-ProtKB accession number P53420. An example human COL4A5 is the COL4A5 having the UniProtKB accession number P29400.

Suitably, the COL4A3 peptide may comprise or consist of the polypeptide sequence shown as SEQ ID NO: 1, or a variant which is at least 70% identical to SEQ ID NO: 1. Suitably, the variant may be at least 75%, at least 80%, at least 85%, at least 90%, at least 95%, at least 98%, at least 99% identical to SEQ ID NO: 1.

Suitably, the COL4A4 peptide may comprise or consist of the polypeptide sequence shown as SEQ ID NO: 2, or a variant which is at least 70% identical to SEQ ID NO: 2. Suitably, the variant may be at least 75%, at least 80%, at least 85%, at least 90%, at least 95%, at least 98%, at least 99% identical to SEQ ID NO: 2.

Suitably, the COL4A5 peptide may comprise or consist of the polypeptide sequence shown as SEQ ID NO: 3, or a variant which is at least 70% identical to SEQ ID NO: 3. Suitably, the variant may be at least 75%, at least 80%, at least 85%, at least 90%, at least 95%, at least 98%, at least 99% identical to SEQ ID NO: 3.

```
Exemplary COL4A3 amino acid sequence
                                      (SEQ ID NO: 1)
MSARTAPRPQVLLLPLLLVLLAAAPAASKGCVCKDKGQCFCDGAK

GEKGEKGFPGPPGSPGQKGFTGPEGLPGPQGPKGFPGLPGLTGSK

GVRGISGLPGFSGSPGLPGTPGNTGPYGLVGVPGCSGSKGEQGFP

GLPGTLGYPGIPGAAGLKGQKGAPAKEEDIELDAKGDPGLPGAPG

PQGLPGPPGFPGPVGPPGPPGFFGFPGAMGPRGPKGHMGERVIGH

KGERGVKGLTGPPGPPGTVIVTLTGPDNRTDLKGEKGDKGAMGEP

GPPGPSGLPGESYGSEKGAPGDPGLQGKPGKDGVPGFPGSEGVKG

NRGFPGLMGEDGIKGQKGDIGPPGFRGPTEYYDTYQEKGDEGTPG

PPGPRGARGPQGPSGPPGVPGSPGSSRPGLRGAPGWPGLKGSKGE

RGRPGKDAMGTPGSPGCAGSPGLPGSPGPPGPPGPGDIVERKGPPGD

HGLPGYLGSPGIPGVDGPKGEPGLLCTQCPYIPGPPGLPGLPGLH

GVKGIPGRQGAAGLKGSPGSPGNTGLPGFPGFPGAQGDPGLKGEK

GETLQPEGQVGVPGDPGLRGQPGRKGLDGIPGTPGVKGLPGPKGE

LALSGEKGDQGPPGDPGSPGSPGPAGPAGPPGYGPQGEPGLQGTQ

GVPGAPGPPGEAGPRGELSVSTPVPGPPGPPGPPGHPGPQGPPGI

PGSLGKCGDPGLPGPDGEPGIPGIGFPGPPGPKGDQGFPGTKGSL

GCPGKMGEPGLPGKPGLPGAKGEPAVAMPGGPGTPGFPGERGNSG

EHGEIGLPGLPGLPGTPGNEGLDGPRGDPGQPGPPGEQGPPGRCI

EGPRGAQGLPGLNGLKGQQGRRGKTGPKGDPGIPGLDRSGFPGET

GSPGIPGHQGEMGPLGQRGYPGNPGILGPPGEDGVIGMMGFPGAI
```

-continued

GPPGPPGNPGTPGQRGSPGIPGVKGQRGTPGAKGEQGDKGNPGPS

EISHVIGDKGEPGLKGFAGNPGEKGNRGVPGMPGLKGLKGLPGPA

GPPGPRGDLGSTGNPGEPGLRGIPGSMGNMGMPGSKGKRGTLGFP

GRAGRPGLPGIHGLQGDKGEPGYSEGTRPGPPGPTGDPGLPGDMG

KKGEMGQPGPPGHLGPAGPEGAPGSPGSPGLPGKPGPHGDLGFKG

IKGLLGPPGIRGPPGLPGFPGSPGPMGIRGDQGRDGIPGPAGEKG

ETGLLRAPPGPRGNPGAQGAKGDRGAPGFPGLPGRKGAMGDAGPR

GPTGIEGFPGPPGLPGAIIPGQTGNRGPPGSRGSPGAPGPPGPPG

SHVIGIKGDKGSMGHPGPKGPPGTAGDMGPPGRLGAPGTPGLPGP

RGDPGFQGFPGVKGEKGNPGFLGSIGPPGPIGPKGPPGVRGDPGT

LKIISLPGSPGPPGTPGEPGMQGEPGPPGPPGNLGPCGPRGKPGK

DGKPGTPGPAGEKGNKGSKGEPGPAGSDGLPGLKGKRGDSGSPAT

WTTRGFVFTRHSQTTAIPSCPEGTVPLYSGFSFLFVQGNQRAHGQ

DLGTLGSCLQRFTTMPFLFCNVNDVCNFASRNDYSYWLSTPALMP

MNMAPITGRALEPYISRCTVCEGPAIAIAVHSQTTDIPPCPHGWI

SLWKGFSFIMFTSAGSEGTGQALASPGSCLEEFRASPFLECHGRG

TCNYYSNSYSFWLASLNPERMERKPIPSTVKAGELEKIISRCQVC

MKKRH

Exemplary COL4A4 amino acid sequence (SEQ ID NO: 2)

MWSLHIVLMRCSFRLTKSLATGPWSLILILFSVQYVYGSGKKYIG

PCGGRDCSVCHCVPEKGSRGPPGPPGPQGPIGPLGAPGPIGLSGE

KGMRGDRGPPGAAGDKGDKGPTGVPGFPGLDGIPGHPGPPGPRGK

PGMSGHNGSRGDPGFPGGRGALGPGGPLGHPGEKGEKGNSVFILG

AVKGIQGDRGDPGLPGLPGSWGAGGPAGPTGYPGEPGLVGPPGQP

GRPGLKGNPGVGVKGQMGDPGEVGQQGSPGPTLLVEPPDFCLYKG

EKGIKGIPGMVGLPGPPGRKGESGIGAKGEKGIPGFPGPRGDPGS

YGSPGFPGLKGELGLVGDPGLFGLIGPKGDPGNRGHPGPPGVLVT

PPLPLKGPPGDPGFPGRYGETGDVGPPGPPGLLGRPGEACAGMIG

PPGPQGFPGLPGLPGEAGIPGRPDSAPGKPGKPGSPGLPGAPGLQ

GLPGSSVIYCSVGNPGPQGIKGKVGPPGGRGPKGEKGNEGLCACE

PGPMGPPGPPGLPGRQGSKGDLGLPGWLGTKGDPGPPGAEGPPGL

PGKHGASGPPGNKGAKGDMVVSRVKGHKGERGPDGPPGFPGQPGS

HGRDGHAGEKGDPGPPGDHEDATPGGKGFPGPLGPPGKAGPVGPP

GLGFPGPPGERGHPGVPGHPGVRGPDGLKGQKGDTISCNVTYPGR

HGPPGEDGPPGPKGFPGPGQGAPGLSGSDGHKGRPGTPGTAEIPGP

PGFRGDMGDPGFGGEKGSSPVGPPGPPGSPGVNGQKGIPGDPAFG

HLGPPGKRGLSGVPGIKGPRGDPGCPGAEGPAGIPGFLGLKGPKG

REGHAGFPGVPGPPGHSCERGAPGIPGQPGLPGYPGSPGAPGGKG

QPGDVGPPGPAGMKGLPGLPGRPGAHGPPGLPGIPGPFGDDGLPG

PPGPKGPRGLPGFPGFPGERGKPGAEGCPGAKGEPGEKGMSGLPG

-continued

DRGLRGAKGAIGPPGDEGEMAIISQKGTPGEPGPPGDDGFPGERG

DKGTPGMQGRRGEPGRYGPPGFHRGEPGEKGQPGPPGPPGPPGST

GLRGFIGFPGLPGDQGEPGSPGPPGFSGIDGARGPKGNKGDPASH

FGPPGPKGEPGSPGCPGHFGASGEQGLPGIQGPRGSPGRPGPPGS

SGPPGCPGDHGMPGLRGQPGEMGDPGPRGLQGDPGIPGPPGIKGP

SGSPGLNGLHGLKGQKGTKGASGLHDVGPPGPVGIPGLKGERGDP

GSPGISPPGPRGKKGPPGPPGSSGPPGPAGATGRAPKDIPDPGPP

GDQGPPGPDGPRGAPGPPGLPGSVDLLRGEPGDCGLPGPPGPPGP

PGPPGYKGFPGCDGKDGQKGPVGFPGPQGPHGFPGPPGEKGLPGP

PGRKGPTGLPGPRGEPGPPADVDDCPRIPGLPGAPGMRGPEGAMG

LPGMRGPSGPGCKGEPGLDGRRGVDGVPGSPGPPGRKGDTGEDGY

PGGPGPPGPIGDPGPKGFGPGYLGGFLLVLHSQTDQEPTCPLGMP

RLWTGYSLLYLEGQEKAHNQDLGLAGSCLPVESTLPFAYCNIHQV

CHYAQRNDRSYWLASAAPLPMMPLSEEAIRPYVSRCAVCEAPAQA

VAVHSQDQSIPPCPQTWRSLWIGYSFLMHTGAGDQGGGQALMSPG

SCLEDFRAAPFLECQGRQGTCHFFANKYSFWLTTVKADLQFSSAP

APDTLKESQAQRQKISRCQVCVKYS

Exemplary COL4A5 amino acid sequence (SEQ ID NO: 3)

MKLRGVSLAAGLFLLALSLWGQPAEAAACYGCSPGSKCDCSGIKG

EKGERGFPGLEGHPGLPGFPGPEGPPGPRGQKGDDGIPGPPGPKG

IRGPPGLPGFPGTPGLPGMPGHDGAPGPQGIPGCNGTKGERGFPG

SPGFPGLQGPPGPPGIPGMKGEPGSIIMSSLPGPKGNPGYPGPPG

IQGLPGPTGIPGPIGPPGPPGLMGPPGPPGLPGPKGNMGLNFQGP

KGEKGEQGLQGPPGPPGQISEQKRPIDVEFQKGDQGLPGDRGPPG

PPGIRGPPGPPGGEKGEKGEQGEPGKRGKPGKDGENGQPGIPGLP

GDPGYPGEPGRDGEKGQKGDTGPPGPPGLVIPRPGTGITIGEKGN

IGLPGLPGEKGERGFPGIQGPPGLPGPPGAAVMGPPGPPGFPGER

GQKGDEGPPGISIPGPPGLDGQPGAPGLPGPPGPAGPHIPPSDEI

CEPGPPGPPGSPGDKGLQGEQGVKGDKGDTCENCIGTGISGPPGQ

PGLPGLPGPPGSLGFPGQKGEKGQAGATGPKGLPGIPGAPGAPGF

PGSKGEPGDILTFPGMKGDKGELGSPGAPGLPGLPGTPGQDGLPG

LPGPKGEPGGITFKGERGPPGNPGLPGLPGNIGPMGPPGFGPPGP

VGEKGIQGVAGNPGQPGIPGPKGDPGQTITQPGKPGLPGNPGRDG

DVGLPGDPGLPGQPGLPGIPGSKGEPGIPGIGLPGPPGPKGFPGI

PGPPGAPGTPGRIGLEGPPGPPGFPGPKGEPGFALPGPPGPPGLP

GFKGALGPKGDRGFPGPPGPPGRTGLDGLPGPKGDVGPNGQPGPM

GPPGLPGIGVQGPPGPPGIPGPIGQPGLHGIPGEKGDPGPPGLDV

PGPPGERGSPGIPGAPGPIGPPGSPGLPGKAGASGFPGTKGEMGM

MGPPGPPGPLGIPGRSGVPGLKGDDGLQGQPGLPGPTGEKGSKGE

PGLPGPPGPMDPNLLGSKGEKGEPGLPGIPGVSGPKGYQGLPGDP

GQPGLSGQPGLPGPPGPKGNPGLPGQPGLIGPPGLKGTIGDMGFP

-continued

```
GPQGVEGPPGPSGVPGQPGSPGLPGQKGDKGDPGISSIGLPGLPG

PKGEPGLPGYPGNPGIKGSVGDPGLPGLPGTPGAKGQPGLPGFPG

TPGPPGPKGISGPPGNPGLPGEPGPVGGGGHPGQPGPPGEKGKPG

QDGIPGPAGQKGEPGQPGFGNPGPPGLPGLSGQKGDGGLPGIPGN

PGLPGPKGEPGFHGFPGVQGPPGPPGSPGPALEGPKGNPGPQGPP

GRPGLPGPEGPPGLPGNGGIKGEKGNPGQPGLPGLPGLKGDQGPP

GLQGNPGRPGLNGMKGDPGLPGVPGFPGMKGPSGVPGSAGPEGEP

GLIGPPGPPGPGLPGPSGQSIIIKGDAGPPGIPGQPGLKGLPGPQGP

QGLPGPTGPPGDPGRNGLPGFDGAGGRKGDPGLPGQPGTRGLDGP

PGPDGLQGPPGPPGTSSVAHGFLITRHSQTTDAPQCPQGTLQVYE

GFSLLYVQGNKRAHGQDLGTAGSCLRRESTMPFMFCNINNVCNFA

SRNDYSYWLSTPEPMPMSMQPLKGQSIQPFISRCAVCEAPAVVIA

VHSQTIQIPHCPQGWDSLWIGYSFMMHTSAGAEGSGQALASPGSC

LEEFRSAPFIECHGRGTCNYYANSYSFWLATVDVSDMFSKPQSET

LKAGDLRTRISRCQVCMKRT
```

An example nucleotide sequence encoding COL4A3 is NM_000091.5. An example nucleotide sequence encoding COL4A4 is NM_000092.5. An example nucleotide sequence encoding COL4A5 is NM_000495.5.

Suitably, the COL4A3 transgene may comprise or consist of the polynucleotide sequence shown as SEQ ID NO: 4, or a variant which is at least 70% identical to SEQ ID NO: 4. Suitably, the variant may be at least 75%, at least 80%, at least 85%, at least 90%, at least 95%, at least 98%, at least 99% identical to SEQ ID NO: 4.

Suitably, the COL4A4 transgene may comprise or consist of the polynucleotide sequence shown as SEQ ID NO: 5, or a variant which is at least 70% identical to SEQ ID NO: 5. Suitably, the variant may be at least 75%, at least 80%, at least 85%, at least 90%, at least 95%, at least 98%, at least 99% identical to SEQ ID NO: 5.

Suitably, the COL4A5 transgene may comprise or consist of the polynucleotide sequence shown as SEQ ID NO: 6, or a variant which is at least 70% identical to SEQ ID NO: 6. Suitably, the variant may be at least 75%, at least 80%, at least 85%, at least 90%, at least 95%, at least 98%, at least 99% identical to SEQ ID NO: 6.

```
Exemplary COL4A3 transgene sequence
                              (SEQ ID NO: 4)
atgagcgcccggaccgcccccaggccgcaggtgctcctgctgccg ctcctgctggtgctcctggcggcggcgcccgcagccagcaagggt tgtgtctgtaaagacaaaggccagtgcttctgtgacggggccaaa ggggagaaggggagaagggctttcctggacccccggttctcct ggccagaaaggattcacaggtcctgaaggcttgcctggaccgcag ggacccaagggctttccaggacttccaggactcacgggttccaaa ggtgtaaggggaataagtggattgccaggattttctggttctcct ggacttccaggcaccccaggcaataccgggccttacggacttgtc ggtgtaccaggatgcagtggttctaagggtgagcaggggtttcca
```

-continued

```
ggactcccagggacactgggctacccagggatcccgggtgctgct ggttttgaaaggacaaaagggtgctcctgctaaagaagaagatata gaacttgatgcaaaaggcgaccccgggttgccaggggctccagga ccccagggtttgccaggccctccaggttttcctgggcctgttggc ccacctggtcctccgggattctttggctttccaggagccatggga cctagaggacctaagggtcacatgggtgaaagagtgataggacat aaaggagagcggggtgtgaaagggttaacaggacccccgggacca ccaggaacagttattgtgaccctaactggcccagataacagaacg gacctcaaggggggaaaagggagacaagggagcaatgggcgagcct ggacctcctggaccctcaggactgcctggagaatcatatggatct gaaaagggtgctcctggagaccctggcctgcagggaaaacccgga aaagatggtgttcctggcttccctggaagtgagggagtcaagggc aacaggggtttccctgggttaatgggtgaagatggcattaaggga cagaaaggggacattggccctccaggatttcgtggtccaacagaa tattatgacacataccaggaaaagggagatgaaggcactccaggc ccaccagggcccagaggagctcgtggcccacaaggtcccagtggt cccccccggagttcctggaagtcctggatcatcaaggcctggcctc agaggagcccctggatggccaggcctgaaaggaagtaaaggggaa cgaggccgcccaggaaaggatgccatgggggactcctgggtcccca ggttgtgctggttcaccaggtcttccaggatcaccgggacctcca ggaccgccaggtgacatcgtttttcgcaagggtccacctggagat cacggactgccaggctatctagggtctccaggaatcccaggagtt gatgggcccaaaggagaaccaggcctcctgtgtacacagtgccct tatatcccagggcctcccggtctcccaggattgccagggttacat ggtgtaaaaggaatcccaggaagacaaggcgcagctggcttgaaa ggaagcccagggtccccaggaaatacaggtcttccaggatttcca ggtttcccaggtgcccagggtgacccaggacttaaaggagaaaaa ggtgaaacacttcagcctgaggggcaagtgggtgtcccaggtgac ccggggctcagaggccaacctgggagaaagggcttggatggaatt cctggaactccgggagtgaaaggattaccaggacctaaaggcgaa ctggctctgagtggtgagaaaggggaccaaggtcctccaggggat cctggctcccctgggtccccaggacctgcaggaccagctggacca cctggctacggaccccaaggagaacctggtctccagggcacgcaa ggagttcctggagcccccggaccacccgagaagccggccctagg ggagagctcagtgtttcaacaccagttccaggcccaccaggacct ccagggccccctggccatcctggcccccaaggtccacctggtatc cctggatccctggggaaatgtggagatcctggtcttccagggcct gatggtgaaccaggaattccaggaattggatttcctgggcctcct ggacctaaggggagaccaaggttttccaggtacaaaaggatcactg ggttgtcctggaaaaatgggagagcctgggttacctggaaagcca ggcctcccaggagccaagggagaaccagcagtagccatgcctgga
```

-continued ggaccaggaacaccaggttttccaggagaaagaggcaattctggg gaacatggagaaattggactccctggacttccaggtctccctgga actccaggaaatgaagggcttgatggaccacgaggagatccaggg cagcctggaccacctggagaacaaggaccccaggaaggtgcata gagggtcccaggggagcccaaggacttccaggcttaaatggattg aaagggcaacaaggcagaagaggtaaaacggggccaaagggagac ccaggaattccaggcttggatagatcaggatttcctggagaaact ggatcaccaggaattccaggtcatcaaggtgaaatgggaccactg ggtcaaagaggatatccaggaaatccgggaatttttagggccacca ggtgaagatggagtgattgggatgatgggctttcctggagccatt ggccctccagggcccctgggaacccaggcacaccagggcagagg gggagccctggaattccaggagtaaagggccagagagggaacccca ggagccaagggggaacaaggagataaaggaaatcccgggccttca gagatatcccacgtaatagggggacaaaggagaaccaggtctcaaa ggattcgcaggaaatccaggtgagaaaggaaacagaggcgttcca gggatgccaggtttaaagggcctcaaaggactacccggaccagca ggaccaccaggccccagaggagatttgggcagcactgggaatcct ggagaaccaggactgcgtggtataccaggaagcatggggaacatg ggcatgccaggttctaaaggaaaaaggggaactttgggattccca ggtcgagcaggaagaccaggcctcccaggtattcatggtctccag ggagataagggagagccaggttattcagaaggtacaaggccagga ccaccgggaccaacggggatccaggactgccgggtgatatggga aagaaaggagaaatggggcaacctggcccacctggacatttgggg cctgctggacctgagggagcccctggaagtcctggaagtcctggc ctcccaggaaagccaggtcctcatggtgatttgggtttttaaagga atcaaaggcctcctgggccctccaggaatcagaggccctccaggt cttccaggatttccaggatctcctggaccaatgggtataagaggt gaccaaggacgtgatggaattcctggtccagccggagaaaaggga gaaacgggtttattgagggcccctccaggcccaagagggaaccct ggtgctcaaggagccaaaggagacaggggagccccaggttttcct ggcctcccgggcagaaaagggccatgggagatgctggacctcga ggacccacaggcatagaaggattcccagggccaccaggtctgccc ggtgcaattatccctggccagacaggaaatcgtggtccaccaggc tcaagaggaagcccaggtgcgcctggtccccctggacctccaggg agtcatgtaataggcataaaaggagacaaagggtctatgggccac cctggcccaaaaggtccacctggaactgcaggagacatgggacca ccaggtcgtctgggagcaccaggtactccaggtcttccaggaccc agaggtgatcctggattccaggggtttccaggcgtgaaaggagaa aagggtaatcctggatttctaggatccattggacctccaggacca attgggccaaaaggaccacctggtgtacgtggagaccctggcaca cttaagattatctcccttccaggaagcccagggccacctggcaca cctggagaaccagggatgcagggagaacctgggccaccagggcca cctggaaacctaggaccctgtgggccaagaggtaagccaggcaag gatggaaaaccaggaactcctggaccagctggagaaaaaggcaac aaaggttctaaaggagagccaggaccagctggatcagatggattg ccaggtttgaaaggaaaacgtggagacagtggatcacctgcaacc tggacaacgagaggctttgtcttcacccgacacagtcaaaccaca gcaattccttcatgtccagagggggacagtgccactctacagtgggg ttttctttttcttttttgtacaaggaaatcaacgagcccacggacaa gaccttggaactcttggcagctgcctgcagcgatttaccacaatg ccattcttattctgcaatgtcaatgatgtatgtaattttgcatct cgaaatgattattcatactggctgtcaacaccagctctgatgcca atgaacatggctcccattactggcagagcccttgagccttatata agcagatgcactgtttgtgaaggtcctgcgatcgccatagccgtt cacagccaaaccactgacattcctccatgtcctcacggctggatt tctctctggaaaggattttcattcatcatgttcacaagtgcaggt tctgagggcaccgggcaagcactggcctcccctggctcctgcctg gaagaattccgagccagcccatttctagaatgtcatggaagagga acgtgcaactactattcaaattcctacagtttctggctggcttca ttaaacccagaaagaatgttcagaaagcctattccatcaactgtg aaagctgggaattagaaaaaataataagtcgctgtcaggtgtgc atgaagaaaagacactga Exemplary COL4A4 transgene sequence
                                    (SEQ ID NO: 5)
atgtggtctctgcacatagtactaatgaggtgctccttcagattg accaagtccttggccacaggtccctggtcacttatactcattctc ttttctgtacaatatgtatatgggagtggaaagaaatacattggt ccttgtggaggaagagattgctctgtttgccactgtgttcctgaa aaggggtctcggggtccaccaggaccaccagggccacagggtcca attggaccccctgggagccccaggacccattgggctttcaggagag aaaggaatgagaggggaccgcggccctcctggagcagcaggggac aaaggagataaggggtccaactggtgttcctggatttccaggttta gatggcatacctgggcacccaggcctcctggacccagaggcaaa cctggtatgagtggccacaatggctcaagaggtgacccagggttt ccaggaggaagaggagctcttggcccaggaggcccctaggccat cctggggaaaaggagaaaaaggaaattcagtgttcattttaggt gccgttaaaggtattcagggagacagaggggacccaggactgcct ggcttaccaggatcttggggtgcaggaggaccggcaggtcccaca ggatatcctggagagccaggttagtgggacctccgggccaacca gggcgtccaggtttgaaaggaaatcccggtgtgggagtaaagggg caaatgggagacccgggtgaggttggtcagcaaggttctcctgga cccaccctgttggtagagccacctgacttttgtctctataaagga -continued

```
gaaaagggtataaaaggaattcctggaatggttggactgccagga ccaccaggacgcaaggggagaatctggtattggggcaaaaggagaa aaaggtattcctggatttccagggcctcggggggatcctggttcc tatggatctccaggttttccaggattaaaagggagaactaggactg gttggagatcctgggctatttggattaattggcccaaaggggggat cctggaaatcgagggcacccaggaccaccaggtgttttggtgact ccacctcttccactcaaaggcccaccaggggacccagggttccct ggccgctatggagaaacagggggatgttggaccacctggtcccccca ggtctcttgggcagaccaggggaagcctgtgcaggcatgatagga cccctgggccacaaggatttcctggtcttcctgggcttccagga gaagctggtattcctgggagacctgattctgctccaggaaaacca gggaagccaggatcacctggcttgcctggagcaccaggcctgcag ggcctcccaggatcaagtgtgatatactgtagtgttgggaacccc ggaccacaaggaataaaaaggcaaagttggtcccccaggaggaaga ggcccaaaaggagaaaaaggaaatgaaggactctgtgcctgtgag cctggacccatgggcccccctggccctccaggacttcctgggagg caggggagtaagggagacttggggctccctggctggcttggaaca aaaggtgacccaggacctcctggtgctgaaggacctccagggcta ccaggaaagcatggtgcctctggaccacctggcaacaaaggggcg aagggtgacatggttgtatcaagagttaaagggcacaaaggagaa agaggtcctgatgggcccccaggatttccagggcagccaggatca catggtcgggatggacatgctggagaaaaagggggatccaggacct ccagggatcatgaagatgcgaccccaggtggtaaaggatttcct ggacctctgggccccccaggcaaagcaggacctgtggggcccccca ggactgggatttcctggtccaccaggagagcgaggccacccagga gttccaggccacccaggtgtgaggggccctgatggcttgaagggt cagaaaggtgacacaatttcttgcaacgtaacctaccctgggagg catggccctccaggttttgatggacctccaggtccgaagggattt ccaggtccccaaggtgcccctgggctgagtggttcagatgggcat aaaggcagacctggcacaccaggaacagcggaaataccaggtcca cctggttttcgtggtgacatgggagatccggtttttggaggtgaa aaggggtcctcccctgttgggcccccaggccctcccggctcacca ggagtgaatggtcagaaaggaatcccgggagaccctgcatttggt cacctgggaccccgggaaagaggggtctttcaggagtgccaggg ataaaaggacccagaggtgatccgggatgtccaggggctgaaggg ccagctggcattcctggattcctaggtctcaaaggtcccaaaggc agagagggacatgctgggtttccaggtgtcccaggtccacctggc cattcctgtgaaagaggtgctccagggataccagggcaaccggga ctccctgggtatccaggtagcccaggtgctccaggtgggaaagga cagccgggagatgtggggcctcccgggccagctggaatgaaaggc
```

-continued

```
ctccccggactcccaggacggcctggggcacatggtcccccaggc ctcccaggaatcccaggtccctttggagatgatgggctacctggt cctccaggtccaaagggaccccgggggctgcctggttttcccaggt tttcccggagaaagaggaaagcctggtgcagagggatgtcctggc gcaaagggagaacctggagagaagggcatgtctggccttcctgga gaccgggggactgagaggggccaaaggagccataggacctcccgga gatgaaggagaaatggctatcattttcacaaaagggaacacctggg gaacctggacctcctggagatgatggattcccaggagaaagaggt gataaaggaactcccgggatgcaaggggagaagaggagagccggga agatacggaccacctggatttcacagagggggaacctggtgagaaa ggtcagccagggcctcctggaccccccaggccctccaggctcaact ggtctaagagggttcattggtttttccaggacttccaggtgaccag ggtgagccaggttctccaggtcccccctggattttttcaggaattgat ggagcaagaggacctaaaggaaacaaaggtgaccctgccagtcac tttggtccacctggtccaaagggtgagccaggtagccctggatgt ccagggcattttggagcatccggagagcagggcttgcctggtatt caagggcccagaggatcacctggaaggccagggccacctggctcc tctggaccaccaggggtgcccaggtgatcacgggatgcctgggctg aggggacagccaggagaaatgggagaccctgggccaagaggcctc caggggggatccaggataccaggtcctccgggaataaaaggtccc tccggatcacctggcctgaacggcttgcatggattgaaaggtcag aaaggaactaaaggtgcttcaggttttgcatgatgtggggccacct ggtccagtgggaataacctgggctaaaagggggagagaggagaccct gggagcccaggaatctctcctccaggtcctcgtggaaagaaaggt cccccaggaccccccagggagttcaggaccacctggtcctgcaggt gccacaggaagagctcctaaggacattcctgacccgggtccacct ggagatcagggacctcctggtcctgatggcccaagaggagcacct gggcctccaggcctccctgggagtgttgaccttctgagagggggag ccaggtgactgtggtctaccagggccaccaggtccccctggccca ccaggccctccaggatacaaaggctttccaggatgtgatggaaaa gatggccagaaaggaccagtgggattcccgggaccgcagggacca catggatttcctgggccacctggagagaagggtttacctggacct ccaggagaaaagggcccactggtcttccgggtcccagaggtgaa ccggggccacctgcagatgtggatgactgtccccgaatcccaggc cttcctgggcgccaggcatgagaggaccagaaggagccatgggg ctccctggaatgagaggcccctcaggaccagggtgcaaaggagag cctgggctggatggcaggaggggtgtggatggcgtccctgggtct cctgggcctcccggacgtaaaggtgacacaggagaagacggctac cctggaggaccagggcctcctggtcccattggggatcctgggccc aaagggtttggccctggatacctcggtggcttcctcctggttctc cacagtcagacggaccaggagcccacctgcccccctgggcatgccc
```

-continued aggctctggactgggtatagtctgttatacctggaagggcaagag aaagctcacaatcaagaccttggtctggcagggtcttgccttccc gtatttagcacgctgccctttgcctactgcaacatccaccaggtg tgccactatgcccagagaaacgacagatcctactggctggccagc gctgcgccctccccatgatgccactctctgaagaggcgatccgc ccctatgtcagccgctgtgcggtatgcgaggccccggcccaggcg gtggcggtgcacagccaggaccagtccatcccccatgtccgcag acctggaggagcctctggatcgggtattcattcctgatgcacaca ggagctggggaccaaggaggagggcaggcccttatgtcacctggc agctgcctggaagatttcagagcagcaccattccttgaatgccag ggccggcagggaacttgccactttttcgcaaataagtatagcttc tggctcacaacggtgaaagcagacttgcagttttcctctgctcca gcaccagacaccttaaaagaaagccaggcccaacgccagaaatc agccggtgccaggtctgcgtgaagtatagctag Exemplary COL4A5 transgene sequence (SEQ ID NO: 6)

atgaaactgcgtggagtcagcctggctgccggcttgttcttactg gccctgagtctttggggggcagcctgcagaggctgcggcttgctat gggtgttctccaggatcaaagtgtgactgcagtggcataaaaggg gaaaagggagagagagggtttccaggtttggaaggacacccagga ttgcctggatttccaggtccagaagggcctccggggcctcggggga caaaagggtgatgatggaattccagggccaccaggaccaaaagga atcagaggtcctcctggacttcctggatttccagggacaccaggt cttcctggaatgccaggccacgatggggcccccaggacctcaaggt attcccggatgcaatggaaccaagggagaacgtggatttccaggc agtcccggttttcctggtttacagggtcctccaggacccctgggg atcccaggtatgaagggtgaaccaggtagtataattatgtcatca ctgccaggaccaaaggtaatccaggatatccaggtcctcctgga atacaaggcctacctggtcccactggtataccagggccaattggt cccccaggaccaccaggtttgatgggccctcctggtccaccagga cttccaggacctaaggggaatatgggcttaaatttccagggaccc aaaggtgaaaaaggtgagcaaggtcttcagggcccacctgggcca cctgggcagatcagtgaacagaaaagaccaattgatgtagagttt cagaaaggagatcagggacttcctggtgaccgagggcctcctgga cctccaggatacgtggtcctccaggtcccccaggtggtgagaaa ggtgagaagggtgagcaaggagagccaggcaaaagaggtaaacca ggcaaagatggagaaaatggccaaccaggaattcctggttttgcct ggtgatcctggttaccctggtgaacccggaagggatggtgaaaag ggccaaaaaggtgacactgggcccacctggacctcctggacttgta attcctagacctgggactggtataactataggagaaaaaaggaaac attgggttgcctgggttgcctggagaaaaaaggagagcgaggattt -continued cctggaatacagggtccacctggccttcctggacctccagggggct gcagttatgggtcctcctggccctcctggatttcctggagaaaagg ggtcagaaaggtgatgaaggaccacctggaatttccattcctgga cctcctggacttgacggacagcctggggctcctgggcttccaggg cctcctggccctgctggccctcacattcctcctagtgatgagata tgtgaaccaggccctccaggccccccaggatctccaggtgataaa ggactccaaggagaacaaggagtgaaaggtgacaaaggtgacact tgcttcaactgcattggaactggtatttcagggcctccaggtcaa cctggttttgccaggtctcccaggtcctccaggatctcttggtttc cctggacagaaagggaaaaaggacaagctggtgcaactggtccc aaaggattaccaggcattccaggagctccaggtgctccaggctt cctggatctaaaggtgaacctggtgatatcctcacttttccagga atgaagggtgacaaaggagagttgggttcccctggagctccaggg cttcctggtttacctggcactcctggacaggatggattgccaggg cttcctggcccgaaaggagagcctggtggaattacttttaagggt gaaagaggtcccctgggaacccaggtttaccaggcctcccaggg aatatagggcctatgggtccccctggtttcggccctccaggccca gtaggtgaaaaaggcatacaaggtgtggcaggaaatccaggccag ccaggaataccaggtcctaaaggggatccaggtcagactataacc cagccggggaagcctggcttgcctggtaacccaggcagagatggt gatgtaggtcttccaggtgaccctggacttccagggcaaccaggc ttgccagggatacctggtagcaaaggagaaccaggtatccctgga attgggcttcctggaccacctggtcccaaaggctttcctggaatt ccaggacctccaggagcacctgggacacctggaagaattggtcta gaaggccctcctgggccacccggctttccaggaccaaaggtgaa ccaggatttgcattacctgggccacctgggccaccaggacttcca ggtttcaaaggagcacttggtccaaaaggtgatcgtggtttccca ggacctccgggtcctccaggacgcactggcttagatgggctccct ggaccaaaaggtgatgttggaccaaatggacaacctggaccaatg ggacctcctgggctgccaggaataggtgttcagggaccaccagga ccaccagggattcctgggccaataggtcaacctggtttacatgga ataccaggagagaaggggggatccaggacctcctggacttgatgtt ccaggacccccaggtgaaagaggcagtccagggatccccggagca cctggtcctataggacctccaggatcaccagggcttccaggaaaa gcaggtgcctctggatttccaggtaccaaaggtgaaatgggtatg atgggacctccaggcccaccaggacctttgggaattcctggcagg agtggtgtacctggtcttaaaggtgatgatggcttgcagggtcag ccaggacttcctggccctacaggagaaaaaggtagtaaaggagag cctggccttccaggccctcctggaccaatggatccaaatcttctg ggctcaaaaggagagaagggggaacctggcttaccaggtataact ggagtttcagggccaaaaggttatcagggtttgcctggagaccca -continued

```
gggcaacctggactgagtggacaacctggattaccaggaccacca ggtcccaaaggtaaccctggtctccctggacagccaggtcttata ggacctcctggacttaaaggaaccatcggtgatatgggttttcca gggcctcagggtgtggaagggcctcctggaccttctggagttcct ggacaacctggctccccaggattacctggacagaaaggcgacaaa ggtgatcctggtatttcaagcattggtcttccaggtcttcctggt ccaaagggtgagcctggtctgcctggatacccagggaaccctggt atcaaaggttctgtgggagatcctggttttgcccggattaccagga acccctggagcaaaaggacaaccaggccttcctggattcccagga accccaggccctcctggaccaaaaggtattagtggccctcctggg aaccccggccttccaggagaacctggtcctgtaggtggtggaggt catcctgggcaaccagggcctccaggcgaaaaaggcaaacccggt caagatggtattcctggaccagctggacagaagggtgaaccaggt caaccaggctttggaaacccaggaccccctggacttccaggactt tctggccaaaagggtgatggaggattacctgggattccaggaaat cctggccttccaggtccaaagggcgaaccaggcttttcacggtttc cctggtgtgcagggtccccccaggccctcctggttctccgggtcca gctctggaaggacctaaaggcaaccctgggccccaaggtcctcct gggagaccaggtctaccaggtccagaaggtcctccaggtctccct ggaaatggaggtattaaaggagagaagggaaatccaggccaacct gggctacctggcttgcctggtttgaaaggagatcaaggaccacca ggactccagggtaatcctggccggccgggtctcaatggaatgaaa ggagatcctggtctccctggtgttccaggattcccaggcatgaaa ggacccagtggagtacctggatcagctggccctgagggggaaccg ggacttattggtcctccaggtcctcctggattacctggtccttca ggacagagtatcataattaaaggagatgctggtcctccaggaatc cctggccagcctgggctaaagggtctaccaggacccccaaggacct caaggcttaccaggtccaactggccctccaggagatcctggacgc aatggactccctggctttgatggtgcaggagggcgcaaaggagac ccaggtctgccaggacagccaggtacccgtggtttggatggtccc cctggtccagatggattgcaaggtcccccaggtcccccctggaacc tcctctgttgcacatggatttcttattacacgccacagccagaca acggatgcaccacaatgcccacagggaacacttcaggtctatgaa ggcttttctctcctgtatgtacaaggaaataaaagagcccacggt caagacttggggacggctggcagctgccttcgtcgctttagtacc atgcctttcatgttctgcaacatcaataatgtttgcaactttgct tcaagaaatgactattcttactggctctctaccccagagcccatg ccaatgagcatgcaacccctaaagggccagagcatccagccattc attagtcgatgtgcagtatgtgaagctccagctgtggtgatcgca gttcacagtcagacgatccagattccccattgtcctcagggatgg
```

-continued

```
gattctctgtggattggttattccttcatgatgcatacaagtgca ggggcagaaggctcaggtcaagccctagcctccctggttcctgc ttggaagagtttcgttcagctcccttcatcgaatgtcatgggagg ggtacctgtaactactatgccaactcctacagcttttggctggca actgtagatgtgtcagacatgttcagtaaacctcagtcagaaacg ctgaaagcaggagacttgaggacacgaattagccgatgtcaagtg tgcatgaagaggacataa
```

The COL4A3, COL4A4, or COL4A5 transgene may be codon-optimised. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available. Codon usage tables are known in the art for mammalian cells (e.g. humans), as well as for a variety of other organisms.

Regulatory Sequences

Promoter

The viral vector of the invention may comprise a promoter to facilitate expression of the COL4A3, COL4A4, or COL4A5 polypeptide. Suitably, the promoter may be operably linked to the COL4A3, COL4A4, or COL4A5 transgene.

Preferably, the promoter is operable in a podocyte cell. Preferably, the promoter is capable of driving transgene expression in podocytes. Preferably, the viral vector of the invention comprises a podocyte-specific promoter. Suitably, COL4A3, COL4A4, or COL4A5 transgene is operably linked to the podocyte-specific promoter.

As described above, the present inventors have developed a minimal nephrin promoter which is shorter than known minimal nephrin promoters and surprisingly capable of driving transgene expression in podocytes. The promoter also surprisingly retains podocyte-specificity. Such a minimal nephrin promoter can be used to minimise the cargo size and aid packaging of full length COL4A3, COL4A4 or COL4A5.

Use of a podocyte-specific promoter, such as a minimal nephrin promoter, allows the viral vector to be targeted specifically to podocytes (Moeller et al., 2002; Picconi et al., 2014). Suitable minimal nephrin promoters include NPHS1 and podocin promoter NPHS2. This enables transgene expression to be specifically targeted to podocytes in the glomerular basement membrane of the kidney and minimises off-target expression. As podocytes are terminally differentiated and non-dividing cells they can be targeted for stable expression of the transgene and reduce or avoid any risk of vector dilution effect. In preferred embodiments of the invention the promoter is NPHS1. One example of a suitable DNA sequence for the NPHS1 promoter is shown in FIG. 1. As with the transgene, the species of the promotor is preferably matched to the patient species. For example, when treating a human patient one would typically use human NHPS1 or human NPHS2.

As used herein, a "podocyte-specific promoter" may be a promoter which preferentially facilitates expression of a transgene in podocytes. Suitably, a podocyte-specific promoter may facilitate higher expression of a transgene in podocytes as compared to other cell-types. For example, a podocyte-specific promoter may be a promoter which facilitates transgene expression levels at least 10% higher, at least 20% higher, at least 30% higher, at least 40% higher, at least 50% higher, at least 100% higher, at least 200% higher, at least 300% higher, at least 400% higher, at least 500% higher, or at least 1000% higher in podocytes as compared to expression levels in other cell-types.

Transgene expression may be measured by any suitable method known in the art. For example by measuring the expression of a reporter transgene, e.g. GFP, operably linked to the promoter, wherein expression of the reporter transgene correlates with the ability of the promoter to facilitate expression of a gene. Expression of the reporter transgene, e.g. GFP may be determined by any suitable method e.g. FACS. For example, a podocyte-specific promoter may facilitate higher expression of a reporter transgene in conditionally immortalised podocytes compared to other cell-types e.g. glomerular endothelial cells. Suitable podocyte cell lines will be well known to those of skill in the art, for example CIHP-1. Methods to generate immortalized podocytes will be well known to those of skill in the art. Suitable methods are described in Ni, L., et al., 2012. Nephrology, 17(6), pp. 525-531.

Suitably, the promoter may be a minimal podocyte-specific promoter. The promoter may have a length of about 1.2 kb or less. Suitably, the promoter has a length of about 1.18 kb or less, about 1.17 kb or less, about 1.16 kb or less, about 1.15 kb or less, about 1.14 kb or less, about 1.13 kb or less, about 1.12 kb or less, about 1.11 kb or less, or about 1.10 kb or less. Suitably, the promoter has a length of about 1.15 kb or less. The promoter may have a length of about 1.1 kb or less. In some embodiments, the promoter has a length of about 1.1 kb or less, 1.0 kb or less, about 0.9 kb or less, about 0.8 kb or less, about 0.7 kb or less, about 0.6 kb or less, about 0.5 kb or less, about 0.4 kb or less, or about 0.3 kb or less.

In some embodiments, the promoter has a length of about 0.8 kb or less, about 0.7 kb or less, about 0.6 kb or less, about 0.5 kb or less, about 0.4 kb or less, or about 0.3 kb or less. In some embodiments, the promoter has a length of 818 bp or less. In some embodiments, the promoter has a length of 800 bp or less. In some embodiments, the promoter has a length of about 0.5 kb or less, about 0.4 kb or less, or about 0.3 kb or less. In some embodiments, the promoter has a length of about 0.3 kb or less.

The promoter may have a length of about 250 bp or more. In some embodiments, the promoter has a length of about 250-1100 bp, 250-1000 bp, 250-900 bp, 250-800 bp, 250-700 bp, 250-600 bp, 250-500 bp, 250-400 bp, 250-300 bp. The promoter may have a length of about 265 bp or more. In some embodiments, the promoter has a length of about 265-1100 bp, 265-1000 bp, 265-900 bp, 265-800 bp, 265-700 bp, 265-600 bp, 265-500 bp, 265-400 bp, 265-300 bp. In one embodiment, the promoter has a length of 250-300 bp, 250-280 bp, 255-275 bp, 260-270 bp, or about 265 bp. In one embodiment, the promoter has a length of 800-850 bp, 800-840 bp, 810-830 bp, 815-825 bp, or about 819 bp.

Minimal Nephrin Promoter

The viral vector of the invention may comprise a minimal nephrin promoter. Suitably, the minimal nephrin promoter may be operably linked to the COL4A3, COL4A4, or COL4A5 transgene.

The minimal nephrin promoter may be a minimal NPHS1 promoter. For example, the NPHS1 promoter may have a length of 1.2 kb or less. The NPHS1 gene encodes nephrin, which is selectively expressed in podocytes.

A minimal human NPHS1 promoter has been described in Moeller et al. 2002 J Am Soc Nephrol, 13(6): 1561-7 and Wong M A et al. 2000 Am J Physiol Renal Physiol, 279(6): F1027-32. This minimal NPHS1 is a 1.2 kb fragment and appears to be podocyte-specific. The 1.2 kb promoter region lacks a TATA box, but has recognition motifs for other transcription factors e.g. PAX-2 binding element, E-box and GATA consensus sequences.

Suitably, the minimal nephrin promoter may comprise or consist of the nucleotide sequence shown as SEQ ID NO: 7, or a variant which is at least 70% identical to SEQ ID NO: 7 (also shown in FIG. 1).

```
Exemplary minimal NPHS1 promoter
(SEQ ID NO: 7):
cacctgaggtcaggagttcgagaccagcgtggccaacatgatgaaa ccccgtctctagtaaaaatacaaaaattagccaggcatggtgcta tatacctgtagcaccagctacttgggagacagaggtgggagaatt acttgaacctgggaggttcaagccatgggaggtggaagttgcagt gagccgagatgccactgcactccagcctgagcaacagagcaagac tatctcaagaaaagaaagaaagaaagaaagagacttgccaaggtc atgtatcaggcaaggaagagctgggggcccagctggctgctccc ctgctgagctgggagaccaccttgatctgacttctcccatcttcc cagcctaagccaggccctggggtcacggaggctggggaggcaccg aggaacgcgcctggcatgtgctgacaggggattttatgctccagc tgggccagctgggaggagcctgctgggcagaggccagagctgggg gctctggaaggtacctgggggaggttgcactgtgagaatgagctc aagctgggtcagagagcagggctgactctgccagtgcctgcatca gcctcatcgctctcctaggctcctggcctgctggactctgggctg caggtccttcttgaaaggctgtgagtagtgagacaaggagcagga gtgagtggtggcaggagagaagatagagattgagagagagagaga gagagagacagagagagaggaagagacagagacaaaaggagagag aacggcttagacaaggagagaaagatggaaagataaagagactgg gcgcagtggctcacgcctgtaatcccaacacttggggaggccaag gtgggaggatggcttgaaggaaagagtctgagatcaacctggcca acatagtgagacccgtctctaaaaaaaaaagaaaaaaaaagaa aaaagaaaaaaaagttttttttaaagagacagagaaagagactcag agattgagactgagagcaagacagagagagatactcacagggaag aggggaagaggaaaacgagaaagggaggagagtaacggaaagaga taaaaaagaaaagcaggtggcagagacacacagagagggacccag agaaagccagacagacgcaggtggctggcagcgggcgctgtgggg gtcacagtaggggggacctgtg
```

Suitably, the variant may be at least 75%, at least 80%, at least 85%, at least 90%, at least 95%, at least 98% or at least 99% identical to SEQ ID NO: 7.

Suitably, the minimal nephrin promoter may comprise or consist of the nucleotide sequence shown as SEQ ID NO: 8, or a variant which is at least 70% identical to SEQ ID NO: 8.

Exemplary minimal NPHS1 promoter
(SEQ ID NO: 8):
cctgcagggcccactagtctgtaatcccagcattttgggaggctg aggcagatggatcacctgaggtcaggagttcgagaccagcctggc caacatgatgaaaccccgtctctagtaaaaatacaaaaattagcc aggcatggtgctatatacctgtagtaccagctacttgggagacag aggtgggagaattacttgaacctgggaggttcaagccatgggagg tggaagttgcagtgagccgagatgccactgcactccagcctgagc aacagagcaagactatctcaagaaaaaaaagaaagaaagaaaggg acttgccaaggtcatgtatcagggcaaggaagagctgggggccca gctggctgctcccctgctgagctgggagaccaccttgatctgact tctcccatcttcccagcctaagccaggccctggggtcacggaggc tggggaggcaccgaggaacgcgcctggcatgtgctgacagggaat tttatgctccagctgggcagctgggaggagcctgctgggcagag gccagagctggggctctggaaggtacctgggggaggttgcactg tgagaatgagctcaagctgggtcagagagcagggctgactctgcc agtgcctgcatcagcctcatcgctctcctaggctcctggcctgct ggactctgggctgcaggtccttcttgaaaggctgtgagtagtgag acaaggagcaggagtgaggggtggcaggagagaagatagagattg agagagagagagagagacagagagagaggaagagacagagaca aaaggagagaacggcttagacaaggagagaaagatggaagat aaagagactgggcgcagtggctcacgcctgtaatcccaacacttg gggaggccaaggtgggaggatggcttgaaggaaagagtctgagat caacctggccaacatagtgagaccccgtctctaaaaaaaaaaaag aaaaaaaaagaaaaaagaaaaaaaagtttttttaaagagacaga gaaagagactcagagattgagactgagagcaagacagagagagac actcacagggaagaggggaagaggaaaacgagaaagggaggagag taacggaaagagataaaaaagaaaagcaggtggcagagacacaga gagagggacccagagaaagccagacagacgcaggtggctggcagc gggcgctgtgggggtcacagtaggggggacctgtc Suitably, the variant may be at least 75%, at least 80%, at least 85%, at least 90%, at least 95%, at least 98% or at least 99% identical to SEQ ID NO: 8.

In some embodiments, the minimal nephrin promoter comprises or consists of the nucleotide sequence shown as SEQ ID NO: 9, or a variant which is at least 70% identical to SEQ ID NO: 9.

Exemplary minimal nephrin promoter-819 bp
(SEQ ID NO: 9)
Ggccctggggtcacggaggctggggaggcaccgaggaacgcgcct ggcatgtgctgacagggaatttttatgctccagctgggccagctgg gaggagcctgctgggcagaggccagagctgggggctctggaaggt acctgggggaggttgcactgtgagaatgagctcaagctgggtcag agagcagggctgactctgccagtgcctgcatcagcctcatcgctc -continued
tcctaggctcctggcctgctggactctgggctgcaggtccttctt gaaaggctgtgagtagtgagacaaggagcaggagtgaggggtggc aggagagaagatagagattgagagagagagagagagagacagaga gagaggaagagacagagacaaaaggagagagaacggcttagacaa ggagagaaagatggaaagataaagagactgggcgcagtggctcac gcctgtaatcccaacacttggggaggccaaggtgggaggatggct tgaaggaaagagtctgagatcaacctggccaacatagtgagaccc cgtctctaaaaaaaaaaaagaaaaaaaaaagaaaaaagaaaaaaa agttttttttaaagagacagagaaagagactcagagattgagactg agagcaagacagagagagacactcacagggaagaggggaagagga aaacgagaaagggaggagagtaacggaaagagataaaaaagaaaa gcaggtggcagagacacagagagagggacccagagaaagccagac agacgcaggtggctggcagcgggcgctgtggggggtcacagtaggg ggacctgtc Suitably, the variant may be at least 75%, at least 80%, at least 85%, at least 90%, at least 95%, at least 96%, at least 97%, at least 98%, at least 99% identical to SEQ ID NO: 9.

In preferred embodiments, the minimal nephrin promoter comprises or consists of the nucleotide sequence shown as SEQ ID NO: 10, or a variant which is at least 70% identical to SEQ ID NO: 10.

Exemplary minimal nephrin promoter-265 bp
(SEQ ID NO: 10)
Ggccctggggtcacggaggctggggaggcaccgaggaacgcgcct ggcatgtgctgacagggaatttttatgctccaggagcaagacagag agagacactcacagggaagaggggaagaggaaaacgagaaaggga ggagagtaacggaaagagataaaaaagaaaagcaggtggcagaga cacagagagagggacccagagaaagccagacagacgcaggtggct ggcagcgggcgctgtggggggtcacagtaggggggacctgtc Suitably, the variant may be at least 75%, at least 80%, at least 85%, at least 90%, at least 95%, at least 96%, at least 97%, at least 98%, at least 99% identical to SEQ ID NO: 10.

Suitably, the minimal nephrin promoter is derived from SEQ ID NO: 8 or a variant that has at least 70% identity to SEQ ID NO: 8. Suitably, the minimal nephrin promoter has one or more deletions compared to SEQ ID NO: 8 or a variant that has at least 70% identity to SEQ ID NO: 8. Suitably, the variant may be at least 75%, at least 80%, at least 85%, at least 90%, at least 95%, at least 96%, at least 97%, at least 98%, at least 99% identical to SEQ ID NO: 8. An exemplary variant is SEQ ID NO: 7.

Suitably, the minimal nephrin promoter comprises or consists of a nucleotide sequence according to SEQ ID NO: 8 and having one or more deletions, e.g. one or two deletions, or nucleotide sequence with at least 70%, at least 75%, at least 80%, at least 85%, at least 90%, at least 95%, at least 96%, at least 97%, at least 98%, or at least 99% identity thereto. Suitably, the minimal nephrin promoter comprises or consists of a nucleotide sequence according to SEQ ID NO: 8 and having two or more deletions, or nucleotide sequence with at least 70%, at least 75%, at least 80%, at least 85%, at least 90%, at least 95%, at least 96%, at least 97%, at least 98%, or at least 99% identity thereto. The deletions may be any size. Suitably, the deletions are each at least 50 bp, at least 100 bp, at least 150 bp, at least 200 bp, at least 250 bp, at least 300 bp, at least 350 bp, or at least 400 bp in size. Suitably, the deletions are each from 50 to 500 bp, from 100 to 500 bp, from 150 to 500 bp, from 200 to 500 bp, from 250 to 500 bp, from 300 to 500 bp, from 350 to 500 bp, or from 400 to 500 bp in size.

In some embodiments, the minimal nephrin promoter comprises or consists of a nucleotide sequence according to SEQ ID NO: 8, but wherein:

(i) position 1 to position n1 of SEQ ID NO: 8 is deleted, wherein n1 is an integer from 1 to 430; and/or (ii) position n2 to position n3 of SEQ ID NO: 8 is deleted, wherein n3≥n2, n2 is an integer from 508 to 1061, and n3 is an integer from 508 to 1061;

or a nucleotide sequence with at least 70%, at least 75%, at least 80%, at least 85%, at least 90%, at least 95%, at least 96%, at least 97%, at least 98%, or at least 99% identity thereto.

For example, the minimal nephrin promoter may comprise or consist of a nucleotide sequence having at least 70%, at least 75%, at least 80%, at least 85%, at least 90%, at least 95%, at least 96%, at least 97%, at least 98%, or at least 99% identity to a nucleotide sequence according to SEQ ID NO: 8, but wherein:

(i) position 1 to position n1 of SEQ ID NO: 8 is deleted, wherein n1 is an integer from 1 to 430; and/or (ii) position n2 to position n3 of SEQ ID NO: 8 is deleted, wherein n3≥n2, n2 is an integer from 508 to 1061, and n3 is an integer from 508 to 1061.

Suitably, n1 is an integer from 50 to 430, from 100 to 430, from 150 to 430, from 200 to 430, from 250 to 430, from 300 to 430, from 350 to 430, or from 400 to 430. In some embodiments, n1 is an integer from 100 to 430. In some embodiments, n1=430, i.e. position 1 to position 430 of SEQ ID NO: 8 is deleted.

The difference between n3 and n2 specifies the size of the deletion. Suitably, n3≥n2+49, n3≥n2+99, n3≥n2+149, n3≥n2+199, n3≥n2+249, n3≥n2+299, n3≥n2+349, n3≥n2+399, n3≥n2+449, n3≥n2+499, or n3≥n2+549. In some embodiments, n3≥n2+49.

The values that n2 and n3 take determine where the deletion is. Suitably, n2 and n3 are each integers from 550 to 1050, n2 and n3 are each integers from 600 to 1000, n2 and n3 are each integers from 650 to 950, n2 and n3 are each integers from 700 to 900, n2 and n3 are integers from 750 to 850. In some embodiments, n2=508 and n3=1061, i.e. position 508 to 1061 of SEQ ID NO: 8 is deleted.

Minimal Nephrin Promoter Regions

The present inventors have determined the regions of the nephrin promoter which drive transgene expression.

A promoter typically comprises a "core" and a "proximal" region. The "core promoter region" may comprise a transcription start site, a RNA polymerase binding sites and a general transcription factor binding site. The "proximal promoter region" may comprise primary regulatory elements and specific transcription factor binding sites which are required, for example, to facilitate effective and controllable transcription. The size and components of both the core and proximal promoter regions typically vary in a gene specific manner. A promoter may also comprise a 5' untranslated region (5' UTR) (also known as a leader sequence) downstream of the core promoter region and upstream from the initiation codon.

The minimal nephrin promoter may be a hybrid promoter. As used herein, a "hybrid promoter" comprises a combination of elements derived from different promoters. For example, a hybrid promoter may comprise a proximal promoter region derived from one pre-existing promoter and a core promoter from another pre-existing promoter to achieve the desired transgene expression. A muscle hybrid promoter is described in Piekarowicz, K., et al. (2019). Methods & clinical development, 15, 157-169.

In some embodiments, the minimal nephrin promoter comprises (i) the nucleotide sequence shown as SEQ ID NO: 12, or a variant which is at least 70% identical to SEQ ID NO: 12. Without wishing to be bound by theory, it is considered that a nucleotide sequence having at least about 70% identity to SEQ ID NO: 12 may provide a proximal promoter region.

```
Exemplary proximal promoter region
                                    (SEQ ID NO: 12)
GGCCCTGGGGTCACGGAGGCTGGGGAGGCACCGAGGAACGCGCCT

GGCATGTGCTGACAGGGAATTTTATGCTCCAG
```

Suitably, the variant may be at least 75%, at least 80%, at least 85%, at least 90%, at least 95%, at least 96%, at least 97%, at least 98%, at least 99% identical to SEQ ID NO: 12. The minimal nephrin promoter may comprise a variant of SEQ ID NO: 12 shown as SEQ ID NO: 13.

```
Exemplary variant proximal promoter region
                                    (SEQ ID NO: 13)
GGCCCTGGGGTCACGGAGGCTGGGGAGGCACCGAGGAACGCGCCT

GGCATGTGCTGACAGGGGATTTTATGCTCCAG
```

In some embodiments, the minimal nephrin promoter comprises (ii) the nucleotide sequence shown as SEQ ID NO: 14, or a variant which is at least 70% identical to SEQ ID NO: 14; the nucleotide sequence shown as SEQ ID NO: 15, or a variant which is at least 70% identical to SEQ ID NO: 15; and/or the nucleotide sequence shown as SEQ ID NO: 16, or a variant which is at least 70% identical to SEQ ID NO: 16.

In some embodiments, the minimal nephrin promoter comprises (ii) the nucleotide sequence shown as SEQ ID NO: 14, or a variant which is at least 70% identical to SEQ ID NO: 14. Without wishing to be bound by theory, it is considered that a nucleotide sequence having at least about 70% identity to SEQ ID NO: 14 may provide a core promoter region

```
Exemplary core promoter region
                                    (SEQ ID NO: 14)
GAGCAAGACAGAGAGAGACACTCACAGGGAAG
```

Suitably, the variant may be at least 75%, at least 80%, at least 85%, at least 90%, at least 95%, at least 96%, at least 97%, at least 98%, at least 99% identical to SEQ ID NO: 14. The minimal nephrin promoter may comprise a variant of SEQ ID NO: 14 shown as SEQ ID NO: 17.

```
Exemplary variant core promoter region
                                    (SEQ ID NO: 17)
GAGCAAGACAGAGAGAGATACTCACAGGGAAG
```

In some embodiments, the minimal nephrin promoter comprises (ii) the nucleotide sequence shown as SEQ ID NO: 15, or a variant which is at least 70% identical to SEQ ID NO: 15. Without wishing to be bound by theory, it is considered that a nucleotide sequence having at least about 70% identity to SEQ ID NO: 15 may provide a 5'UTR.

```
Exemplary 5'UTR
                                   (SEQ ID NO: 15)
AGGGGAAGAGGAAAACGAGAAAGGGAGGAGAGTAACGGAAAGAGA

TAAAAAAGAAAAGCAGGTGGCAGAGACACAGAGAGAGGGACCCAG

AGAAAGCCAGACAGACGCAGGTGGCTGGCAGCGGGCGCTGTGGGG

GTCACAGTAGGGGGACCTGTC
```

Suitably, the variant may be at least 75%, at least 80%, at least 85%, at least 90%, at least 95%, at least 96%, at least 97%, at least 98%, at least 99% identical to SEQ ID NO: 15. The minimal nephrin promoter may comprise a variant of SEQ ID NO: 15 shown as SEQ ID NO: 18.

```
Exemplary variant 5'UTR
                                   (SEQ ID NO: 18)
AGGGGAAGAGGAAAACGAGAAAGGGAGGAGAGTAACGGAAAGAGA

TAAAAAAGAAAAGCAGGTGGCAGAGACACACAGAGAGGGACCCAG

AGAAAGCCAGACAGACGCAGGTGGCTGGCAGCGGGCGCTGTGGGG

GTCACAGTAGGGGGACCTGTG
```

In some embodiments, the minimal nephrin promoter comprises (ii) the nucleotide sequence shown as SEQ ID NO: 16, or a variant which is at least 70% identical to SEQ ID NO: 16. Without wishing to be bound by theory, it is considered that a nucleotide sequence having at least about 70% identity to SEQ ID NO: 16 may provide a core promoter region and a 5'UTR.

```
Exemplary core promoter region and 5'UTR
                                   (SEQ ID NO: 16)
GAGCAAGACAGAGAGAGACACTCACAGGGAAGAGGGGAAGAGGAA

AACGAGAAAGGGAGGAGAGTAACGGAAAGAGATAAAAAAGAAAAG

CAGGTGGCAGAGACACAGAGAGAGGGACCCAGAGAAAGCCAGACA

GACGCAGGTGGCTGGCAGCGGGCGCTGTGGGGGTCACAGTAGGGG

GACCTGTC
```

Suitably, the variant may be at least 75%, at least 80%, at least 85%, at least 90%, at least 95%, at least 96%, at least 97%, at least 98%, at least 99% identical to SEQ ID NO: 16. The minimal nephrin promoter may comprise a variant of SEQ ID NO: 16 shown as SEQ ID NO: 19.

```
Exemplary variant core promoter region and
5'UTR
                                   (SEQ ID NO: 19)
GAGCAAGACAGAGAGAGATACTCACAGGGAAGAGGGGAAGAGGAA

AACGAGAAAGGGAGGAGAGTAACGGAAAGAGATAAAAAAGAAAAG

CAGGTGGCAGAGACACACAGAGAGGGACCCAGAGAAAGCCAGACA

GACGCAGGTGGCTGGCAGCGGGCGCTGTGGGGGTCACAGTAGGGG

GACCTGTG
```

In some embodiments, the minimal nephrin promoter comprises (iii) a nucleotide sequence having at least 70% identity to SEQ ID NO: 20, or one or more fragments thereof. Suitably, the minimal nephrin promoter comprises a nucleotide sequence having at least about 70% identity to SEQ ID NO: 20, or one or more fragments thereof, immediately downstream of the proximal promoter region and/or immediately upstream of the core promoter region.

The minimal nephrin promoter may comprise a nucleotide sequence that has at least 70%, at least 75%, at least 80%, at least 85%, at least 90%, at least 95%, at least 96%, at least 97%, at least 98% or at least 99% identity to SEQ ID NO: 20, or one or more fragments thereof. The minimal nephrin promoter may comprise the nucleotide sequence of SEQ ID NO: 20, or one or more fragments thereof.

```
Exemplary optional promoter region
                                   (SEQ ID NO: 20)
CTGGGCCAGCTGGGAGGAGCCTGCTGGGCAGAGGCCAGAGCTGGG

GGCTCTGGAAGGTACCTGGGGGAGGTTGCACTGTGAGAATGAGCT

CAAGCTGGGTCAGAGAGCAGGGCTGACTCTGCCAGTGCCTGCATC

AGCCTCATCGCTCTCCTAGGCTCCTGGCCTGCTGGACTCTGGGCT

GCAGGTCCTTCTTGAAAGGCTGTGAGTAGTGAGACAAGGAGCAGG

AGTGAGGGGTGGCAGGAGAGAAGATAGAGATTGAGAGAGAGAGAG

AGAGAGACAGAGAGAGAGGAAGAGACAGAGACAAAAGGAGAGAGA

ACGGCTTAGACAAGGAGAGAAAGATGGAAAGATAAAGAGACTGGG

CGCAGTGGCTCACGCCTGTAATCCCAACACTTGGGGAGGCCAAGG

TGGGAGGATGGCTTGAAGGAAAGAGTCTGAGATCAACCTGGCCAA

CATAGTGAGACCCCGTCTCTAAAAAAAAAAAAAGAAAAAAAAAAGA

AAAAAGAAAAAAAAGTTTTTTTAAAGAGACAGAGAAAGAGACTCA

GAGATTGAGACTGA
```

Suitably, the one or more fragments are (a) a 5' terminal fragment; and/or (b) a 3' terminal fragment. Suitably, the 5' terminal fragment may be immediately downstream of the proximal promoter region. Suitably, the 3' terminal fragment may be immediately upstream of the core promoter region. For example, the minimal nephrin promoter may comprise:

(a) a nucleotide sequence having at least 70% to positions 1 to x of SEQ ID NO: 20; and/or
(b) a nucleotide sequence having at least 70% identity to positions y to 554 of SEQ ID NO: 20;
wherein x and y are integers, and y>x.

The fragment(s) of SEQ ID NO: 20 may be any length. Suitably, the fragment(s) may have a length of about 500 bp or less, 450 bp or less, 400 bp or less, 350 bp or less, 300 bp or less, 250 bp or less, 200 bp or less, 150 bp or less, 100 bp or less, 50 bp or less, 40 bp or less, 30 bp or less, 20 bp or less, or 10 bp or less.

In some embodiments, the minimal nephrin promoter does not comprise SEQ ID NO: 20.

In some embodiments, the minimal nephrin promoter comprises (iv) a nucleotide sequence having at least 70% identity to SEQ ID NO: 21, or a fragment thereof. Suitably, the minimal nephrin promoter comprises a nucleotide sequence having at least about 70% identity to SEQ ID NO: 21, or a fragments thereof, immediately upstream of the proximal promoter region.

The minimal nephrin promoter may comprise a nucleotide sequence that has at least 70%, at least 75%, at least 80%, at least 85%, at least 90%, at least 95%, at least 96%, at least 97%, at least 98% or at least 99% identity to SEQ ID NO: 21, or a fragment thereof. The minimal nephrin promoter may comprise the nucleotide sequence of SEQ ID NO: 21, or one or more fragments thereof.

```
Exemplary optional upstream promoter region
                                   (SEQ ID NO: 21)
CCTGCAGGGCCCACTAGTCTGTAATCCCAGCATTTTGGGAGGCTG

AGGCAGATGGATCACCTGAGGTCAGGAGTTCGAGACCAGCCTGGC

CAACATGATGAAACCCCGTCTCTAGTAAAAATACAAAAATTAGCC

AGGCATGGTGCTATATACCTGTAGTACCAGCTACTTGGGAGACAG

AGGTGGGAGAATTACTTGAACCTGGGAGGTTCAAGCCATGGGAGG

TGGAAGTTGCAGTGAGCCGAGATGCCACTGCACTCCAGCCTGAGC

AACAGAGCAAGACTATCTCAAGAAAAAAAAGAAAGAAAGAAAGGG

ACTTGCCAAGGTCATGTATCAGGGCAAGGAAGAGCTGGGGGCCCA

GCTGGCTGCTCCCCTGCTGAGCTGGGAGACCACCTTGATCTGACT

TCTCCCATCTTCCCAGCCTAAGCCA
```

Suitably, the fragments is a 3' terminal fragment. For example, the minimal nephrin promoter may comprise a nucleotide sequence having at least 70% identity to positions z to 430 of SEQ ID NO: 21, wherein z is an integer.

The fragment of SEQ ID NO: 21 may be any length. Suitably, the fragment may have a length of about 400 bp or less, 350 bp or less, 300 bp or less, 250 bp or less, 200 bp or less, 150 bp or less, 100 bp or less, 50 bp or less, 40 bp or less, 30 bp or less, 20 bp or less, or 10 bp or less.

In some embodiments, the minimal nephrin promoter does not comprise SEQ ID NO: 21.

In some embodiments, the minimal nephrin promoter comprises or consists of from 5' to 3':
(i) a nucleotide sequence having at least 70% identity to SEQ ID NO: 12;
(iii) optionally a nucleotide sequence having at least 70% identity to SEQ ID NO: 20, or one or more fragments thereof; and
(ii) a nucleotide sequence having at least 70% identity to SEQ ID NO: 14, a nucleotide sequence having at least 70% identity to SEQ ID NO: 15, and/or a nucleotide sequence having at least 70% identity to SEQ ID NO: 16.

In some embodiments, the minimal nephrin promoter comprises or consists of from 5' to 3':
(i) a nucleotide sequence having at least 70% identity to SEQ ID NO: 12;
(iii) optionally (a) a nucleotide sequence having at least 70% identity to a 5' terminal fragment of SEQ ID NO: 20; and/or (b) a nucleotide sequence having at least 70% identity to a 3' terminal fragment of SEQ ID NO: 20; and
(ii) a nucleotide sequence having at least 70% identity to SEQ ID NO: 14, a nucleotide sequence having at least 70% identity to SEQ ID NO: 15, and/or a nucleotide sequence having at least 70% identity to SEQ ID NO: 16.

Minimal Nephrin Promoter Elements

The present inventors have determined the functional elements of the nephrin promoter which drive transgene expression.

The minimal nephrin promoter may comprise one or more of the following elements: (a) a retinoic acid receptor binding site; (b) a WT1 binding site; (c) an enhancer box; (d) a transcription factor binding region; and (e) a transcription initiation site.

Suitably, the minimal nephrin promoter comprises all of the following elements: (a) a retinoic acid receptor binding site; (b) a WT1 binding site; (c) an enhancer box; (d) a transcription factor binding region; and (e) a transcription initiation site.

A retinoic acid receptor (RAR) binding site refers to a polynucleotide sequence which is capable of binding RAR alpha, RAR beta, and/or RAR gamma. The RAR binding site may comprise or consist of a nucleotide sequence shown as SEQ ID NO: 22, or a nucleotide sequence having one or two substitutions, deletions, or insertions compared to SEQ ID NO: 22. The substitutions, deletions, or insertions may be any substitution, deletion, or insertion of a single nucleotide such that the RAR binding site retains at least one of its endogenous functions.

```
Exemplary RAR binding site
                                   (SEQ ID NO: 22)
    GGGGTCA
```

A WT1 binding site refers to a polynucleotide sequence which is capable of binding the zinc finger polypeptide encoded by the Wilms' tumor suppressor gene, WT1. The WT1 binding site may comprise or consist of a nucleotide sequence shown as SEQ ID NO: 23, or a nucleotide sequence having one, two or three substitutions, deletions, or insertions compared to SEQ ID NO: 23. The substitutions, deletions, or insertions may be any substitution, deletion, or insertion of a single nucleotide such that the WT1 binding region retains at least one of its endogenous functions.

```
Exemplary WT1 binding site
                                   (SEQ ID NO: 23)
    CGGAGGCTGGGGAGGCA
```

An enhancer box refers to a DNA response element found in some eukaryotes that acts as a protein-binding site. The enhancer box may comprise or consist of a nucleotide sequence shown as SEQ ID NO: 24, or a nucleotide sequence having one or two substitutions, deletions, or insertions compared to SEQ ID NO: 24. The substitutions, deletions, or insertions may be any substitution, deletion, or insertion of a single nucleotide such that the enhancer box retains at least one of its endogenous functions.

```
Exemplary enhancer box
                                   (SEQ ID NO: 24)
    ATGTG
```

One or more of (a) a retinoic acid receptor binding site; (b) a WT1 binding site; and (c) an enhancer box may be present in the proximal promoter region. Suitably, each of (a) a retinoic acid receptor binding site; (b) a WT1 binding site; and (c) an enhancer box are present in the proximal promoter region.

In some embodiments, one or more of the following elements is present in (i) the nucleotide sequence having at least 70% identity to SEQ ID NO: 12: (a) a RAR binding site at a position corresponding approximately to position 7 to position 13 of SEQ ID NO: 12; (b) a WT1 binding site at a position corresponding approximately to position 14 to position 30 of SEQ ID NO: 12; and (c) an enhancer box at a position corresponding approximately to position 49 to position 53 of SEQ ID NO: 12. In some embodiments, each of the elements are present in (i) the nucleotide sequence having at least 70% identity to SEQ ID NO: 12.

In some embodiments, one or more of the following nucleotide sequences is present in (i) the nucleotide sequence having at least 70% identity to SEQ ID NO: 12: (a) GGGGTCA at a position corresponding to position 7 to position 13 of SEQ ID NO: 12; (b) CGGAGGCTGGG-GAGGCA at a position corresponding to position 14 to position 30 of SEQ ID NO: 12; and (c) ATGTG at a position corresponding to position 49 to position 53 of SEQ ID NO: 12. In some embodiments, each of the nucleotide sequences are present in (i) the nucleotide sequence having at least 70% identity to SEQ ID NO: 12.

Suitably, the minimal nephrin promoter may comprise a transcription factor binding region comprising or consisting of a nucleotide sequence shown as SEQ ID NO: 25 or a nucleotide sequence having one, two, three, four or five substitutions, deletions, or insertions compared to SEQ ID NO: 25. The substitutions, deletions, or insertions may be any substitution, deletion, or insertion of a single nucleotide such that the transcription factor binding region retains at least one of its endogenous functions.

```
Exemplary transcription factor binding region
                                     (SEQ ID NO: 25)
GAGCAAGACAGAGAGAGACACTCACAGGGA
```

Other suitable transcription factor binding regions will be well known to those of skill in the art. For example, other suitable transcription factor binding regions include TAC-GAT (SEQ ID NO: 36), TATAAT (SEQ ID NO: 37), GATACT (SEQ ID NO: 38), TATGAT (SEQ ID NO: 39), and TATGTT (SEQ ID NO: 40).

Suitably, the minimal nephrin promoter may comprise a transcription initiation site which comprises or consists of an "AG" dinucleotide.

Suitably, the transcription factor binding site is operably linked to the transcription initiation site. Suitably, the transcription factor binding site may be directly upstream of the transcription initiation site. Without wishing to be bound by theory, it is considered that the transcription factor binding site and the transcription initiation site may provide a core promoter region.

Suitably the minimal nephrin promoter may comprise a 5' untranslated region. The 5' untranslated region may comprises or consists of a nucleotide sequence having at least about 70%, 80%, 90%, 95% or 99% sequence identity to SEQ ID NO: 15. The 5' untranslated region may comprise or consist of SEQ ID NO: 15.

Suitably, the 5' untranslated region is operably linked to the transcription initiation site. Suitably, the 5' untranslated region may be directly downstream of the transcription initiation site.

In some embodiments, the minimal nephrin promoter comprises or consists of from 5' to 3':

(i) a nucleotide sequence having at least 70% identity to SEQ ID NO: 12, wherein each of the following elements is present: (a) a RAR binding site at a position corresponding approximately to position 7 to position 13 of SEQ ID NO: 12; (b) a WT1 binding site at a position corresponding approximately to position 14 to position 30 of SEQ ID NO: 12; and (c) an enhancer box at a position corresponding approximately to position 49 to position 53 of SEQ ID NO: 12;

(iii) optionally a nucleotide sequence having at least 70% identity to SEQ ID NO: 20, or one or more fragments thereof; and (ii) a nucleotide sequence having at least 70% identity to SEQ ID NO: 14, a nucleotide sequence having at least 70% identity to SEQ ID NO: 15, or a nucleotide sequence having at least 70% identity to SEQ ID NO: 16.

Exemplary Minimal Nephrin Promoters

In some embodiments, the minimal nephrin promoter comprises or consists of the nucleotide sequence shown as SEQ ID NO: 9, or a variant which is at least 70% identical to SEQ ID NO: 9.

In some embodiments, the minimal nephrin promoter comprises the nucleotide sequence shown as SEQ ID NO: 9, or a variant which is at least 70% identical to SEQ ID NO: 9 and wherein the promoter has a length of about 1.1 kb or less.

In some embodiments, the minimal nephrin promoter consists of the nucleotide sequence shown as SEQ ID NO: 9, or a variant which is at least 70% identical to SEQ ID NO: 9.

Suitably, the variant may be at least 75%, at least 80%, at least 85%, at least 90%, at least 95%, at least 96%, at least 97%, at least 98%, at least 99% identical to SEQ ID NO: 9. The minimal nephrin promoter may comprise or consist of a variant of SEQ ID NO: 9 shown as SEQ ID NO: 34.

```
Exemplary minimal nephrin promoter
variant-819 bp
                                     (SEQ ID NO: 34)
GGCCCTGGGGTCACGGAGGCTGGGGAGGCACCGAGGAACGCGCCT

GGCATGTGCTGACAGGGGATTTTATGCTCCAGCTGGGCCAGCTGG

GAGGAGCCTGCTGGGCAGAGGCCAGAGCTGGGGGCTCTGGAAGGT

ACCTGGGGGAGGTTGCACTGTGAGAATGAGCTCAAGCTGGGTCAG

AGAGCAGGGCTGACTCTGCCAGTGCCTGCATCAGCCTCATCGCTC

TCCTAGGCTCCTGGCCTGCTGGACTCTGGGCTGCAGGTCCTTCTT

GAAAGGCTGTGAGTAGTGAGACAAGGAGCAGGAGTGAGGGGTGGC

AGGAGAGAAGATAGAGATTGAGAGAGAGAGAGAGAGAGAGAGACAGA

GAGAGAGGAAGAGACAGAGACAAAAGGAGAGAGAACGGCTTAGAC

AAGGAGAGAAAGATGGAAAGATAAAGAGACTGGGCGCAGTGGCTC

ACGCCTGTAATCCCAACACTTGGGGAGGCCAAGGTGGGAGGATGG

CTTGAAGGAAAGAGTCTGAGATCAACCTGGCCAACATAGTGAGAC

CCCGTCTCTAAAAAAAAAAGAAAAAAAAAAGAAAAAAGAAAAAAA

AGTTTTTTTAAAGAGACAGAGAAAGAGACTCAGAGATTGAGACTG

AGAGCAAGACAGAGAGAGATACTCACAGGGAAGAGGGGAAGAGGA

AAACGAGAAAGGGAGGAGAGTAACGGAAAGAGATAAAAAAGAAAA

GCAGGTGGCAGAGACACACAGAGAGGGACCCAGAGAAAGCCAGAC

AGACGCAGGTGGCTGGCAGCGGGCGCTGTGGGGGTCACAGTAGGG

GGACCTGTG
```

In some embodiments, the minimal nephrin promoter comprises or consists of the nucleotide sequence shown as SEQ ID NO: 10, or a variant which is at least 70% identical to SEQ ID NO: 10.

In some embodiments, the minimal nephrin promoter comprises the nucleotide sequence shown as SEQ ID NO: 10, or a variant which is at least 70% identical to SEQ ID NO: 10 and wherein the promoter has a length of about 1.1 kb or less.

In some embodiments, the minimal nephrin promoter consists of the nucleotide sequence shown as SEQ ID NO: 10, or a variant which is at least 70% identical to SEQ ID NO: 10.

Suitably, the variant may be at least 75%, at least 80%, at least 85%, at least 90%, at least 95%, at least 96%, at least 97%, at least 98%, at least 99% identical to SEQ ID NO: 10. The minimal nephrin promoter may comprise or consist of a variant of SEQ ID NO: 10 shown as SEQ ID NO: 35.

```
Exemplary minimal nephrin promoter
variant-265 bp
                              (SEQ ID NO: 35)
GGCCCTGGGGTCACGGAGGCTGGGGAGGCACCGAGGAACGCGCCT

GGCATGTGCTGACAGGGGATTTTATGCTCCAGGAGCAAGACAGAG

AGAGATACTCACAGGGAAGAGGGGAAGAGGAAAACGAGAAAGGGA

GGAGAGTAACGGAAAGAGATAAAAAAGAAAAGCAGGTGGCAGAGA

CACAGAGAGAGGGACCCAGAGAAAGCCAGACAGACGCAGGTGGCT

GGCAGCGGGCGCTGTGGGGGTCACAGTAGGGGGACCTGTC
```

Minimal Podocin Promoter

The viral vector of the invention may comprise a minimal podocin promoter.

Suitably, the minimal podocin promoter may be operably linked to the COL4A3, COL4A4, or COL4A5 transgene.

The minimal podocin promoter may be a minimal NPHS2 promoter. For example, the NPHS2 promoter may have a length of 0.6 kb or less. The NPHS2 gene encodes podocin, which is selectively expressed in podocytes.

A minimal human NPHS2 promoter has been described in Oleggini R, et al., 2006. Gene Expr. 13(1):59-66. This minimal NPHS2 is a 630 bp fragment which has shown expression in podocytes in vitro.

Suitably, the minimal podocin promoter may comprise or consist of the nucleotide sequence shown as SEQ ID NO: 11, or a variant which is at least 70% identical to SEQ ID NO: 11.

```
Exemplary minimal NPHS2 promoter
(SEQ ID NO: 11):
ggaaagttggggatgaggcgaaatttctgattttaccttaaagtga ccctaattcgatgaccttttgtggtttttttctttttttctttttt ctttttttacttggccctgcccaagcaggacctaaaaacaaacaga caaaaaaggttactaacaactgttcctctccacgaaaatctgcag taaaaggtaaaagatgtattcgtttgaagagaaaccagagcttg cgatgagcttctgtatctccgtcagccctctagcatgacattagg aaccctccaggagatgagtcttcacagcccgggttggcacctgca gacacgcacttttcaacgcccgcaccctgcccggggccggctctc ccacccaggcctctctctgcttcagcgccgcccccggccgtgggag tcggcgggcgcagtccacagctccaccaagacacagctgtcgggg ttccgggtgcgccccgcccgcgggcccccggtgtcccgcccctcgcc ctcagcccccacccgacggtctttagggtcccccgggcacgccac gcggacccgcagcgactccacagggactgcgctcccgtgccccta gcgctcccgcgctgctgctccagccgcccggcagctctgacc
```

Suitably, the variant may be at least 75%, at least 80%, at least 85%, at least 90%, at least 95%, at least 98% or at least 99% identical to SEQ ID NO: 11.

Other Promoters

Other non-podocyte-specific promoters for use in the present invention will be well known to those of skill in the art. In some embodiments, the promoter may have a length of about 300 bp or less. In some embodiments, the promoter has a length of about 290 bp or less, 280 bp or less, 270 bp or less, 260 bp or less, 250 bp or less, 240 bp or less, 230 bp or less, 220 bp or less, 210 bp or less, or 200 bp or less. Using a promoter which is about 300 bp or less in length may aid packaging of COL4A3, COL4A4 and COL4A5 transgenes into an AAV vector in their full length form.

Exemplary promoters which have a length of about 300 bp or less are described in Wang, D., et al., 1999. Gene therapy, 6(4), pp. 667-675. Wang et al. describes four short promoters that have significantly higher activity than the AAV ITR alone and are 102 bp to 200 bp in size. These promoters are the AAV-P5 (150 bp), SV40e (200 bp), TK1 (110 bp) and a second TK promoter (TK2) with an additional 10 bp deletion between the distal and the proximal element (102 bp).

Woodchuck Hepatitis Post-Transcriptional Regulatory Element

The viral vector may additionally comprise a Woodchuck hepatitis post-transcriptional regulatory element (WPRE). Suitably, the WPRE may be operably linked to the COL4A3, COL4A4, or COL4A5 transgene. WPRE is a DNA sequence that, when transcribed, creates a tertiary structure enhancing expression. Inclusion of WPRE may increase expression of the transgene delivered by the vector. The WPRE sequence may be mutated to reduce oncogenicity without significant loss of RNA enhancement activity (Schambach et al., 2005, incorporated herein by reference). One example of a suitable WPRE sequence is shown in FIG. 2.

Suitably, the WPRE may comprise or consist of the nucleotide sequence shown as SEQ ID NO: 26, or a variant which is at least 70% identical to SEQ ID NO: 26 (also shown in FIG. 2).

```
Exemplary WPRE
                              (SEQ ID NO: 26)
aatcaacctctggattacaaaatttgtgaaagattgactggtatt cttaactatgttgctccttttacgctatgtggatacgctgcttta atgcctttgtatcatgctattgcttcccgtatggctttcattttc tcctccttgtataaatcctggttgctgtctctttatgaggagttg tggcccgttgtcaggcaacgtggcgtggtgtgcactgtgtttgct gacgcaacccccactggttggggcattgccaccacctgtcagctc ctttccgggactttcgctttccccctccctattgccacggcggaa ctcatcgccgcctgccttgcccgctgctggacaggggctcggctg ttgggcactgacaattccgtggtgttgtcggggaaatcatcgtcc tttccttggctgctcgcctgtgttgccacctggattctgcgcggg acgtccttctgctacgtcccttcggccctcaatccagcggacctt ccttcccgcggcctgctgccggctctgcggcctcttccgcgtctt cgccttcgccctcagacgagtcggatctccctttgggccgcctcc ccgc
```

Suitably, the variant may be at least 75%, at least 80%, at least 85%, at least 90%, at least 95%, at least 98%, at least 99% identical to SEQ ID NO: 26.

In some embodiments, the viral vector of the present invention does not comprise a WPRE sequence.

Protein Tag

The COL4A3, COL4A4 or COL4A5 transgene may comprise a protein tag, such as a hemagglutinin (HA) tag. HA can be used as an epitope tag and has been shown not to interfere with bioactivity or biodistribution of proteins to which it has been added. The protein tag can facilitate detection, isolation, and purification of the transgene. Other suitable protein tags may include Myc tags, polyhistidine tags and flag tags.

In some embodiments, the COL4A3, COL4A4 or COL4A5 transgene comprises one or more flag tags. In some embodiments, the COL4A3, COL4A4 or COL4A5 transgene comprises three flag tags.

Kozak Sequence

The viral vector may additionally comprise a Kozak sequence between the promoter and the COL4A3, COL4A4 or COL4A5 transgene. The Kozak sequence is known to play a major role in the initiation of the translation process and can therefore enhance expression of the COL4A3, COL4A4 or COL4A5 transgene. Suitable Kozak sequences will be well known to those of skill in the art.

Suitably, the Kozak sequence may comprise or consist of the nucleotide sequence shown as SEQ ID NO: 27, or a variant which is at least 65% identical to SEQ ID NO: 27.

```
        Exemplary Kozak sequence
                            (SEQ ID NO: 27)
        GCCGCCACCAUGG
```

Suitably, the variant may be at least 75%, at least 85%, or at least 90% identical to SEQ ID NO: 27.

In some embodiments, the viral vector of the present invention does not comprise a Kozak sequence.

Polyadenylation Signal

The viral vector may additionally comprise a polyadenylation signal, such as bovine growth hormone (bGH) polyadenylation signal, e.g. as shown in FIG. 3. Suitably, the polyadenylation signal may be operably linked to the COL4A3, COL4A4, or COL4A5 transgene. Polyadenylation is the addition of a poly(A) tail to a messenger RNA. The poly(A) tail consists of multiple adenosine monophosphates; in other words, it is a stretch of RNA that has only adenine bases. The poly(A) tail is important for the nuclear export, translation, and stability of mRNA. Inclusion of a polyadenylation signal can therefore enhance expression of the COL4A3, COL4A4 or COL4A5 transgene.

Suitable polyadenylation signals include an early SV40 polyadenylation signal (SV40 pA), a chicken beta-globin polyadenylation signal, bovine growth hormone polyadenylation signal (bGH), or a soluble neuropilin-1 polyadenylation signal. In some embodiments, the polyadenylation signal is an early SV40 polyadenylation signal (SV40 pA) or a chicken beta-globin polyadenylation signal. Preferably, the polyadenylation signal is an early SV40 polyadenylation signal (SV40 pA).

Suitably, the polyadenylation signal may comprise or consist of the nucleotide sequence shown as SEQ ID NO: 28, or a variant which is at least 70% identical to SEQ ID NO: 28 (also shown in FIG. 3). Suitably, the variant may be at least 75%, at least 80%, at least 85%, at least 90%, at least 95%, at least 98%, at least 99% identical to SEQ ID NO: 28.

```
Exemplary bGH poly(A) signal sequence
(SEQ ID NO: 28):
ctgtgccttctagttgccagccatctgttgtttgcccctccccg tgccttccttgaccctggaaggtgccactcccactgtcctttcct aataaaatgaggaaattgcatcgcattgtctgagtaggtgtcatt ctattctgggggtggggtggggcaggacagcaaggggaggatt gggaagacaatagcaggcatgctggggatgcggtgggctctatgg
```

Suitably, the polyadenylation signal may comprise or consist of the nucleotide sequence shown as SEQ ID NO: 29, or a variant which is at least 70% identical to SEQ ID NO: 29. Suitably, the variant may be at least 75%, at least 80%, at least 85%, at least 90%, at least 95%, at least 98%, at least 99% identical to SEQ ID NO: 29.

```
        Exemplary soluble neuropilin-1
        polyadenylation signal
        (SEQ ID NO: 29XX):
        aaataaaatacgaaatg
```

Suitably, the polyadenylation signal may comprise or consist of the nucleotide sequence shown as SEQ ID NO: 30, or a variant which is at least 70% identical to SEQ ID NO: 30. Suitably, the variant may be at least 75%, at least 80%, at least 85%, at least 90%, at least 95%, at least 98%, at least 99% identical to SEQ ID NO: 30.

```
        Exemplary SV40pA signal sequence
        (SEQ ID NO: 30):
        aacttgtttattgcagcttataatggttacaaataaagcaatagc atcacaaatttcacaaataaagcatttttttcactgcattctagt tgtggtttgtccaaactcatcaatgtatcttatcatgtctggatc
```

Suitably, the polyadenylation signal may comprise or consist of the nucleotide sequence shown as SEQ ID NO: 41, or a variant which is at least 70% identical to SEQ ID NO: 41. Suitably, the variant may be at least 75%, at least 80%, at least 85%, at least 90%, at least 95%, at least 98%, at least 99% identical to SEQ ID NO: 41.

```
        Exemplary chicken beta-globin
        polyadenylation signal
                            (SEQ ID NO: 41)
        caataaaagatctttattttcattagatctgtgtgttggtttttt gtgtg
```

Inverted Terminal Repeat Sequences

The viral vector may additionally comprise Inverted Terminal Repeat (ITR) sequences at either end of the vector. For example, the vector structure may be, in order: ITR—promotor—transgene (with optional protein tag)—optional WRPE—polyadenylation signal—ITR.

The ITR may act as promoter (Flotte, T. R., et al. 1993. Journal of Biological Chemistry, 268(5), pp. 3781-3790).

Typically, an AAV genome will include at least one inverted terminal repeat sequence (ITR), preferably more than one ITR, such as two ITRs or more. One or more of the ITRs may be derived from AAV genomes having different serotypes, or may be a chimeric or mutant ITR. A preferred mutant ITR is one having a deletion of a trs (terminal resolution site). This deletion allows for continued replication of the genome to generate a single-stranded genome which contains both coding and complementary sequences, i.e. a self-complementary AAV genome. This allows for bypass of DNA replication in the target cell, and so enables accelerated transgene expression. However, the maximum packaging capacity of a scAAV is reduced. Suitably, the AAV genome is not a scAAV genome.

The AAV genome may comprise one or more ITR sequences from any naturally derived serotype, isolate or clade of AAV or a variant thereof. The AAV genome may comprise at least one, such as two, AAV1, AAV2, AAV3, AAV4, AAV5, AAV6, AAV7, AAV8, AAV9, AAV10, or AAV11 ITRs, or variants thereof. Suitably, the AAV genome may comprise at least one, such as two, AAV2 ITRs.

The inclusion of one or more ITRs is preferred to aid concatamer formation of the AAV vector in the nucleus of a host cell, for example following the conversion of single-stranded vector DNA into double-stranded DNA by the action of host cell DNA polymerases. The formation of such episomal concatamers protects the AAV vector during the life of the host cell, thereby allowing for prolonged expression of the transgene in vivo.

Suitably, ITR elements will be the only sequences retained from the native AAV genome in the derivative. A derivative will preferably not include the rep and/or cap genes of the native genome and any other sequences of the native genome. This is preferred for the reasons described above, and also to reduce the possibility of integration of the vector into the host cell genome. Additionally, reducing the size of the AAV genome allows for increased flexibility in incorporating other sequence elements (such as regulatory elements) within the vector in addition to the transgene.

Variants, Derivatives, Analogues, Homologues and Fragments

In addition to the specific proteins and nucleotides mentioned herein, the invention also encompasses variants, derivatives, homologues and fragments thereof.

In the context of the invention, a "variant" of any given sequence is a sequence in which the specific sequence of residues (whether amino acid or nucleic acid residues) has been modified in such a manner that the polypeptide or polynucleotide in question retains at least one of its endogenous functions. A variant sequence can be obtained by addition, deletion, substitution, modification, replacement and/or variation of at least one residue present in the naturally occurring polypeptide or polynucleotide. For example, a variant promoter sequence retains at least some level of the activity and specificity of the promoter sequence from which it is obtained.

The term "derivative" as used herein in relation to proteins or polypeptides of the invention includes any substitution of, variation of, modification of, replacement of, deletion of and/or addition of one (or more) amino acid residues from or to the sequence, providing that the resultant protein or polypeptide retains at least one of its endogenous functions.

Typically, amino acid substitutions may be made, for example from 1, 2 or 3, to 10 or 20 substitutions, provided that the modified sequence retains the required activity or ability. Amino acid substitutions may include the use of non-naturally occurring analogues.

Proteins used in the invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity and/or the amphipathic nature of the residues as long as the endogenous function is retained. For example, negatively charged amino acids include aspartic acid and glutamic acid; positively charged amino acids include lysine and arginine; and amino acids with uncharged polar head groups having similar hydrophilicity values include asparagine, glutamine, serine, threonine and tyrosine.

Conservative substitutions may be made, for example according to the table below. Amino acids in the same block in the second column and preferably in the same line in the third column may be substituted for each other:

| ALIPHATIC | Non-polar | GAP<br>I L V |
| | Polar-uncharged | C S T M<br>N Q |
| | Polar-charged | D E<br>K R H |
| AROMATIC | | F W Y |

The term "homologue" as used herein means a variant having a certain homology with the wild type amino acid sequence or the wild type nucleotide sequence. The term "homology" can be equated with "identity".

In the present context, a homologous sequence is taken to include an amino acid sequence which may be at least 50%, 55%, 65%, 75%, 85% or 90% identical, preferably at least 95%, 96% or 97% or 98% or 99% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 50%, 55%, 65%, 75%, 85% or 90% identical, preferably at least 95%, 96% or 97% or 98% or 99% identical to the subject sequence. Although homology can also be considered in terms of similarity, in the context of the present invention it is preferred to express homology in terms of sequence identity.

Preferably, reference to a sequence which has a percent identity to any one of the SEQ ID NOs detailed herein refers to a sequence which has the stated percent identity over the entire length of the SEQ ID NO referred to.

Homology comparisons can be conducted by eye, or more usually, with the aid of readily available sequence comparison programs. These commercially available computer programs can calculate percent homology or identity between two or more sequences.

Percent homology may be calculated over contiguous sequences, i.e. one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion in the amino acid or nucleotide sequence may cause the following residues or codons to be put out of alignment, thus potentially resulting in a large reduction in percent homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids or nucleotides, a sequence alignment with as few gaps as possible, reflecting higher relatedness between the two compared sequences, will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum percent homology therefore firstly requires the production of an optimal alignment, taking into consideration gap penalties. A suitable computer program for carrying out such an alignment is the GCG Wisconsin Bestfit package (University of Wisconsin, USA; Devereux et al. (1984) Nucleic Acids Research 12: 387). Examples of other software that can perform sequence comparisons include, but are not limited to, the BLAST package (see Ausubel et al. (1999) ibid—Ch. 18), FASTA (Atschul et al. (1990) J. Mol. Biol. 403-410), EMBOSS Needle (Madeira, F., et al., 2019. Nucleic acids research, 47(W1), pp. W636-W641) and the GENEWORKS suite of comparison tools. Both BLAST and FASTA are available for offline and online searching (see Ausubel et al. (1999) ibid, pages 7-58 to 7-60). However, for some applications, it is preferred to use the GCG Bestfit program. Another tool, BLAST 2 Sequences, is also available for comparing protein and nucleotide sequences (FEMS Microbiol. Lett. (1999) 174(2):247-50; FEMS Microbiol. Lett. (1999) 177(1):187-8).

Although the final percent homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix (the default matrix for the BLAST suite of programs). GCG Wisconsin programs generally use either the public default values or a custom symbol comparison table if supplied (see the user manual for further details). For some applications, it is preferred to use the public default values for the GCG package, or in the case of other software, the default matrix, such as BLOSUM62.

Once the software has produced an optimal alignment, it is possible to calculate percent homology, preferably percent sequence identity. The software typically does this as part of the sequence comparison and generates a numerical result. The percent sequence identity may be calculated as the number of identical residues as a percentage of the total residues in the SEQ ID NO referred to.

"Fragments" are also variants and the term typically refers to a selected region of the polypeptide or polynucleotide that is of interest either functionally or, for example, in an assay.

"Fragment" thus refers to an amino acid or nucleic acid sequence that is a portion of a full-length polypeptide or polynucleotide.

Such variants, derivatives, homologues and fragments may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site may be made. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

Cells

In one aspect, the present invention provides a cell comprising the viral vector of the invention. The cell may be an isolated cell. The cell may be a human cell, suitably an isolated human cell.

The viral vector may be introduced into cells using a variety of techniques known in the art, such as transfection, transduction and transformation. Suitably, the vector of the present invention is introduced into the cell by transfection or transduction.

The cell may be any cell type known in the prior art.

Suitably, the cell may be a producer cell. The term "producer cell" includes a cell that produces viral particles, after transient transfection, stable transfection or vector transduction of all the elements necessary to produce the viral particles or any cell engineered to stably comprise the elements necessary to produce the viral particles. Suitable producer cells will be well known to those of skill in the art. Suitable producer cell lines include HEK 293 (e.g. HEK 293T), HeLa, and A549 cell lines.

Suitably, the cell may be a packaging cell. The term "packaging cell" includes a cell which contains some or all of the elements necessary for packaging an infectious recombinant virus. The packaging cell may lack a recombinant viral vector genome. Typically, such packaging cells contain one or more vectors which are capable of expressing viral structural proteins. Cells comprising only some of the elements required for the production of enveloped viral particles are useful as intermediate reagents in the generation of viral particle producer cell lines, through subsequent steps of transient transfection, transduction or stable integration of each additional required element. These intermediate reagents are encompassed by the term "packaging cell". Suitable packaging cells will be well known to those of skill in the art.

Suitably, the cell may be a kidney cell or glomerular cell, for example a podocyte. Suitably, the cell may be an immortalized kidney cell or glomerular cell, for example an immortalized podocyte. Suitable podocyte cell lines will be well known to those of skill in the art, for example CIHP-1. Methods to generate immortalized podocytes will be well known to those of skill in the art. Suitable methods are described in Ni, L., et al., 2012. Nephrology, 17(6), pp. 525-531.

As described above, although the cells have been described by reference to a viral vector, it will be understood that a viral vector gene therapy may alternatively be used.

Methods for Treating or Preventing Alport Syndrome

In one aspect, the present invention provides the viral vector, cell or pharmaceutical composition according to the present invention for use as a medicament.

In one aspect, the present invention provides use of the viral vector, cell or pharmaceutical composition according to the present invention in the manufacture of a medicament.

In one aspect, the present invention provides a method of administering the viral vector, cell or pharmaceutical composition according to the present invention to a subject in need thereof.

In one aspect, the present invention provides the viral vector, cell or pharmaceutical composition according to the present invention for use in preventing or treating Alport syndrome.

In one aspect, the present invention provides use of the viral vector, cell or pharmaceutical composition according to the present invention for the manufacture of a medicament for preventing or treating Alport syndrome.

In one aspect, the present invention provides a method of preventing or treating Alport syndrome comprising administering the viral vector, cell or pharmaceutical composition according to the present invention to a subject in need thereof.

Targeted podocyte viral COL4A3, COL4A4 or COL4A5 gene therapy may change and at least partially normalise the glomerular basement membrane in AS patients. Structural effects of the construct on the glomerular basement membrane may be tested in vitro using a human spheroid model of wild-type and Alport syndrome podocytes. The spheroid models may be examined for changes in the composition of the glomerular basement membrane. Functional testing may also be performed using a nephron on a chip model comprising co-culturing glomerular endothelial cells and podocytes on one side of a channel to develop a mature glomerular basement membrane, which can be used to measure protein permeability via the channels. Constructs may be tested in mouse alpha 3, or alpha 5 KO mice, or an alpha 4 spontaneous mouse mutant. Constructs may be administered by tail vein injection and efficacy will be measured by proteinuria levels and survival.

The viral vector gene therapies of the present invention can be used to treat or prevent Alport syndrome (AS). AS patients typically present with haematuria, which may progress to proteinuria. Haematuria can be determined by the presence of erythrocytes in urine when viewed microscopically. A basal microalbuminuria level of less than 30 mg/day is usually considered non-pathological. Levels of about 30 mg/day to about 300 mg/day are termed microalbuminuria, which is considered pathologic. Albumin levels of over 300 mg/day are termed macroalbuminuria and levels of proteinuria over 3.5 g/day are considered to be nephrotic range proteinuria. Patients treated by the viral vector of the present invention may have haematuria, microalbuminuria, macroalbuminuria or nephrotic range proteinuria.

Treating patients prior to onset of proteinuria may slow or prevent progression of proteinuria and thereby delay or prevent end-stage renal failure. Patients with nephrotic range proteinuria may also be treated. As the collagen IV α345 network of the glomerular basement membrane is changed and normalised or repaired by the transgene, proteinuria levels should be progressively reduced following gene therapy treatment.

The patient may additionally or alternatively test positive for a pathogenic variant of COL4A3, COL4A4 or COL4A5. Pathogenic variants of COL4A3 and COL4A4 can be heterozygous (autosomal dominant), or biallelic (autosomal recessive). Pathogenic variants in COL4A5 are hemizygous or heterozygous (X-linked). The patient is preferably treated with one or more viral vectors comprising a transgene corresponding to the gene(s) for which the patient has a pathogenic variant. For example, a patient having a pathogenic COL4A5 variant can be treated with a viral vector comprising a COL4A5 transgene. The patient may test positive for two or more pathogenic variants of COL4A3, COL4A4 or COL4A5. Such patients may be treated with two or more viral vectors comprising different transgenes, i.e., each viral vector comprising transgenes corresponding to the genes for which the patient has pathogenic variants.

In particular, the patient may have X-chromosome linked AS, which is typically associated with a pathogenic variant of COL4A5.

The term "patient" as used herein may include any mammal, including a human. The patient may be an adult or a paediatric patient, such as a neonate or an infant. The patient may be male or female. The patient may be a male patient with X-chromosome linked AS, particularly an adolescent male patient.

The viral vector, cell or pharmaceutical composition according to the present invention may be administered parenterally, for example, intravenously, or by infusion techniques. The vector, cell or pharmaceutical composition may be administered in the form of a sterile aqueous solution which may contain other substances, for example, enough salts or glucose to make the solution isotonic with blood. The aqueous solution may be suitably buffered (preferably to a pH of from 3 to 9). The pharmaceutical composition may be formulated accordingly. The preparation of suitable parenteral formulations under sterile conditions is readily accomplished by standard pharmaceutical techniques well-known to those skilled in the art.

The viral vector, cell or pharmaceutical may be administered systemically, such as by intravenous injection.

The viral vector, cell or pharmaceutical composition according to the present invention may be administered locally, for example by targeting administration to the kidney. Suitably, the viral vector, cell or pharmaceutical composition may be administered by injection into the renal artery or by ureteral or subcapsular injection. In embodiments of the invention the viral vector may be administered by injection into the renal artery. In alternative embodiments of the invention the viral vector may be administered by retrograde administration, e.g., via the ureters using a urinary catheter.

The viral vector, cell or pharmaceutical composition may be administered as a single dose, in other words, subsequent doses of the vector may not be needed.

In the event that repeated doses are needed different viral serotypes can be used in the vector. For example, vector used in a first dose may comprise AAV-LK03 or AAV-3B whereas the vector used in a subsequent dose may comprise AAV 2/9.

The viral vector, cell or pharmaceutical composition may be administered at varying doses (e.g. measured in vector genomes (vg) per kg). The physician in any event will determine the actual dosage which will be most suitable for any individual subject and it will vary with the age, weight and response of the particular subject. Typically, however, for the AAV vectors of the invention, doses of $10^{10}$ to $10^{14}$ vg/kg, or $10^{11}$ to $10^{13}$ vg/kg may be administered.

Optionally the viral vector, cell or pharmaceutical composition may be administered in combination with temporary immunosuppression of the patient, e.g., by administering the viral vector at the same time as, or following treatment with, oral steroids. Immunosuppression may be desirable before and/or during gene therapy treatment to suppress the patient's immune response to the vector. However, an AAV capsid is present only transiently in the transduced cell as it is not encoded by the vector. The capsid is therefore gradually degraded and cleared, meaning that a short-term immunomodulatory regimen that blocks the immune response to the capsid until capsid sequences are cleared from the transduced cells can allow long-term expression of the transgene.

Immunosuppression may therefore be desirable for a period of about six weeks following administration of the gene therapy.

The viral vector, cell or pharmaceutical composition may additionally or alternatively be administered in combination with a renin-angiotensin treatment strategy, such as an angiotensin converting enzyme (ACE) inhibitor, an aldosterone antagonist (e.g., spironolactone) or an angiotensin receptor blocker (ARB).

Pharmaceutical Composition

The viral vector may be administered in the form of a pharmaceutical composition. In other words the viral vector may be combined with one or more pharmaceutically acceptable carriers, diluents and/or excipients. A suitable pharmaceutical composition is preferably sterile.

Acceptable carriers, diluents, and excipients for therapeutic use are well known in the pharmaceutical art. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s) or solubilising agent(s).

Examples of pharmaceutically acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like.

The pharmaceutical composition may further comprise one or more other therapeutic agents.

The invention further includes the use of kits comprising the viral vector, cells and/or pharmaceutical composition of the present invention. Preferably said kits are for use in the methods and used as described herein, e.g., the therapeutic methods as described herein. Preferably said kits comprise instructions for use of the kit components.

As described above, although the methods for treating or preventing Alport syndrome have been described by reference to a viral vector, it will be understood that a viral vector gene therapy may alternatively be used.

BRIEF DESCRIPTION OF THE DRAWINGS

FIG. 1 shows an example DNA sequence for the minimal human nephrin promoter (NPHS1) (SEQ ID NO: 7).

FIG. 2 shows an example of DNA sequence for a WPRE sequence (SEQ ID NO: 26).

FIG. 3 shows an example DNA sequence for a bGH poly(A) signal sequence (SEQ ID NO: 28).

(A) Schematic for pAAV.265.Col4a3.3¬flag.sv40, an AAV plasmid comprising COL4A3 coupled to mini nephrin promoter. SmaI sites are shown and the following fragments are expected following restriction with SmaI: 1. 6238 bp, 2. 2753 bp, 3. 56 bp, 4. 11 bp, 5. 11 bp. (B) Schematic for pAAV.265.Col4a4.3fl¬ag.sv40, an AAV plasmid comprising COL4A4 coupled to mini nephrin promoter. SmaI sites are shown and the following fragments are expected following restriction with SmaI: 1. 4052 bp, 2. 2753 bp, 3. 2224 bp, 4. 56 bp, 5. 11 bp, 6. 11 bp. (C) Schematic for pAAV.265.Col4a5.3fl¬ag.sv40, an AAV plasmid comprising COL4A5 coupled to mini nephrin promoter. SmaI sites are shown and the following fragments are expected following restriction with SmaI: 1. 4272 bp, 2. 2753 bp, 3. 2032 bp, 4. 56 bp, 5. 11 bp, 6. 11 bp. (D) Restriction digest with SmaI. MW=1 Kb DNA ladder, Lanes 1, 2 and 3 correspond to the digests for plasmids shown in (A), (B), and (C), respectively. (E) Schematic showing restriction digest.

Figure 5:
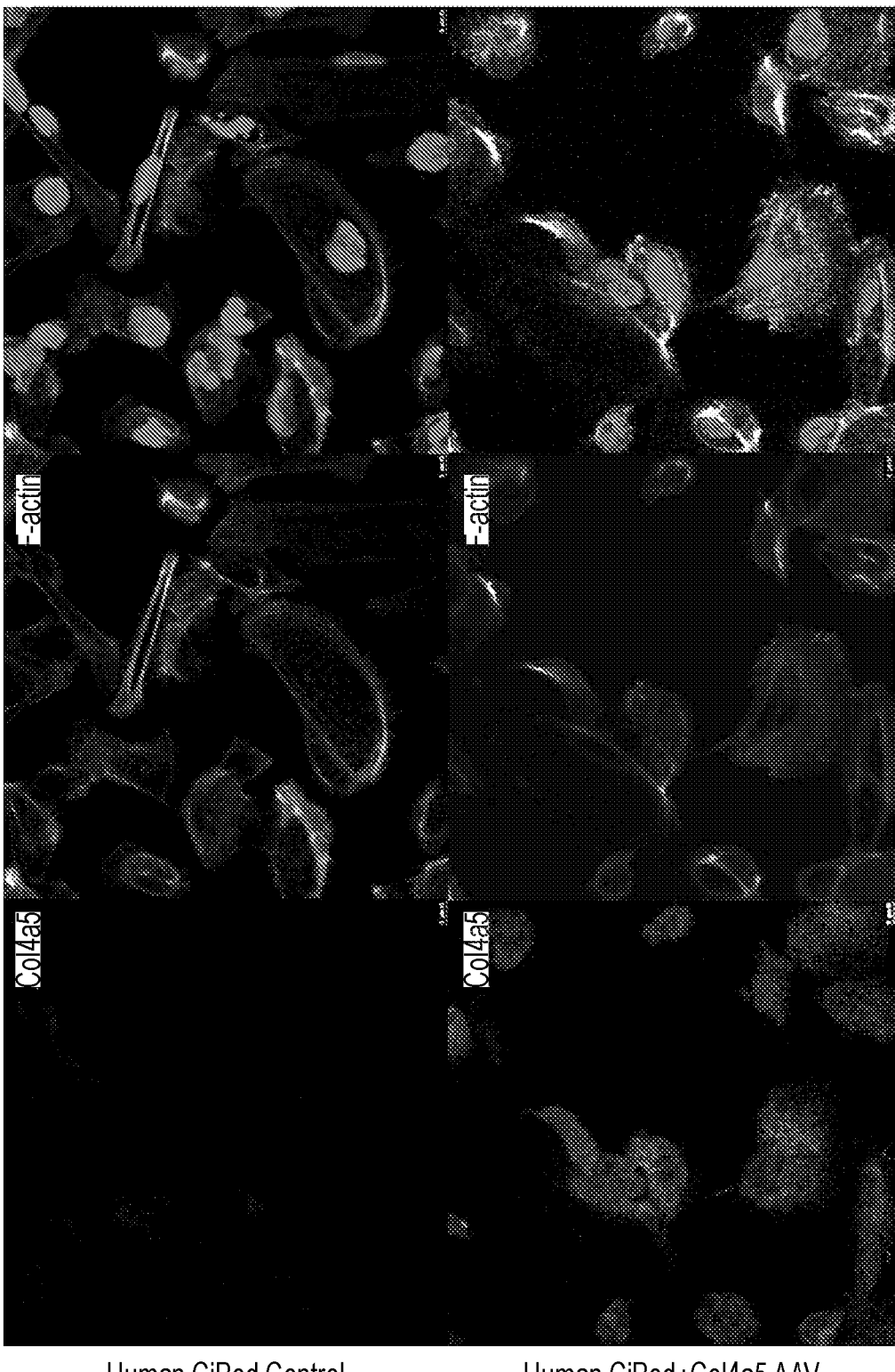

FIG. 5 shows Podocytes transduced with AAV.COL4.nephrin265.Sv40 virus (A) Immunoprecipitation experiments of the full-length FLAG-tagged Col4a3 (LK03) or Col4a5 (LK03) in human differentiated CiPodocytes (conditionally immortalised) pulled down with the anti-FLAG antibody. Anti-FLAG antibody precipitated both Col4a3 and Col4a5. Human-FLAG IgG was used as a control. (B) Western blots of protein lysates showing the expression levels of Col4a3 (LK03 capsid serotype), Col4a5 (LK03) and Col4a5 (2/9 capsid serotype) in human or mouse differentiated CiPodocytes. Non-infected human and mouse Cipodocytes were used as controls. (C) Confocal images showing immunofluorescence staining of transduced Col4a5 in Human wild-type CiPodocytes/Col4a5 3× Flag AAV CiPodocytes with F-Actin. Col4a5 is present at the cytosolic level in the human differentiated podocytes infected with Col4a5 3× Flag AAV virus in comparison to the wild-type counterpart.

FIG. 6 shows a schematic illustration of minimal nephrin promoters (A) The full-length nephrin promoter is 1249 bp in length (excluding the start codon), hereafter referred to as the "FL" nephrin promoter. (B) An exemplary minimal nephrin promoter with the 5' region deleted is 819 bp in length (excluding the start codon), hereafter referred to as the "midi" nephrin promoter. (C) An exemplary minimal nephrin promoter with the 5' region deleted and central region deleted is 265 bp in length (excluding the start codon), hereafter referred to as the "mini" nephrin promoter. (D) The following regions of the nephrin promoter are indicated: (i) human mouse homology region, (ii) retinoic acid receptor (RAR) binding site, (iii) WT1 binding site, (iv) transcription factors binding region, and (v) transcription initiation site.

Figure 7:
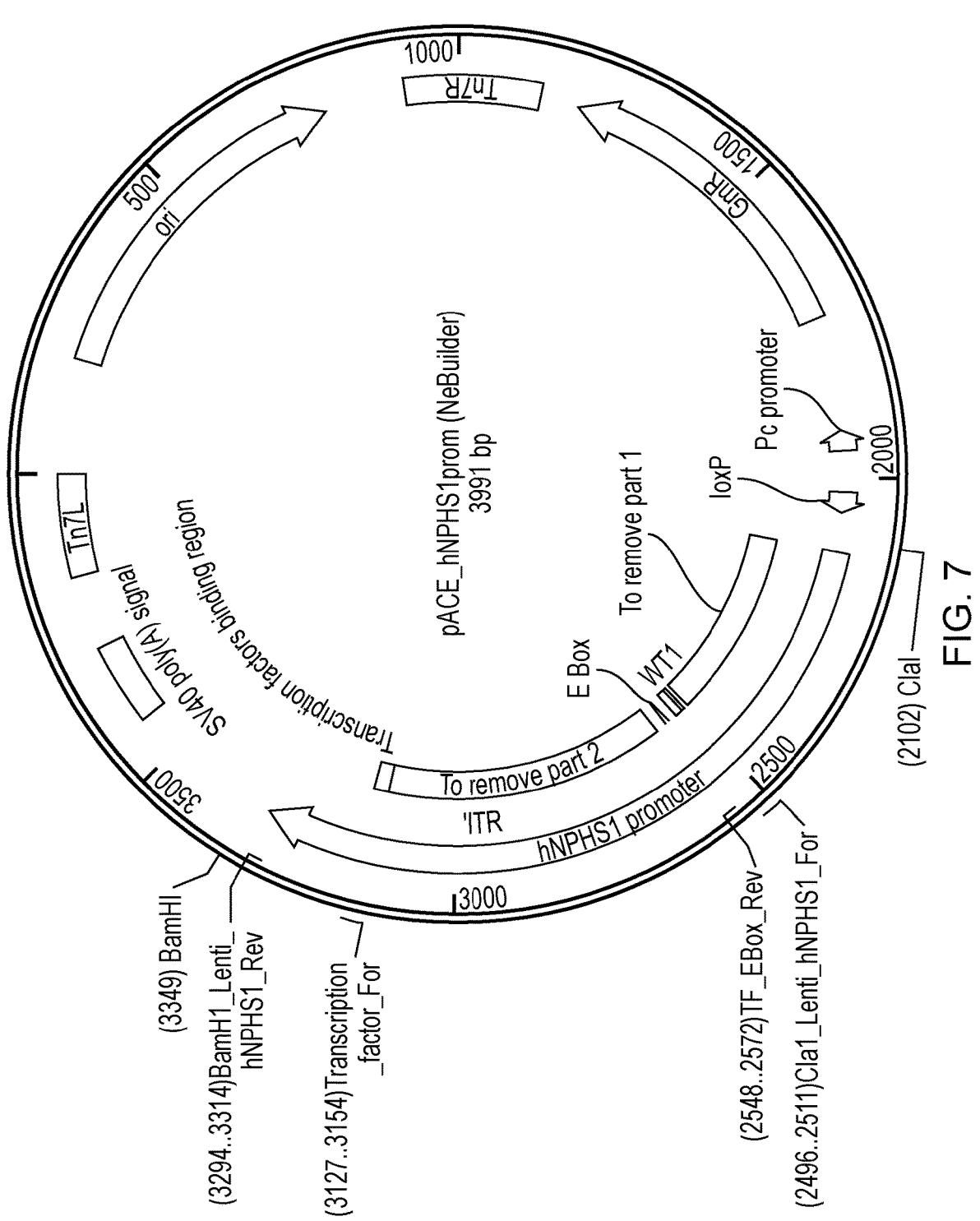
Figure 7:
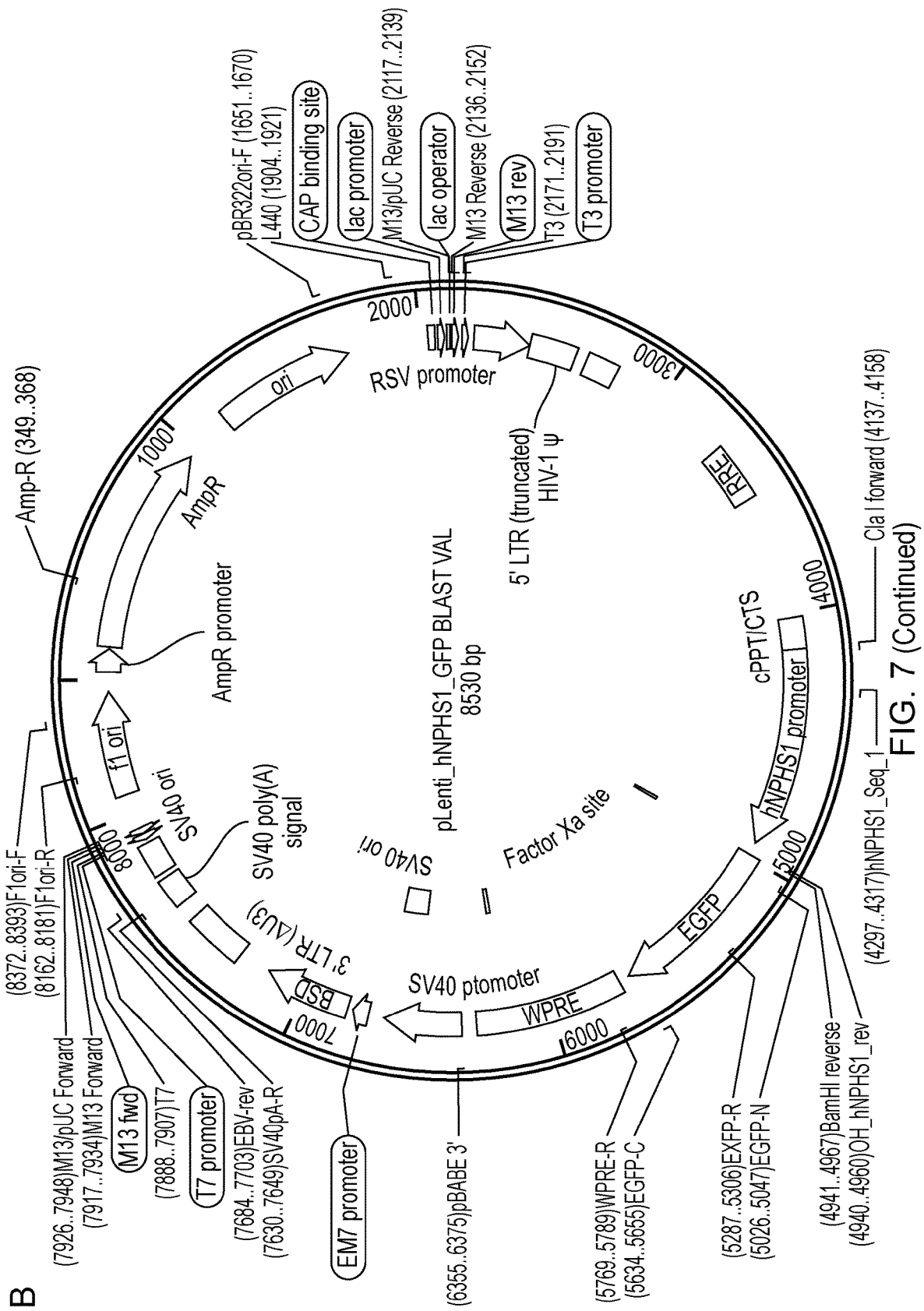

FIG. 7 shows a schematic of a lentiviral vector comprising GFP operably coupled to midi nephrin promoter (A) pACE_hNPHS1 promoter was used as a template, to introduce BamH1 and Cla1 restriction sites. (B) Final construct vector comprising GFP operably coupled to midi nephrin promoter.

Figure 8:
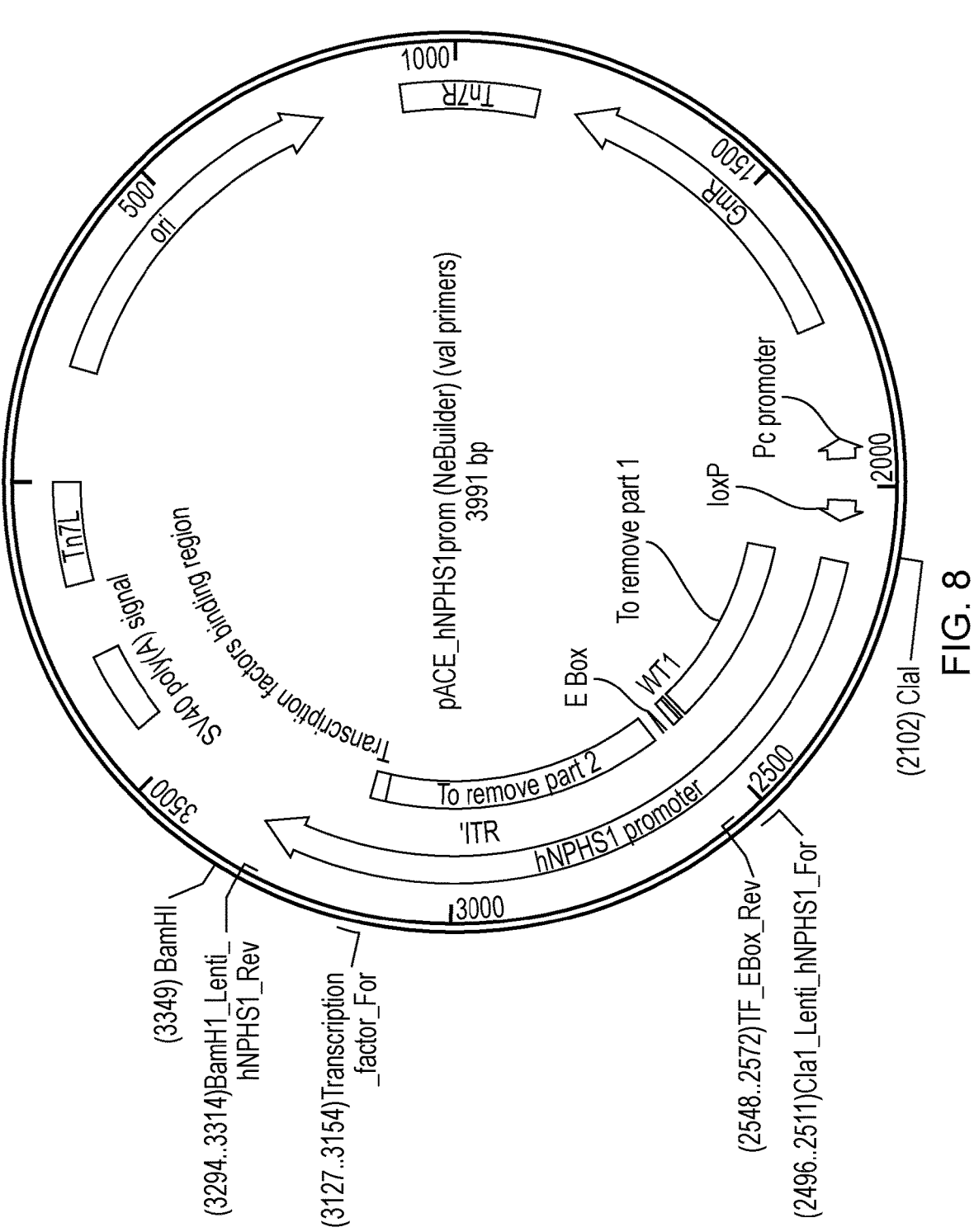
Figure 8:
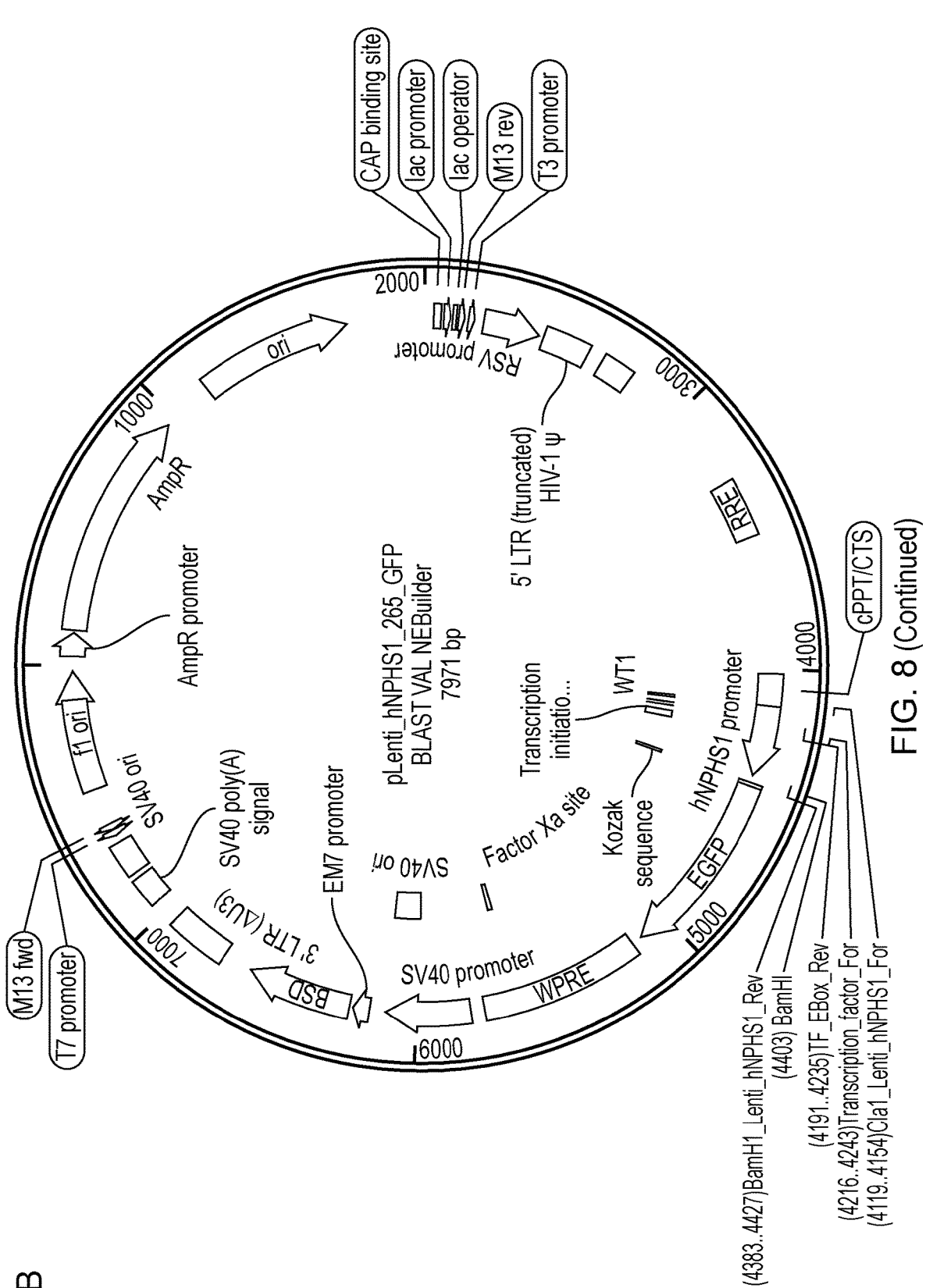

FIG. 8 shows a schematic of a lentiviral vector comprising GFP operably coupled to mini nephrin promoter (A) pACE_hNPHS1 promoter was used as a template to PCR and gel extract the two sections of the promoter. (B) Final construct vector comprising GFP operably coupled to mini nephrin promoter.

FIG. 9 shows expression of GFP in ciPodocytes following transduction with lentiviral vectors Human CiPodocytes stably expressing GFP-tagged nephrin promoters were generated using the lentiviral approach. GFP expression was observed by fluorescence microscopy. (A) Untransduced CiPodocytes. (B) CiPodocytes stably expressing the GFP-tagged mini nephrin promoter. (C) CiPodocytes stably expressing the GFP-tagged FL nephrin promoter.

Figure 10:
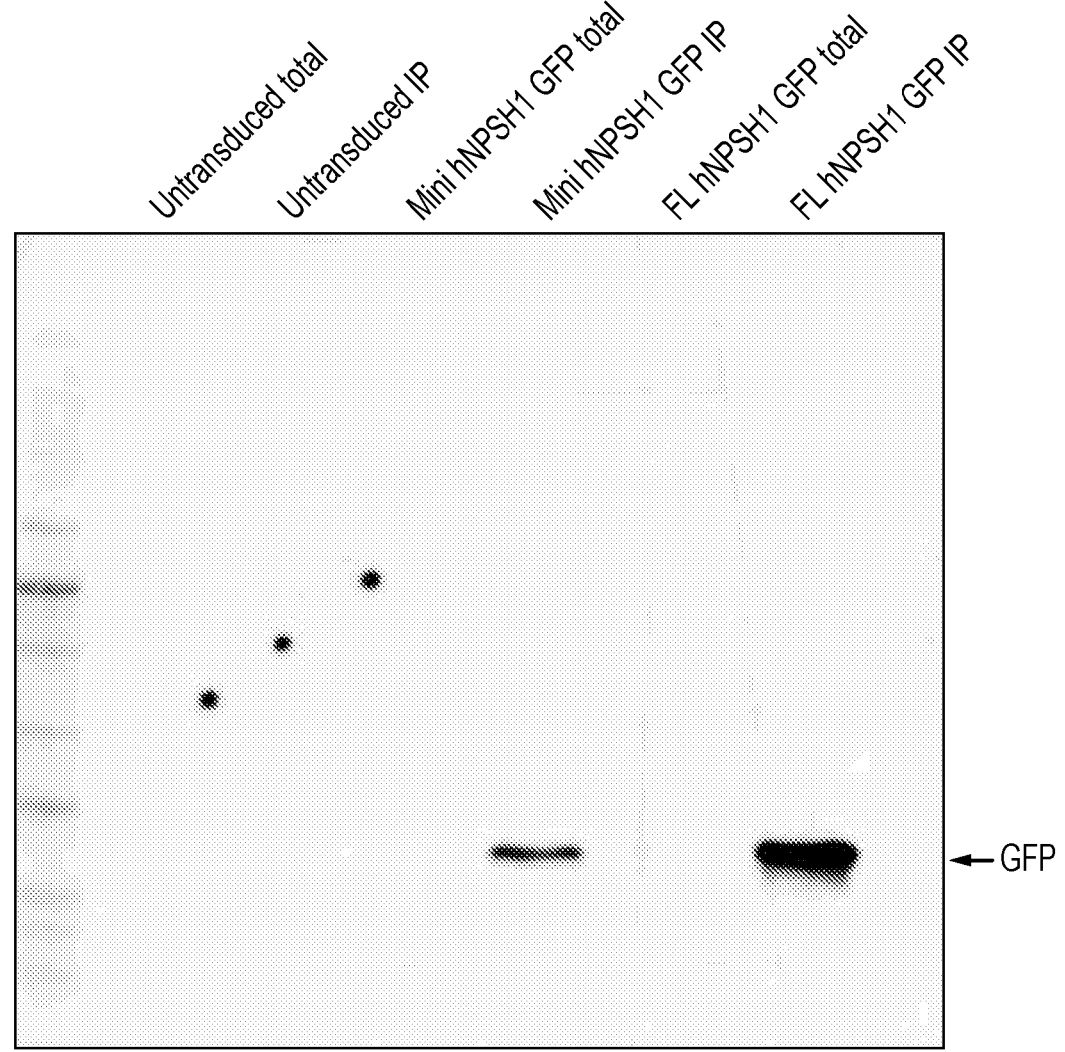

FIG. 10 shows expression of GFP in differentiated ciPodocytes following transduction with lentiviral vectors Lentiviral vectors comprising GFP operably linked to nephrin promoters were transduced into differentiated conditionally immortalised podocytes (ciPodocytes). Immunoprecipitation (IP) was used to detect GFP expression.

Figure 11:
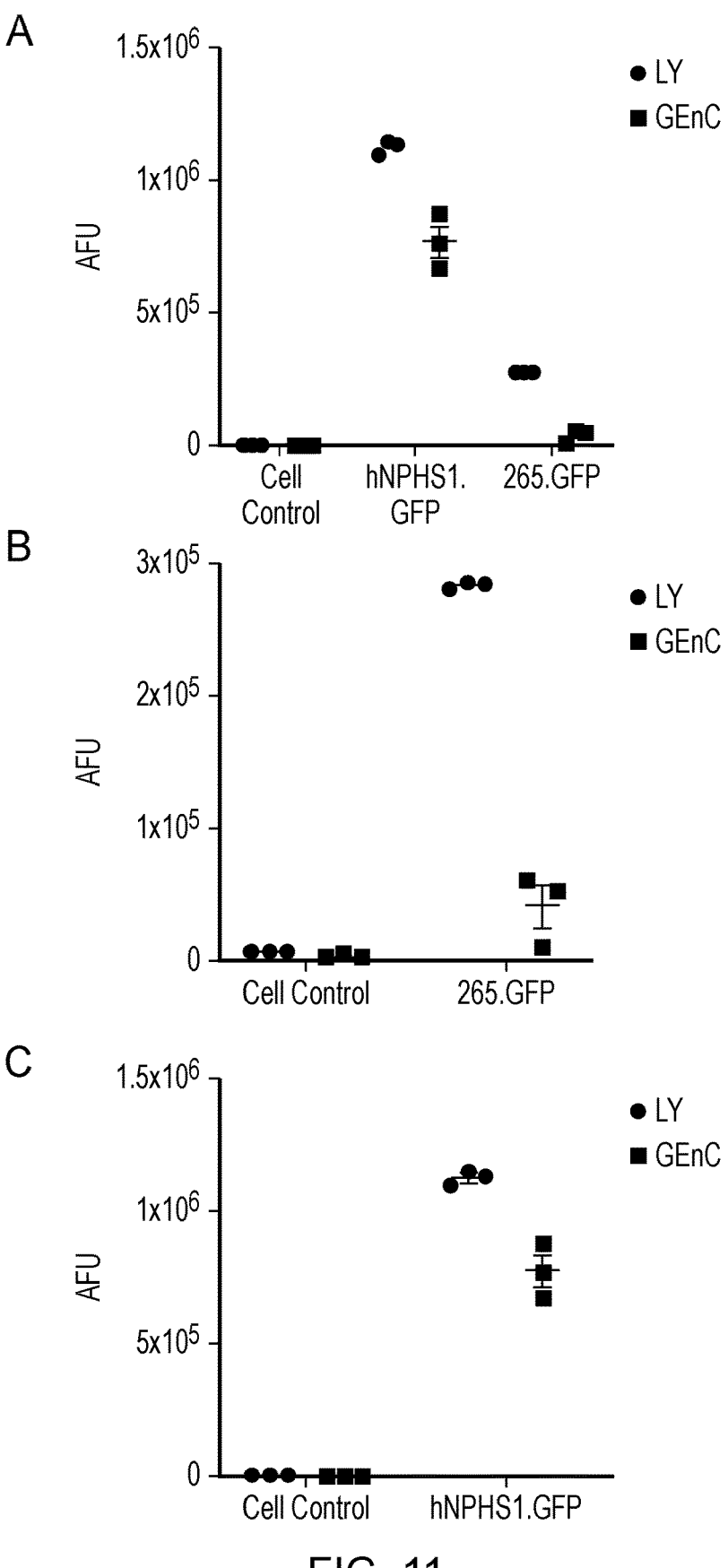

FIG. 11 shows human glomerular cells transduced with Lentivirus—GFP.nephrin promoter (minimal or 265)

FACS analysis displaying median GFP fluorescence (AFU) of all live singlets of conditionally immortalised human podocytes (LY) and glomerular endothelial cells (GEnC) using a Novocyte Analyser. Untransduced cells (Cell Control) were compared with those transduced with lentivirus constructs harbouring a GFP expression cassette controlled by the full length human nephrin promoter (hNPHS1.GFP) or the micro human nephrin promoter (265.GFP). All cells were differentiated for 10 days, trypsinised (100 uL) and diluted in PBS, 2% FBS, 1:1000 DRAQ7 (150 uL). Data and error bars represent 3 technical repeats (100 uL, >2500 cells)±SEM.

EXAMPLES

Alport syndrome, a disease that affects the collagen α3α4α5 (IV) network of the glomerular basement membrane, lacks a glomerular-specific therapeutic strategy. Currently the mainstay of treatment is to target elevated blood pressure. Elevated glomerular filtration rate and microalbuminuria, early indicators of Alport syndrome, are both related to changes in the glomerular basement membrane. Collagen α3α4α5 (IV) is produced by podocytes but not endothelial cells.

The aim of this research is to combine a successful strategy to treat Alport syndrome, with a safe and successful gene delivery approach so that COL4A3, COL4A4 or COL4A5 gene expression can be delivered to podocytes, preferably early in disease and prior to onset of proteinuria.

Example 1—Design, Construction, and Testing of Minimal Nephrin Promoter Coupled to COL4A3, COL4A4, and COL4A5

Design and Construction of AAV Constructs

Figure 4:
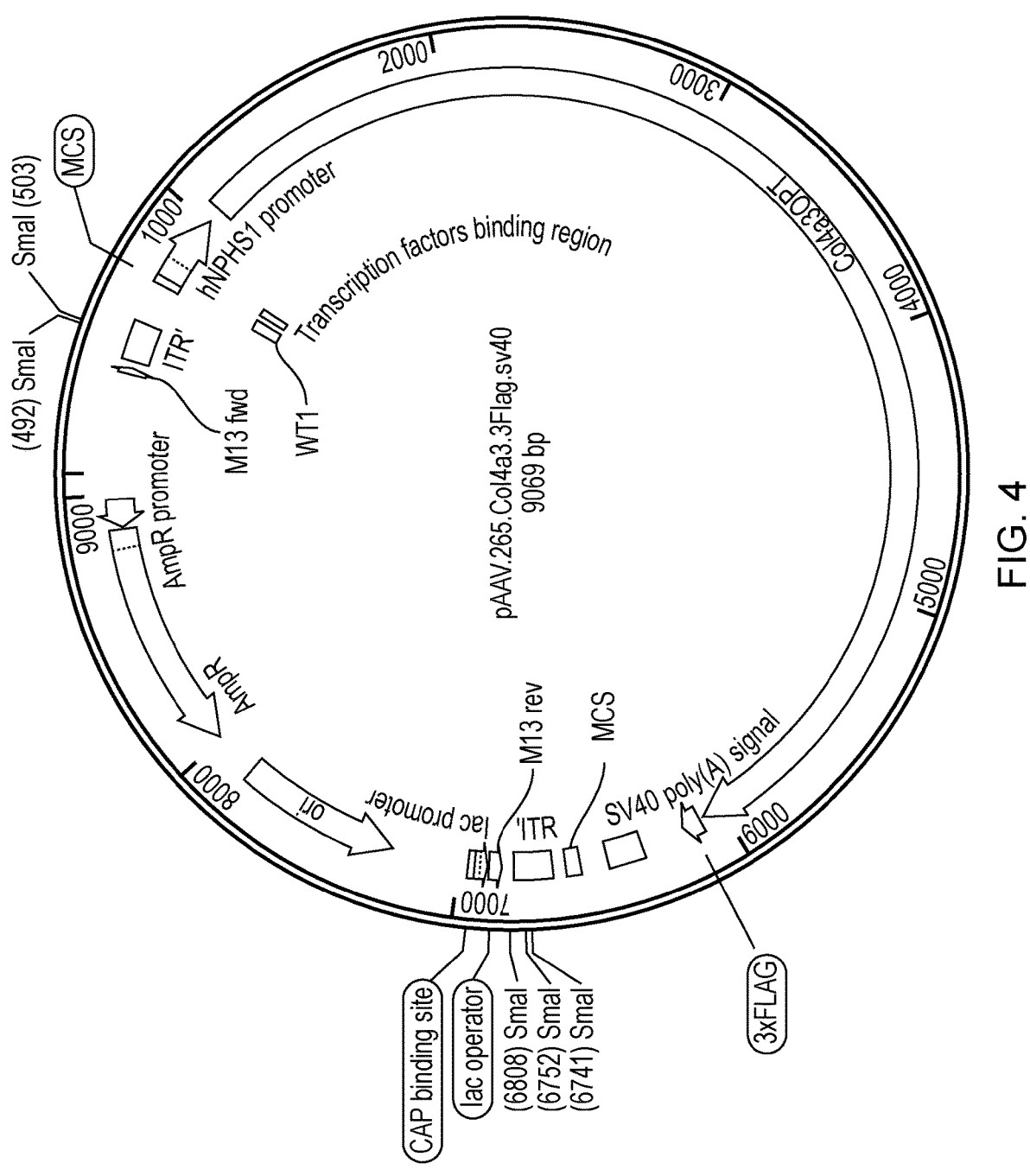
FIG. 4 shows exemplary AAV transfer plasmids comprising COL4A3, COL4A4, and COL4A5 coupled to mini nephrin promoter.
Figure 4:
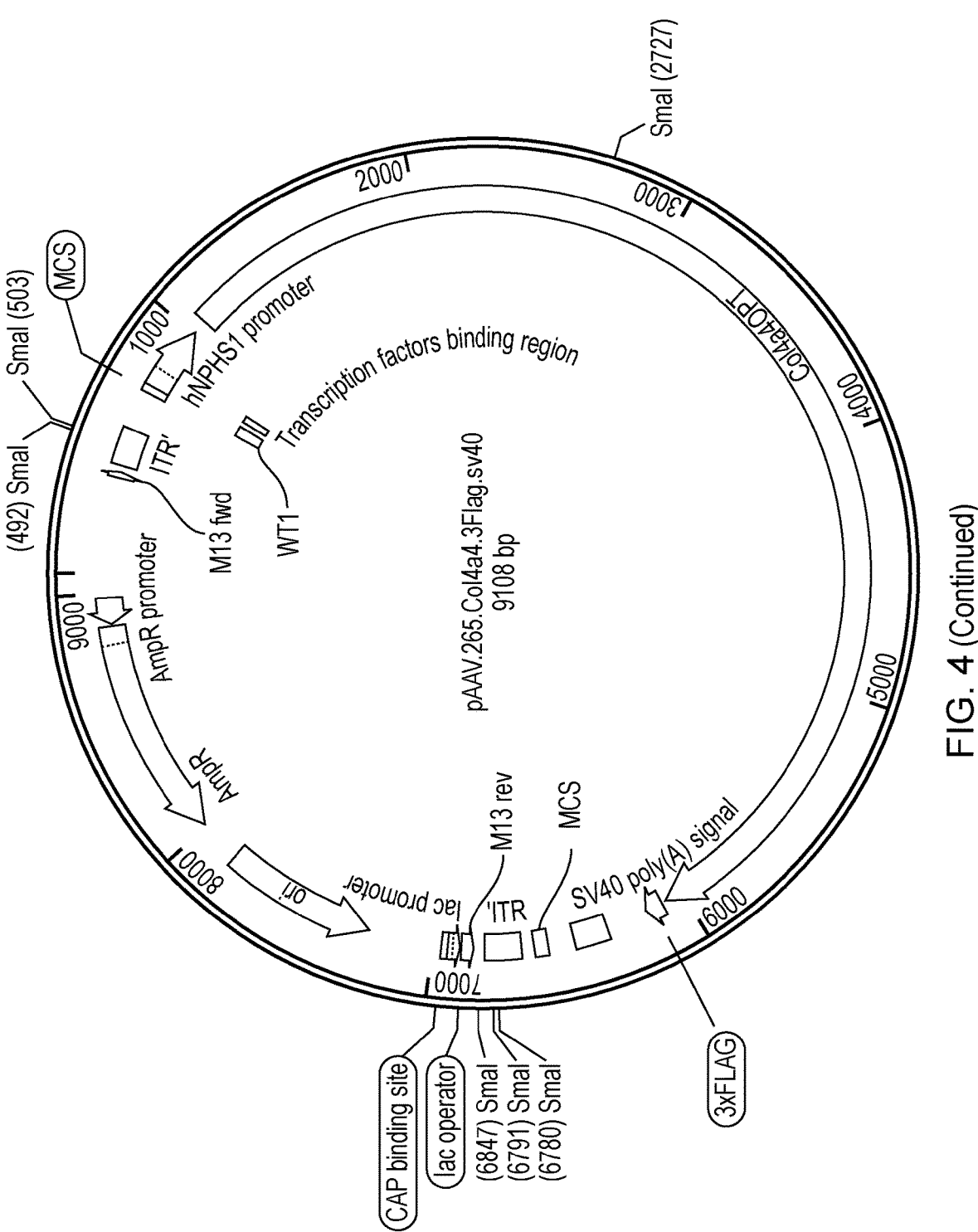
Figure 4:
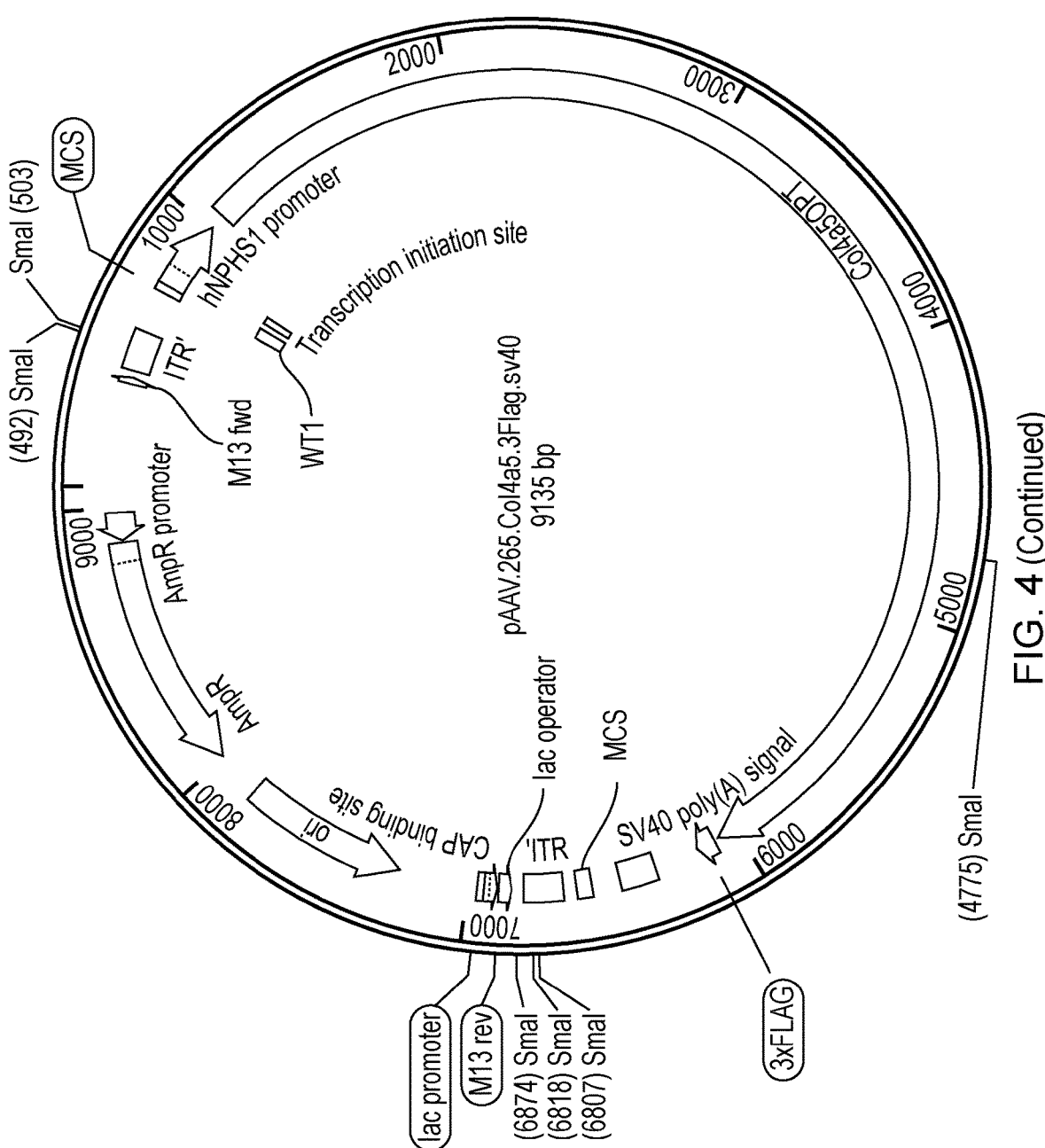

The following AAV transfer plasmids comprising COL4A3, COL4A4, and COL4A5 coupled to the mini nephrin promoter ("265"—see Example 2 for details of design, construction and testing of the mini nephrin promoter) were designed and constructed:

pAAV.265.Col4a3.3flag.sv40, an AAV plasmid comprising COL4A3 coupled to mini nephrin promoter (see FIG. 4A).
  pAAV.265.Col4a4.3flag.sv40, an AAV plasmid comprising COL4A4 coupled to mini nephrin promoter (see FIG. 4B)
  pAAV.265.Col4a5.3flag.sv40, an AAV plasmid comprising COL4A5 coupled to mini nephrin promoter (see FIG. 4C)

A SmaI digestion was performed to confirm that the identity of the plasmids (see FIGS. 4D-E). This shows successful cloning of COL4 a3, a4 and a5 into AAV, with the 265 bp mini nephrin promoter and a SV40 polyA tail.

Testing of AAV Constructs

The following AAV viral vectors were prepared using standard methods:

AAV.COL4A3.nephrin265.Sv40 with LK03 serotype
  AAV.COL4A5.nephrin265.Sv40 with LK03 serotype
  AAV.COL4A5.nephrin265.Sv40 with 2/9 serotype FIG. 5A shows immunoprecipitation experiments of the full-length FLAG-tagged Col4a3 (LK03) or Col4a5 (LK03) in human differentiated ciPodocytes pulled down with the anti-FLAG antibody. Anti-FLAG antibody precipitated both Col4a3 and Col4a5. Human-FLAG IgG was used as a control.

FIG. 5B shows western blots of protein lysates showing the expression levels of Col4a3 (LK03 capsid serotype), Col4a5 (LK03) and Col4a5 (2/9 capsid serotype) in human or mouse differentiated ciPodocytes. Non-infected human and mouse cipodocytes were used as controls.

FIG. 5C shows confocal images showing immunofluorescence staining of transduced Col4a5 in Human wild-type CiPodocytes/Col4a5 3× Flag AAV CiPodocytes with F-Actin. Col4a5 is present at the cytosolic level in the human differentiated podocytes infected with Col4a5 3× Flag AAV virus in comparison to the wild-type counterpart.

These results show that we have unexpectedly successfully transduced human podocytes with COL4a3 and COL4a5 full length coupled to the mini nephrin promoter and that the mini nephrin promoter unexpectedly drives expression of the full length COL4a3 or COL4a5 in the human podocytes.

Example 2—Design, Construction, and Testing of Minimal Nephrin Promoters

Design of Minimal Nephrin Promoters

A human NPHS1 promoter has been described in Moeller et al. 2002 J Am Soc Nephrol, 13(6):1561-7 and Wong M A et al. 2000 Am J Physiol Renal Physiol, 279(6): F1027-32. This NPHS1 promoter is a 1.2 kb fragment and appears to be podocyte-specific. This is referred to hereafter as the "FL" nephrin promoter and is shown in FIG. 6A.

The FL nephrin promoter was initially cut to 822 bp (819 bp excluding start codon) by deleting the N-terminal sequence. This is referred to hereafter as the "midi" nephrin promoter and is shown in FIG. 6B.

The midi nephrin promoter was further cut to 268 bp (265 bp excluding start codon) by removing putative general transcription domains from the central region. This is referred to hereafter as the "mini" nephrin promoter and is shown in FIG. 6C.

Construction of Vector Constructs

Midi Nephrin Promoter pACE_hNPHS1 promoter was used as a template to introduce BamHI and ClaI restriction sites as shown in FIG. 7A. Fragments were then gel extracted and digested with ClaI and BamHI for 1 h at 37° C. prior to ligation into pLenti GFP Blast vector. Ligations were further transformed into stable competent *E. coli* cells, DNA was extracted and sequenced (Midi Promoter). The final lentiviral vector is shown in FIG. 7B.

Mini Nephrin Promoter pACE_hNPHS1 promoter was used to PCR the overhangs (OHs) as shown in FIG. 8A. Two sections of the promoter containing OHs were gel extracted for the NEBuilder HiFi Assembly reaction into pLenti GFP Blast vector. The ligation reaction was then cleaned using the DNA clean up kit, prior to its transformation into stable competent *E. coli* cells. DNA was extracted and sequenced. The final lentiviral vector is shown in FIG. 8B.

51
52

Testing Vector Constructs

The minimal nephrin promotors were used to express GFP in in vitro cell models to check efficacy and podocyte-specificity.

pLenti GFP Blast Nephrin Promoter constructs (Full Length, Midi and Mini) were used to transfect HEK293T cells for 48 h to make virus, which was further used to create human conditionally immortalized podocytes stably expressing either GFP-tagged FL NPHS1, midi or mini promoters.

Conditionally immortalised human podocytes (ciPodocytes) were transfected with the lentiviral vectors to determine whether the minimal promoters were able to drive GFP expression. Both the midi and mini nephrin promoters were shown to drive GFP expression. FIG. 9 shows a representative fluorescence microscopy image showing GFP expression from the mini nephrin promoter. FIG. 10 shows a representative western blot showing GFP expression from the mini nephrin promoter. These results show that the minimal nephrin promoter is able to drive transgene expression in podocytes.

The lentiviral vectors were also used to transduce human glomerular cells. ciPodocytes and glomerular endothelial cells were transduced with a lentivirus comprising GFP coupled to the mini nephrin reporter. FIG. 11A-C shows FACS analysis displaying median GFP fluorescence (AFU) of all live singlets of conditionally immortalised human podocytes (LY) and glomerular endothelial cells (GEnC) using a Novocyte Analyser. Untransduced cells (Cell Control) were compared with those transduced with lentivirus constructs harbouring a GFP expression cassette controlled by the full length human nephrin promoter (hNPHS1.GFP) or the mini human nephrin promoter (265.GFP). All cells were differentiated for 10 days, trypsinised (100 uL) and diluted in PBS, 2% FBS, 1:1000 DRAQ7 (150 uL). Data and error bars represent 3 technical repeats (100 uL, >2500 cells)±SEM. These results show podocyte specificity for the minimal nephrin promoter when compared to glomerular endothelial cells.

Example 3—Podocyte Targeted Gene Therapy

We have developed a targeted gene delivery system in human and mouse podocytes using adeno-associated virus (AAV) (see PCT/GB2020/050097). Using a podocyte-specific promoter (nephrin), AAV serotype 2/9 successfully infected podocytes in vivo, inducing podocin expression. In animals where podocin was knocked down using the Cre-Loxp system (NPHS2fl/fl), resulting in proteinuria, AAV treatment successfully recovered podocin expression and ameliorated proteinuria. In addition, we have shown efficient and specific transduction of GFP by AAV LK03 (with better efficiency than AAV2/9) in human podocytes using the same promoter.

REFERENCES

KODIPPILI K, HAKIM C H, PAN X, YANG H T, YUE Y, ZHANG Y, SHIN J H, YANG N N, DUAN D. Dual AAV Gene Therapy for Duchenne Muscular Dystrophy with a 7-kb Mini-Dystrophin Gene in the Canine Model. Hum Gene Ther. 2018 March; 29(3): 299-311.

LUO, X., HALL, G., L I, S., BIRD, A., LAVIN, P. J., WINN, M. P., KEMPER, A. R., BROWN, T. T. & KOEBERL, D. D. 2011. Hepatorenal correction in murine glycogen storage disease type I with a double-stranded adeno-associated virus vector. Mol Ther, 19, 1961-70.

MCCLEMENTS M E, MACLAREN R E. Adeno-associated Virus (AAV) Dual Vector Strategies for Gene Therapy Encoding Large Transgenes. Yale J Biol Med. 2017 Dec. 19; 90(4):611-623

MOELLER, M. J., SANDEN, S. K., SOOFI, A., WIGGINS, R. C. & HOLZMAN, L. B. 2002. Two gene fragments that direct podocyte-specific expression in transgenic mice. J Am Soc Nephrol, 13, 1561-7.

PICCONI, J. L., MUFF-LUETT, M. A., W U, D., BUNCH-MAN, E., SCHAEFER, F. & BROPHY, P. D. 2014. Kidney-specific expression of GFP by in-utero delivery of pseudotyped adeno-associated virus 9. Molecular Therapy. Methods & Clinical Development, 1, 14014.

ROCCA, C. J., U R, S. N., HARRISON, F. & CHERQUI, S. 2014. rAAV9 combined with renal vein injection is optimal for kidney-targeted gene delivery: conclusion of a comparative study. Gene therapy, 21, 618-628.

SCHAMBACH, A., BOHNE, J., BAUM, C., HERMANN, F. G., EGERER, L., VON LAER, D. & GIROGLOU, T. 2005. Woodchuck hepatitis virus post-transcriptional regulatory element deleted from X protein and promoter sequences enhances retroviral vector titer and expression. Gene Therapy, 13, 641.

SCHIEVENBUSCH, S., STRACK, I., SCHEFFLER, M., NISCHT, R., COUTELLE, O., HOSEL, M., HALLEK, M., FRIES, J. W. U., DIENES, H.-P., ODENTHAL, M. & BUNING, H. 2010. Combined Paracrine and Endocrine AAV9 mediated Expression of Hepatocyte Growth Factor for the Treatment of Renal Fibrosis. Molecular Therapy, 18, 1302-1309.

EMBODIMENTS

Various features and embodiments of the present invention will now be described with reference to the following numbered paragraphs (paras).

1. A viral vector gene therapy, wherein the viral vector comprises:
    a COL4A3, COL4A4 or COL4A5 transgene; and
    an optional podocyte-specific promoter.
2. A viral vector gene therapy according to para 1, wherein the podocyte-specific promoter is minimal nephrin promoter NPHS1 or podocin promoter NPHS2.
3. A viral vector gene therapy according to para 1 or 2, wherein the viral vector is an adeno-associated virus (AAV).
4. A viral vector gene therapy according to para 3, wherein the AAV vector is AAV serotype 2/9, LK03 or 3B.
5. A viral vector gene therapy according to any of paras 1 to 4, wherein the COL4A3, COL4A4 or COL4A5 transgene is a mini-gene.
6. A viral vector gene therapy according to any of paras 1 to 4, wherein the gene therapy comprises:
    a first viral vector comprising at least a portion of a COL4A3, COL4A4 or COL4A5 transgene; and
    an optional a podocyte-specific promoter; and
    a second viral vector comprising at least a portion of a corresponding COL4A3, COL4A4 or COL4A5 transgene; and
    an optional a podocyte-specific promoter.
7. A viral vector gene therapy according to any of paras 1 to 6, wherein the viral vector additionally comprises a Woodchuck hepatitis post-transcriptional regulatory element (WPRE).

8. A viral vector gene therapy according to any of paras 1 to 7, wherein the COL4A3, COL4A4 or COL4A5 transgene is human and/or comprises a hemagglutinin (HA) tag.

9. A viral vector gene therapy according to any of paras 1 to 8, wherein the viral vector additionally comprises a Kozak sequence between the promoter and the COL4A3, COL4A4 or COL4A5 transgene.

10. A viral vector gene therapy according to any of paras 1 to 9, wherein the viral vector additionally comprises a polyadenylation signal such as bovine growth hormone (bGH) polyadenylation signal.

11. A viral vector gene therapy according to any of paras 1 to 10, for use in treating or preventing Alport Syndrome.

12. A viral vector gene therapy for use according to para 11, wherein the viral vector gene therapy is to be administered to a human patient.

13. A viral vector gene therapy for use according to paras 11 or 12, wherein the viral vector gene therapy is to be administered systemically.

14. A viral vector gene therapy for use according to any of paras 11 to 13, wherein the viral vector gene therapy is to be administered by intravenous injection.

15. A viral vector gene therapy for use according to any of paras 11 to 14, wherein the viral vector gene therapy is to be administered by injection into the renal artery.

---

The invention claimed is:

1. A viral vector, wherein the viral vector comprises a COL4A3, COL4A4 or COL4A5 transgene and a podocyte-specific promoter, wherein the podocyte-specific promoter is a minimal nephrin promoter NPHS1, wherein the minimal nephrin promoter NPHS1 comprises the nucleotide sequence shown as SEQ ID NO: 10, or a variant that is at least 70% identical to SEQ ID NO: 10, and wherein the minimal nephrin promoter has a length of about 0.6 kb or less.

2. The viral vector according to claim 1, wherein:

(i) the COL4A3 transgene encodes a COL4A3 polypeptide which comprises an amino acid sequence having at least 70% identity to SEQ ID NO: 1, or a fragment thereof;

(ii) the COL4A4 transgene encodes a COL4A4 polypeptide which comprises an amino acid sequence having at least 70% identity to SEQ ID NO: 2, or a fragment thereof; and/or (iii) the COL4A5 transgene encodes a COL4A5 polypeptide which comprises an amino acid sequence having at least 70% identity to SEQ ID NO: 3, or a fragment thereof.

3. The viral vector according to claim 1, wherein: (i) the COL4A3 transgene encodes a full-length COL4A3 polypeptide; (ii) the COL4A4 transgene encodes a full-length COL4A4 polypeptide; and/or (iii) the COL4A5 transgene encodes a full-length COL4A5 polypeptide.

4. The viral vector according to claim 1, wherein the viral vector is an adeno-associated virus (AAV) vector.

5. The viral vector according to claim 4, wherein the AAV vector is in the form of an AAV vector particle.

6. The viral vector according to claim 5, wherein the AAV vector particle is a podocyte-specific AAV vector particle.

7. The viral vector according to claim 5, wherein the AAV vector particle is AAV serotype 2/9, LK03 or 3B.

8. The viral vector according to claim 1, wherein the COL4A3, COL4A4 or COL4A5 transgene is a mini-gene.

9. The viral vector according to claim 1, wherein the viral vector additionally comprises a Woodchuck hepatitis post-transcriptional regulatory element (WPRE).

10. The viral vector according to claim 1, wherein the viral vector does not comprise Woodchuck hepatitis post-transcriptional regulatory element (WPRE).

11. The viral vector according to claim 1, wherein the COL4A3, COL4A4 or COL4A5 transgene is human.

12. The viral vector according to claim 1, wherein the viral vector additionally comprises a Kozak sequence between the promoter and the COL4A3, COL4A4 or COL4A5 transgene.

13. The viral vector according to claim 1, wherein the viral vector additionally comprises a polyadenylation signal.

14. The viral vector according to claim 13, wherein the polyadenylation signal is an early SV40 polyadenylation signal.

15. The viral vector according to claim 1, wherein the minimal nephrin promoter NPHS1 comprises the nucleotide sequence shown as SEQ ID NO: 10, or a variant which is at least 75 percent identical to SEQ ID NO: 10.

16. The viral vector according to claim 1, wherein the minimal nephrin promoter NPHS1 has a length of 0.5 kb or less.

17. The viral vector according to claim 1, wherein the minimal nephrin promoter NPHS1 consists of the nucleotide sequence shown as SEQ ID NO: 10, or a variant which is at least 70% identical to SEQ ID NO: 10.

18. The viral vector according to claim 1, wherein the minimal nephrin promoter NPHS1 comprises or consists of the nucleotide sequence of SEQ ID NO: 35.

19. A viral vector gene therapy, wherein the gene therapy comprises:

a first viral vector comprising at least a portion of a COL4A3, COL4A4 or COL4A5 transgene; and a second viral vector comprising at least a portion of a corresponding COL4A3, COL4A4 or COL4A5 transgene, wherein the first viral vector is a viral vector as defined in claim 1 and/or the second viral vector is a viral vector as defined in claim 1.

20. The viral vector gene therapy according to claim 5, wherein the first viral vector is an AAV vector and the second viral vector is an AAV vector.

21. The viral vector gene therapy according to claim 20, wherein the first viral vector is in the form of an AAV vector particle encapsidated by LK03 capsid proteins or AAV3B capsid proteins and the second viral vector is in the form of an AAV vector particle encapsidated by LK03 capsid proteins or AAV3B capsid proteins.

22. A method of treating or preventing Alport Syndrome, the method comprising administering a viral vector gene therapy according to claim 19 to a subject in need thereof.

23. The method according to claim 22, wherein the viral vector gene therapy is administered by injection into the renal artery.

24. A method of treating or preventing Alport Syndrome, the method comprising administering a viral vector according to claim 1 to a subject in need thereof.

25. The method according to claim 24, wherein the subject is a human patient.

26. The method according to claim 24, wherein the viral vector is administered systemically.

27. The method according to claim 24, wherein the viral vector is administered by intravenous injection.

28. The method according to claim 24, wherein the viral vector is administered by injection into the renal artery.

* * * * *

SEQUENCE LISTING

<160> NUMBER OF SEQ ID NOS: 41

<210> SEQ ID NO 1
<211> LENGTH: 1670
<212> TYPE: PRT
<213> ORGANISM: Artificial Sequence
<220> FEATURE:
<223> OTHER INFORMATION: exemplary COL4A3 amino acid sequence

<400> SEQUENCE: 1

```
Met Ser Ala Arg Thr Ala Pro Arg Pro Gln Val Leu Leu Leu Pro Leu
1               5                   10                  15

Leu Leu Val Leu Leu Ala Ala Ala Pro Ala Ala Ser Lys Gly Cys Val
                20                  25                  30

Cys Lys Asp Lys Gly Gln Cys Phe Cys Asp Gly Ala Lys Gly Glu Lys
            35                  40                  45

Gly Glu Lys Gly Phe Pro Gly Pro Pro Gly Ser Pro Gly Gln Lys Gly
        50                  55                  60

Phe Thr Gly Pro Glu Gly Leu Pro Gly Pro Gln Gly Pro Lys Gly Phe
65                  70                  75                  80

Pro Gly Leu Pro Gly Leu Thr Gly Ser Lys Gly Val Arg Gly Ile Ser
                85                  90                  95

Gly Leu Pro Gly Phe Ser Gly Ser Pro Gly Leu Pro Gly Thr Pro Gly
            100                 105                 110

Asn Thr Gly Pro Tyr Gly Leu Val Gly Val Pro Gly Cys Ser Gly Ser
            115                 120                 125

Lys Gly Glu Gln Gly Phe Pro Gly Leu Pro Gly Thr Leu Gly Tyr Pro
        130                 135                 140

Gly Ile Pro Gly Ala Ala Gly Leu Lys Gly Gln Lys Gly Ala Pro Ala
145                 150                 155                 160

Lys Glu Glu Asp Ile Glu Leu Asp Ala Lys Gly Asp Pro Gly Leu Pro
                165                 170                 175

Gly Ala Pro Gly Pro Gln Gly Leu Pro Gly Pro Pro Gly Phe Pro Gly
            180                 185                 190

Pro Val Gly Pro Pro Gly Pro Pro Gly Phe Phe Gly Phe Pro Gly Ala
            195                 200                 205

Met Gly Pro Arg Gly Pro Lys Gly His Met Gly Glu Arg Val Ile Gly
        210                 215                 220

His Lys Gly Glu Arg Gly Val Lys Gly Leu Thr Gly Pro Pro Gly Pro
225                 230                 235                 240

Pro Gly Thr Val Ile Val Thr Leu Thr Gly Pro Asp Asn Arg Thr Asp
                245                 250                 255
```

-continued

```
Leu Lys Gly Glu Lys Gly Asp Lys Gly Ala Met Gly Glu Pro Gly Pro
            260             265             270

Pro Gly Pro Ser Gly Leu Pro Gly Glu Ser Tyr Gly Ser Glu Lys Gly
            275             280             285

Ala Pro Gly Asp Pro Gly Leu Gln Gly Lys Pro Gly Lys Asp Gly Val
    290             295             300

Pro Gly Phe Pro Gly Ser Glu Gly Val Lys Gly Asn Arg Gly Phe Pro
305             310             315             320

Gly Leu Met Gly Glu Asp Gly Ile Lys Gly Gln Lys Gly Asp Ile Gly
            325             330             335

Pro Pro Gly Phe Arg Gly Pro Thr Glu Tyr Tyr Asp Thr Tyr Gln Glu
            340             345             350

Lys Gly Asp Glu Gly Thr Pro Gly Pro Pro Gly Pro Arg Gly Ala Arg
            355             360             365

Gly Pro Gln Gly Pro Ser Gly Pro Pro Gly Val Pro Gly Ser Pro Gly
    370             375             380

Ser Ser Arg Pro Gly Leu Arg Gly Ala Pro Gly Trp Pro Gly Leu Lys
385             390             395             400

Gly Ser Lys Gly Glu Arg Gly Arg Pro Gly Lys Asp Ala Met Gly Thr
            405             410             415

Pro Gly Ser Pro Gly Cys Ala Gly Ser Pro Gly Leu Pro Gly Ser Pro
            420             425             430

Gly Pro Pro Gly Pro Pro Gly Asp Ile Val Phe Arg Lys Gly Pro Pro
            435             440             445

Gly Asp His Gly Leu Pro Gly Tyr Leu Gly Ser Pro Gly Ile Pro Gly
    450             455             460

Val Asp Gly Pro Lys Gly Glu Pro Gly Leu Leu Cys Thr Gln Cys Pro
465             470             475             480

Tyr Ile Pro Gly Pro Pro Gly Leu Pro Gly Leu Pro Gly Leu His Gly
            485             490             495

Val Lys Gly Ile Pro Gly Arg Gln Gly Ala Ala Gly Leu Lys Gly Ser
            500             505             510

Pro Gly Ser Pro Gly Asn Thr Gly Leu Pro Gly Phe Pro Gly Phe Pro
            515             520             525

Gly Ala Gln Gly Asp Pro Gly Leu Lys Gly Glu Lys Gly Glu Thr Leu
    530             535             540

Gln Pro Glu Gly Gln Val Gly Val Pro Gly Asp Pro Gly Leu Arg Gly
545             550             555             560

Gln Pro Gly Arg Lys Gly Leu Asp Gly Ile Pro Gly Thr Pro Gly Val
            565             570             575

Lys Gly Leu Pro Gly Pro Lys Gly Glu Leu Ala Leu Ser Gly Glu Lys
            580             585             590

Gly Asp Gln Gly Pro Pro Gly Asp Pro Gly Ser Pro Gly Ser Pro Gly
            595             600             605

Pro Ala Gly Pro Ala Gly Pro Pro Gly Tyr Gly Pro Gln Gly Glu Pro
    610             615             620

Gly Leu Gln Gly Thr Gln Gly Val Pro Gly Ala Pro Gly Pro Pro Gly
625             630             635             640

Glu Ala Gly Pro Arg Gly Glu Leu Ser Val Ser Thr Pro Val Pro Gly
            645             650             655

Pro Pro Gly Pro Pro Gly Pro Pro Gly His Pro Gly Pro Gln Gly Pro
            660             665             670

Pro Gly Ile Pro Gly Ser Leu Gly Lys Cys Gly Asp Pro Gly Leu Pro
```

-continued

```
                675                     680                     685

Gly Pro Asp Gly Glu Pro Gly Ile Pro Gly Ile Gly Phe Pro Gly Pro
    690                     695                     700

Pro Gly Pro Lys Gly Asp Gln Gly Phe Pro Gly Thr Lys Gly Ser Leu
705                     710                     715                     720

Gly Cys Pro Gly Lys Met Gly Glu Pro Gly Leu Pro Gly Lys Pro Gly
                725                     730                     735

Leu Pro Gly Ala Lys Gly Glu Pro Ala Val Ala Met Pro Gly Gly Pro
            740                     745                     750

Gly Thr Pro Gly Phe Pro Gly Glu Arg Gly Asn Ser Gly Glu His Gly
            755                     760                     765

Glu Ile Gly Leu Pro Gly Leu Pro Gly Leu Pro Gly Thr Pro Gly Asn
    770                     775                     780

Glu Gly Leu Asp Gly Pro Arg Gly Asp Pro Gly Gln Pro Gly Pro Pro
785                     790                     795                     800

Gly Glu Gln Gly Pro Pro Gly Arg Cys Ile Glu Gly Pro Arg Gly Ala
                805                     810                     815

Gln Gly Leu Pro Gly Leu Asn Gly Leu Lys Gly Gln Gln Gly Arg Arg
            820                     825                     830

Gly Lys Thr Gly Pro Lys Gly Asp Pro Gly Ile Pro Gly Leu Asp Arg
            835                     840                     845

Ser Gly Phe Pro Gly Glu Thr Gly Ser Pro Gly Ile Pro Gly His Gln
    850                     855                     860

Gly Glu Met Gly Pro Leu Gly Gln Arg Gly Tyr Pro Gly Asn Pro Gly
865                     870                     875                     880

Ile Leu Gly Pro Pro Gly Glu Asp Gly Val Ile Gly Met Met Gly Phe
                885                     890                     895

Pro Gly Ala Ile Gly Pro Pro Gly Pro Pro Gly Asn Pro Gly Thr Pro
            900                     905                     910

Gly Gln Arg Gly Ser Pro Gly Ile Pro Gly Val Lys Gly Gln Arg Gly
            915                     920                     925

Thr Pro Gly Ala Lys Gly Glu Gln Gly Asp Lys Gly Asn Pro Gly Pro
    930                     935                     940

Ser Glu Ile Ser His Val Ile Gly Asp Lys Gly Glu Pro Gly Leu Lys
945                     950                     955                     960

Gly Phe Ala Gly Asn Pro Gly Glu Lys Gly Asn Arg Gly Val Pro Gly
                965                     970                     975

Met Pro Gly Leu Lys Gly Leu Lys Gly Leu Pro Gly Pro Ala Gly Pro
            980                     985                     990

Pro Gly Pro Arg Gly Asp Leu Gly  Ser Thr Gly Asn Pro  Gly Glu Pro
        995                     1000                    1005

Gly Leu  Arg Gly Ile Pro Gly  Ser Met Gly Asn Met  Gly Met Pro
    1010                    1015                    1020

Gly Ser  Lys Gly Lys Arg Gly  Thr Leu Gly Phe Pro  Gly Arg Ala
    1025                    1030                    1035

Gly Arg  Pro Gly Leu Pro Gly  Ile His Gly Leu Gln  Gly Asp Lys
    1040                    1045                    1050

Gly Glu  Pro Gly Tyr Ser Glu  Gly Thr Arg Pro Gly  Pro Pro Gly
    1055                    1060                    1065

Pro Thr  Gly Asp Pro Gly Leu  Pro Gly Asp Met Gly  Lys Lys Gly
    1070                    1075                    1080

Glu Met  Gly Gln Pro Gly Pro  Pro Gly His Leu Gly  Pro Ala Gly
    1085                    1090                    1095
```

-continued

```
Pro Glu  Gly Ala Pro Gly Ser  Pro Gly Ser Pro Gly  Leu Pro Gly
    1100                 1105                 1110

Lys Pro  Gly Pro His Gly Asp  Leu Gly Phe Lys Gly  Ile Lys Gly
    1115                 1120                 1125

Leu Leu  Gly Pro Pro Gly Ile  Arg Gly Pro Pro Gly  Leu Pro Gly
    1130                 1135                 1140

Phe Pro  Gly Ser Pro Gly Pro  Met Gly Ile Arg Gly  Asp Gln Gly
    1145                 1150                 1155

Arg Asp  Gly Ile Pro Gly Pro  Ala Gly Glu Lys Gly  Glu Thr Gly
    1160                 1165                 1170

Leu Leu  Arg Ala Pro Pro Gly  Pro Arg Gly Asn Pro  Gly Ala Gln
    1175                 1180                 1185

Gly Ala  Lys Gly Asp Arg Gly  Ala Pro Gly Phe Pro  Gly Leu Pro
    1190                 1195                 1200

Gly Arg  Lys Gly Ala Met Gly  Asp Ala Gly Pro Arg  Gly Pro Thr
    1205                 1210                 1215

Gly Ile  Glu Gly Phe Pro Gly  Pro Pro Gly Leu Pro  Gly Ala Ile
    1220                 1225                 1230

Ile Pro  Gly Gln Thr Gly Asn  Arg Gly Pro Pro Gly  Ser Arg Gly
    1235                 1240                 1245

Ser Pro  Gly Ala Pro Gly Pro  Pro Gly Pro Pro Gly  Ser His Val
    1250                 1255                 1260

Ile Gly  Ile Lys Gly Asp Lys  Gly Ser Met Gly His  Pro Gly Pro
    1265                 1270                 1275

Lys Gly  Pro Pro Gly Thr Ala  Gly Asp Met Gly Pro  Pro Gly Arg
    1280                 1285                 1290

Leu Gly  Ala Pro Gly Thr Pro  Gly Leu Pro Gly Pro  Arg Gly Asp
    1295                 1300                 1305

Pro Gly  Phe Gln Gly Phe Pro  Gly Val Lys Gly Glu  Lys Gly Asn
    1310                 1315                 1320

Pro Gly  Phe Leu Gly Ser Ile  Gly Pro Pro Gly Pro  Ile Gly Pro
    1325                 1330                 1335

Lys Gly  Pro Pro Gly Val Arg  Gly Asp Pro Gly Thr  Leu Lys Ile
    1340                 1345                 1350

Ile Ser  Leu Pro Gly Ser Pro  Gly Pro Pro Gly Thr  Pro Gly Glu
    1355                 1360                 1365

Pro Gly  Met Gln Gly Glu Pro  Gly Pro Pro Gly Pro  Pro Gly Asn
    1370                 1375                 1380

Leu Gly  Pro Cys Gly Pro Arg  Gly Lys Pro Gly Lys  Asp Gly Lys
    1385                 1390                 1395

Pro Gly  Thr Pro Gly Pro Ala  Gly Glu Lys Gly Asn  Lys Gly Ser
    1400                 1405                 1410

Lys Gly  Glu Pro Gly Pro Ala  Gly Ser Asp Gly Leu  Pro Gly Leu
    1415                 1420                 1425

Lys Gly  Lys Arg Gly Asp Ser  Gly Ser Pro Ala Thr  Trp Thr Thr
    1430                 1435                 1440

Arg Gly  Phe Val Phe Thr Arg  His Ser Gln Thr Thr  Ala Ile Pro
    1445                 1450                 1455

Ser Cys  Pro Glu Gly Thr Val  Pro Leu Tyr Ser Gly  Phe Ser Phe
    1460                 1465                 1470

Leu Phe  Val Gln Gly Asn Gln  Arg Ala His Gly Gln  Asp Leu Gly
    1475                 1480                 1485
```

```
Thr Leu  Gly Ser Cys Leu Gln  Arg Phe Thr Thr Met  Pro Phe Leu
    1490              1495              1500

Phe Cys  Asn Val Asn Asp Val  Cys Asn Phe Ala Ser  Arg Asn Asp
    1505              1510              1515

Tyr Ser  Tyr Trp Leu Ser Thr  Pro Ala Leu Met Pro  Met Asn Met
    1520              1525              1530

Ala Pro  Ile Thr Gly Arg Ala  Leu Glu Pro Tyr Ile  Ser Arg Cys
    1535              1540              1545

Thr Val  Cys Glu Gly Pro Ala  Ile Ala Ile Ala Val  His Ser Gln
    1550              1555              1560

Thr Thr  Asp Ile Pro Pro Cys  Pro His Gly Trp Ile  Ser Leu Trp
    1565              1570              1575

Lys Gly  Phe Ser Phe Ile Met  Phe Thr Ser Ala Gly  Ser Glu Gly
    1580              1585              1590

Thr Gly  Gln Ala Leu Ala Ser  Pro Gly Ser Cys Leu  Glu Glu Phe
    1595              1600              1605

Arg Ala  Ser Pro Phe Leu Glu  Cys His Gly Arg Gly  Thr Cys Asn
    1610              1615              1620

Tyr Tyr  Ser Asn Ser Tyr Ser  Phe Trp Leu Ala Ser  Leu Asn Pro
    1625              1630              1635

Glu Arg  Met Phe Arg Lys Pro  Ile Pro Ser Thr Val  Lys Ala Gly
    1640              1645              1650

Glu Leu  Glu Lys Ile Ile Ser  Arg Cys Gln Val Cys  Met Lys Lys
    1655              1660              1665

Arg His
    1670

<210> SEQ ID NO 2
<211> LENGTH: 1690
<212> TYPE: PRT
<213> ORGANISM: Artificial Sequence
<220> FEATURE:
<223> OTHER INFORMATION: exemplary COL4A4 amino acid sequence

<400> SEQUENCE: 2

Met Trp Ser Leu His Ile Val Leu Met Arg Cys Ser Phe Arg Leu Thr
1               5                  10                  15

Lys Ser Leu Ala Thr Gly Pro Trp Ser Leu Ile Leu Ile Leu Phe Ser
            20                  25                  30

Val Gln Tyr Val Tyr Gly Ser Gly Lys Lys Tyr Ile Gly Pro Cys Gly
        35                  40                  45

Gly Arg Asp Cys Ser Val Cys His Cys Val Pro Glu Lys Gly Ser Arg
    50                  55                  60

Gly Pro Pro Gly Pro Pro Gly Pro Gln Gly Pro Ile Gly Pro Leu Gly
65                  70                  75                  80

Ala Pro Gly Pro Ile Gly Leu Ser Gly Glu Lys Gly Met Arg Gly Asp
                85                  90                  95

Arg Gly Pro Pro Gly Ala Ala Gly Asp Lys Gly Asp Lys Gly Pro Thr
            100                 105                 110

Gly Val Pro Gly Phe Pro Gly Leu Asp Gly Ile Pro Gly His Pro Gly
        115                 120                 125

Pro Pro Gly Pro Arg Gly Lys Pro Gly Met Ser Gly His Asn Gly Ser
    130                 135                 140

Arg Gly Asp Pro Gly Phe Pro Gly Gly Arg Gly Ala Leu Gly Pro Gly
145                 150                 155                 160
```

```
Gly Pro Leu Gly His Pro Gly Glu Lys Gly Glu Lys Gly Asn Ser Val
            165                 170             175

Phe Ile Leu Gly Ala Val Lys Gly Ile Gln Gly Asp Arg Gly Asp Pro
            180                 185             190

Gly Leu Pro Gly Leu Pro Gly Ser Trp Gly Ala Gly Gly Pro Ala Gly
            195                 200             205

Pro Thr Gly Tyr Pro Gly Glu Pro Gly Leu Val Gly Pro Pro Gly Gln
    210                 215             220

Pro Gly Arg Pro Gly Leu Lys Gly Asn Pro Gly Val Gly Val Lys Gly
225                 230                 235                 240

Gln Met Gly Asp Pro Gly Glu Val Gly Gln Gln Gly Ser Pro Gly Pro
            245                 250             255

Thr Leu Leu Val Glu Pro Pro Asp Phe Cys Leu Tyr Lys Gly Glu Lys
            260                 265             270

Gly Ile Lys Gly Ile Pro Gly Met Val Gly Leu Pro Gly Pro Pro Gly
            275                 280             285

Arg Lys Gly Glu Ser Gly Ile Gly Ala Lys Gly Glu Lys Gly Ile Pro
    290                 295             300

Gly Phe Pro Gly Pro Arg Gly Asp Pro Gly Ser Tyr Gly Ser Pro Gly
305                 310                 315                 320

Phe Pro Gly Leu Lys Gly Glu Leu Gly Leu Val Gly Asp Pro Gly Leu
            325                 330             335

Phe Gly Leu Ile Gly Pro Lys Gly Asp Pro Gly Asn Arg Gly His Pro
            340                 345             350

Gly Pro Pro Gly Val Leu Val Thr Pro Pro Leu Pro Leu Lys Gly Pro
            355                 360             365

Pro Gly Asp Pro Gly Phe Pro Gly Arg Tyr Gly Glu Thr Gly Asp Val
    370                 375             380

Gly Pro Pro Gly Pro Pro Gly Leu Leu Gly Arg Pro Gly Glu Ala Cys
385                 390                 395                 400

Ala Gly Met Ile Gly Pro Pro Gly Pro Gln Gly Phe Pro Gly Leu Pro
            405                 410             415

Gly Leu Pro Gly Glu Ala Gly Ile Pro Gly Arg Pro Asp Ser Ala Pro
            420                 425             430

Gly Lys Pro Gly Lys Pro Gly Ser Pro Gly Leu Pro Gly Ala Pro Gly
            435                 440             445

Leu Gln Gly Leu Pro Gly Ser Ser Val Ile Tyr Cys Ser Val Gly Asn
    450                 455             460

Pro Gly Pro Gln Gly Ile Lys Gly Lys Val Gly Pro Pro Gly Gly Arg
465                 470                 475                 480

Gly Pro Lys Gly Glu Lys Gly Asn Glu Gly Leu Cys Ala Cys Glu Pro
            485                 490             495

Gly Pro Met Gly Pro Pro Gly Pro Gly Leu Pro Gly Arg Gln Gly
            500                 505             510

Ser Lys Gly Asp Leu Gly Leu Pro Gly Trp Leu Gly Thr Lys Gly Asp
            515                 520             525

Pro Gly Pro Pro Gly Ala Glu Gly Pro Pro Gly Leu Pro Gly Lys His
    530                 535             540

Gly Ala Ser Gly Pro Pro Gly Asn Lys Gly Ala Lys Gly Asp Met Val
545                 550                 555                 560

Val Ser Arg Val Lys Gly His Lys Gly Glu Arg Gly Pro Asp Gly Pro
            565                 570             575

Pro Gly Phe Pro Gly Gln Pro Gly Ser His Gly Arg Asp Gly His Ala
```

-continued

```
                 580               585               590
Gly Glu Lys Gly Asp Pro Gly Pro Pro Gly Asp His Glu Asp Ala Thr
             595               600               605
Pro Gly Gly Lys Gly Phe Pro Gly Pro Leu Gly Pro Pro Gly Lys Ala
             610               615               620
Gly Pro Val Gly Pro Pro Gly Leu Gly Phe Pro Gly Pro Pro Gly Glu
625               630               635               640
Arg Gly His Pro Gly Val Pro Gly His Pro Gly Val Arg Gly Pro Asp
             645               650               655
Gly Leu Lys Gly Gln Lys Gly Asp Thr Ile Ser Cys Asn Val Thr Tyr
             660               665               670
Pro Gly Arg His Gly Pro Pro Gly Phe Asp Gly Pro Pro Gly Pro Lys
             675               680               685
Gly Phe Pro Gly Pro Gln Gly Ala Pro Gly Leu Ser Gly Ser Asp Gly
             690               695               700
His Lys Gly Arg Pro Gly Thr Pro Gly Thr Ala Glu Ile Pro Gly Pro
705               710               715               720
Pro Gly Phe Arg Gly Asp Met Gly Asp Pro Gly Phe Gly Gly Glu Lys
             725               730               735
Gly Ser Ser Pro Val Gly Pro Pro Gly Pro Pro Gly Ser Pro Gly Val
             740               745               750
Asn Gly Gln Lys Gly Ile Pro Gly Asp Pro Ala Phe Gly His Leu Gly
             755               760               765
Pro Pro Gly Lys Arg Gly Leu Ser Gly Val Pro Gly Ile Lys Gly Pro
             770               775               780
Arg Gly Asp Pro Gly Cys Pro Gly Ala Glu Gly Pro Ala Gly Ile Pro
785               790               795               800
Gly Phe Leu Gly Leu Lys Gly Pro Lys Gly Arg Glu Gly His Ala Gly
             805               810               815
Phe Pro Gly Val Pro Gly Pro Pro Gly His Ser Cys Glu Arg Gly Ala
             820               825               830
Pro Gly Ile Pro Gly Gln Pro Gly Leu Pro Gly Tyr Pro Gly Ser Pro
             835               840               845
Gly Ala Pro Gly Gly Lys Gly Gln Pro Gly Asp Val Gly Pro Pro Gly
             850               855               860
Pro Ala Gly Met Lys Gly Leu Pro Gly Leu Pro Gly Arg Pro Gly Ala
865               870               875               880
His Gly Pro Pro Gly Leu Pro Gly Ile Pro Gly Pro Phe Gly Asp Asp
             885               890               895
Gly Leu Pro Gly Pro Pro Gly Pro Lys Gly Pro Arg Gly Leu Pro Gly
             900               905               910
Phe Pro Gly Phe Pro Gly Glu Arg Gly Lys Pro Gly Ala Glu Gly Cys
             915               920               925
Pro Gly Ala Lys Gly Glu Pro Gly Glu Lys Gly Met Ser Gly Leu Pro
             930               935               940
Gly Asp Arg Gly Leu Arg Gly Ala Lys Gly Ala Ile Gly Pro Pro Gly
945               950               955               960
Asp Glu Gly Glu Met Ala Ile Ile Ser Gln Lys Gly Thr Pro Gly Glu
             965               970               975
Pro Gly Pro Pro Gly Asp Asp Gly Phe Pro Gly Glu Arg Gly Asp Lys
             980               985               990
Gly Thr Pro Gly Met Gln Gly Arg  Arg Gly Glu Pro Gly  Arg Tyr Gly
             995              1000              1005
```

-continued

```
Pro Pro  Gly Phe His Arg Gly  Glu Pro Gly Glu Lys  Gly Gln Pro
    1010             1015             1020

Gly Pro  Pro Gly Pro Pro Gly  Pro Pro Gly Ser Thr  Gly Leu Arg
    1025             1030             1035

Gly Phe  Ile Gly Phe Pro Gly  Leu Pro Gly Asp Gln  Gly Glu Pro
    1040             1045             1050

Gly Ser  Pro Gly Pro Pro Gly  Phe Ser Gly Ile Asp  Gly Ala Arg
    1055             1060             1065

Gly Pro  Lys Gly Asn Lys Gly  Asp Pro Ala Ser His  Phe Gly Pro
    1070             1075             1080

Pro Gly  Pro Lys Gly Glu Pro  Gly Ser Pro Gly Cys  Pro Gly His
    1085             1090             1095

Phe Gly  Ala Ser Gly Glu Gln  Gly Leu Pro Gly Ile  Gln Gly Pro
    1100             1105             1110

Arg Gly  Ser Pro Gly Arg Pro  Gly Pro Pro Gly Ser  Ser Gly Pro
    1115             1120             1125

Pro Gly  Cys Pro Gly Asp His  Gly Met Pro Gly Leu  Arg Gly Gln
    1130             1135             1140

Pro Gly  Glu Met Gly Asp Pro  Gly Pro Arg Gly Leu  Gln Gly Asp
    1145             1150             1155

Pro Gly  Ile Pro Gly Pro Pro  Gly Ile Lys Gly Pro  Ser Gly Ser
    1160             1165             1170

Pro Gly  Leu Asn Gly Leu His  Gly Leu Lys Gly Gln  Lys Gly Thr
    1175             1180             1185

Lys Gly  Ala Ser Gly Leu His  Asp Val Gly Pro Pro  Gly Pro Val
    1190             1195             1200

Gly Ile  Pro Gly Leu Lys Gly  Glu Arg Gly Asp Pro  Gly Ser Pro
    1205             1210             1215

Gly Ile  Ser Pro Pro Gly Pro  Arg Gly Lys Lys Gly  Pro Pro Gly
    1220             1225             1230

Pro Pro  Gly Ser Ser Gly Pro  Pro Gly Pro Ala Gly  Ala Thr Gly
    1235             1240             1245

Arg Ala  Pro Lys Asp Ile Pro  Asp Pro Gly Pro Pro  Gly Asp Gln
    1250             1255             1260

Gly Pro  Pro Gly Pro Asp Gly  Pro Arg Gly Ala Pro  Gly Pro Pro
    1265             1270             1275

Gly Leu  Pro Gly Ser Val Asp  Leu Leu Arg Gly Glu  Pro Gly Asp
    1280             1285             1290

Cys Gly  Leu Pro Gly Pro Pro  Gly Pro Pro Gly Pro  Pro Gly Pro
    1295             1300             1305

Pro Gly  Tyr Lys Gly Phe Pro  Gly Cys Asp Gly Lys  Asp Gly Gln
    1310             1315             1320

Lys Gly  Pro Val Gly Phe Pro  Gly Pro Gln Gly Pro  His Gly Phe
    1325             1330             1335

Pro Gly  Pro Pro Gly Glu Lys  Gly Leu Pro Gly Pro  Pro Gly Arg
    1340             1345             1350

Lys Gly  Pro Thr Gly Leu Pro  Gly Pro Arg Gly Glu  Pro Gly Pro
    1355             1360             1365

Pro Ala  Asp Val Asp Asp Cys  Pro Arg Ile Pro Gly  Leu Pro Gly
    1370             1375             1380

Ala Pro  Gly Met Arg Gly Pro  Glu Gly Ala Met Gly  Leu Pro Gly
    1385             1390             1395
```

-continued

```
Met Arg  Gly Pro Ser Gly Pro  Gly Cys Lys Gly Glu  Pro Gly Leu
    1400             1405              1410

Asp Gly  Arg Arg Gly Val Asp  Gly Val Pro Gly Ser  Pro Gly Pro
    1415             1420              1425

Pro Gly  Arg Lys Gly Asp Thr  Gly Glu Asp Gly Tyr  Pro Gly Gly
    1430             1435              1440

Pro Gly  Pro Pro Gly Pro Ile  Gly Asp Pro Gly Pro  Lys Gly Phe
    1445             1450              1455

Gly Pro  Gly Tyr Leu Gly Gly  Phe Leu Leu Val Leu  His Ser Gln
    1460             1465              1470

Thr Asp  Gln Glu Pro Thr Cys  Pro Leu Gly Met Pro  Arg Leu Trp
    1475             1480              1485

Thr Gly  Tyr Ser Leu Leu Tyr  Leu Glu Gly Gln Glu  Lys Ala His
    1490             1495              1500

Asn Gln  Asp Leu Gly Leu Ala  Gly Ser Cys Leu Pro  Val Phe Ser
    1505             1510              1515

Thr Leu  Pro Phe Ala Tyr Cys  Asn Ile His Gln Val  Cys His Tyr
    1520             1525              1530

Ala Gln  Arg Asn Asp Arg Ser  Tyr Trp Leu Ala Ser  Ala Ala Pro
    1535             1540              1545

Leu Pro  Met Met Pro Leu Ser  Glu Glu Ala Ile Arg  Pro Tyr Val
    1550             1555              1560

Ser Arg  Cys Ala Val Cys Glu  Ala Pro Ala Gln Ala  Val Ala Val
    1565             1570              1575

His Ser  Gln Asp Gln Ser Ile  Pro Pro Cys Pro Gln  Thr Trp Arg
    1580             1585              1590

Ser Leu  Trp Ile Gly Tyr Ser  Phe Leu Met His Thr  Gly Ala Gly
    1595             1600              1605

Asp Gln  Gly Gly Gly Gln Ala  Leu Met Ser Pro Gly  Ser Cys Leu
    1610             1615              1620

Glu Asp  Phe Arg Ala Ala Pro  Phe Leu Glu Cys Gln  Gly Arg Gln
    1625             1630              1635

Gly Thr  Cys His Phe Phe Ala  Asn Lys Tyr Ser Phe  Trp Leu Thr
    1640             1645              1650

Thr Val  Lys Ala Asp Leu Gln  Phe Ser Ser Ala Pro  Ala Pro Asp
    1655             1660              1665

Thr Leu  Lys Glu Ser Gln Ala  Gln Arg Gln Lys Ile  Ser Arg Cys
    1670             1675              1680

Gln Val  Cys Val Lys Tyr Ser
    1685             1690
```

<210> SEQ ID NO 3
<211> LENGTH: 1685
<212> TYPE: PRT
<213> ORGANISM: Artificial Sequence
<220> FEATURE:
<223> OTHER INFORMATION: exemplary COL4A5 amino acid sequence

<400> SEQUENCE: 3

```
Met Lys Leu Arg Gly Val Ser Leu Ala Ala Gly Leu Phe Leu Leu Ala
1               5                  10                  15

Leu Ser Leu Trp Gly Gln Pro Ala Glu Ala Ala Ala Cys Tyr Gly Cys
            20                  25                  30

Ser Pro Gly Ser Lys Cys Asp Cys Ser Gly Ile Lys Gly Glu Lys Gly
        35                  40                  45
```

```
Glu Arg Gly Phe Pro Gly Leu Glu Gly His Pro Gly Leu Pro Gly Phe
    50              55              60

Pro Gly Pro Glu Gly Pro Pro Gly Pro Arg Gly Gln Lys Gly Asp Asp
65              70              75              80

Gly Ile Pro Gly Pro Pro Gly Pro Lys Gly Ile Arg Gly Pro Pro Gly
                85              90              95

Leu Pro Gly Phe Pro Gly Thr Pro Gly Leu Pro Gly Met Pro Gly His
            100             105             110

Asp Gly Ala Pro Gly Pro Gln Gly Ile Pro Gly Cys Asn Gly Thr Lys
        115             120             125

Gly Glu Arg Gly Phe Pro Gly Ser Pro Gly Phe Pro Gly Leu Gln Gly
    130             135             140

Pro Pro Gly Pro Pro Gly Ile Pro Gly Met Lys Gly Glu Pro Gly Ser
145             150             155             160

Ile Ile Met Ser Ser Leu Pro Gly Pro Lys Gly Asn Pro Gly Tyr Pro
                165             170             175

Gly Pro Pro Gly Ile Gln Gly Leu Pro Gly Pro Thr Gly Ile Pro Gly
            180             185             190

Pro Ile Gly Pro Pro Gly Pro Pro Gly Leu Met Gly Pro Pro Gly Pro
            195             200             205

Pro Gly Leu Pro Gly Pro Lys Gly Asn Met Gly Leu Asn Phe Gln Gly
    210             215             220

Pro Lys Gly Glu Lys Gly Glu Gln Gly Leu Gln Gly Pro Pro Gly Pro
225             230             235             240

Pro Gly Gln Ile Ser Glu Gln Lys Arg Pro Ile Asp Val Glu Phe Gln
            245             250             255

Lys Gly Asp Gln Gly Leu Pro Gly Asp Arg Gly Pro Pro Gly Pro Pro
            260             265             270

Gly Ile Arg Gly Pro Pro Gly Pro Pro Gly Gly Glu Lys Gly Glu Lys
            275             280             285

Gly Glu Gln Gly Glu Pro Gly Lys Arg Gly Lys Pro Gly Lys Asp Gly
    290             295             300

Glu Asn Gly Gln Pro Gly Ile Pro Gly Leu Pro Gly Asp Pro Gly Tyr
305             310             315             320

Pro Gly Glu Pro Gly Arg Asp Gly Glu Lys Gly Gln Lys Gly Asp Thr
            325             330             335

Gly Pro Pro Gly Pro Pro Gly Leu Val Ile Pro Arg Pro Gly Thr Gly
            340             345             350

Ile Thr Ile Gly Glu Lys Gly Asn Ile Gly Leu Pro Gly Leu Pro Gly
            355             360             365

Glu Lys Gly Glu Arg Gly Phe Pro Gly Ile Gln Gly Pro Pro Gly Leu
    370             375             380

Pro Gly Pro Pro Gly Ala Ala Val Met Gly Pro Pro Gly Pro Pro Gly
385             390             395             400

Phe Pro Gly Glu Arg Gly Gln Lys Gly Asp Glu Gly Pro Pro Gly Ile
            405             410             415

Ser Ile Pro Gly Pro Pro Gly Leu Asp Gly Gln Pro Gly Ala Pro Gly
            420             425             430

Leu Pro Gly Pro Pro Gly Pro Ala Gly Pro His Ile Pro Pro Ser Asp
            435             440             445

Glu Ile Cys Glu Pro Gly Pro Pro Gly Pro Pro Gly Ser Pro Gly Asp
    450             455             460

Lys Gly Leu Gln Gly Glu Gln Gly Val Lys Gly Asp Lys Gly Asp Thr
```

-continued

```
465                 470                 475                 480

Cys Phe Asn Cys Ile Gly Thr Gly Ile Ser Gly Pro Pro Gly Gln Pro
                485                 490                 495

Gly Leu Pro Gly Leu Pro Gly Pro Pro Gly Ser Leu Gly Phe Pro Gly
            500                 505                 510

Gln Lys Gly Glu Lys Gly Gln Ala Gly Ala Thr Gly Pro Lys Gly Leu
            515                 520                 525

Pro Gly Ile Pro Gly Ala Pro Gly Ala Pro Gly Phe Pro Gly Ser Lys
        530                 535                 540

Gly Glu Pro Gly Asp Ile Leu Thr Phe Pro Gly Met Lys Gly Asp Lys
545                 550                 555                 560

Gly Glu Leu Gly Ser Pro Gly Ala Pro Gly Leu Pro Gly Leu Pro Gly
            565                 570                 575

Thr Pro Gly Gln Asp Gly Leu Pro Gly Leu Pro Gly Pro Lys Gly Glu
            580                 585                 590

Pro Gly Gly Ile Thr Phe Lys Gly Glu Arg Gly Pro Pro Gly Asn Pro
        595                 600                 605

Gly Leu Pro Gly Leu Pro Gly Asn Ile Gly Pro Met Gly Pro Pro Gly
        610                 615                 620

Phe Gly Pro Pro Gly Pro Val Gly Glu Lys Gly Ile Gln Gly Val Ala
625                 630                 635                 640

Gly Asn Pro Gly Gln Pro Gly Ile Pro Gly Pro Lys Gly Asp Pro Gly
            645                 650                 655

Gln Thr Ile Thr Gln Pro Gly Lys Pro Gly Leu Pro Gly Asn Pro Gly
            660                 665                 670

Arg Asp Gly Asp Val Gly Leu Pro Gly Asp Pro Gly Leu Pro Gly Gln
        675                 680                 685

Pro Gly Leu Pro Gly Ile Pro Gly Ser Lys Gly Glu Pro Gly Ile Pro
        690                 695                 700

Gly Ile Gly Leu Pro Gly Pro Pro Gly Pro Lys Gly Phe Pro Gly Ile
705                 710                 715                 720

Pro Gly Pro Pro Gly Ala Pro Gly Thr Pro Gly Arg Ile Gly Leu Glu
            725                 730                 735

Gly Pro Pro Gly Pro Pro Gly Phe Pro Gly Pro Lys Gly Glu Pro Gly
            740                 745                 750

Phe Ala Leu Pro Gly Pro Pro Gly Pro Pro Gly Leu Pro Gly Phe Lys
            755                 760                 765

Gly Ala Leu Gly Pro Lys Gly Asp Arg Gly Phe Pro Gly Pro Pro Gly
        770                 775                 780

Pro Pro Gly Arg Thr Gly Leu Asp Gly Leu Pro Gly Pro Lys Gly Asp
785                 790                 795                 800

Val Gly Pro Asn Gly Gln Pro Gly Pro Met Gly Pro Pro Gly Leu Pro
            805                 810                 815

Gly Ile Gly Val Gln Gly Pro Pro Gly Pro Gly Ile Pro Gly Pro
        820                 825                 830

Ile Gly Gln Pro Gly Leu His Gly Ile Pro Gly Glu Lys Gly Asp Pro
        835                 840                 845

Gly Pro Pro Gly Leu Asp Val Pro Gly Pro Pro Gly Glu Arg Gly Ser
        850                 855                 860

Pro Gly Ile Pro Gly Ala Pro Gly Pro Ile Gly Pro Pro Gly Ser Pro
865                 870                 875                 880

Gly Leu Pro Gly Lys Ala Gly Ala Ser Gly Phe Pro Gly Thr Lys Gly
            885                 890                 895
```

Glu Met Gly Met Met Gly Pro Pro Gly Pro Pro Gly Pro Leu Gly Ile
                900                 905                 910

Pro Gly Arg Ser Gly Val Pro Gly Leu Lys Gly Asp Asp Gly Leu Gln
            915                 920                 925

Gly Gln Pro Gly Leu Pro Gly Pro Thr Gly Glu Lys Gly Ser Lys Gly
        930                 935                 940

Glu Pro Gly Leu Pro Gly Pro Pro Gly Pro Met Asp Pro Asn Leu Leu
945                 950                 955                 960

Gly Ser Lys Gly Glu Lys Gly Glu Pro Gly Leu Pro Gly Ile Pro Gly
                965                 970                 975

Val Ser Gly Pro Lys Gly Tyr Gln Gly Leu Pro Gly Asp Pro Gly Gln
            980                 985                 990

Pro Gly Leu Ser Gly Gln Pro Gly  Leu Pro Gly Pro Pro  Gly Pro Lys
        995                 1000                1005

Gly Asn  Pro Gly Leu Pro Gly  Gln Pro Gly Leu Ile  Gly Pro Pro
    1010                1015                1020

Gly Leu  Lys Gly Thr Ile Gly  Asp Met Gly Phe Pro  Gly Pro Gln
    1025                1030                1035

Gly Val  Glu Gly Pro Pro Gly  Pro Ser Gly Val Pro  Gly Gln Pro
    1040                1045                1050

Gly Ser  Pro Gly Leu Pro Gly  Gln Lys Gly Asp Lys  Gly Asp Pro
    1055                1060                1065

Gly Ile  Ser Ser Ile Gly Leu  Pro Gly Leu Pro Gly  Pro Lys Gly
    1070                1075                1080

Glu Pro  Gly Leu Pro Gly Tyr  Pro Gly Asn Pro Gly  Ile Lys Gly
    1085                1090                1095

Ser Val  Gly Asp Pro Gly Leu  Pro Gly Leu Pro Gly  Thr Pro Gly
    1100                1105                1110

Ala Lys  Gly Gln Pro Gly Leu  Pro Gly Phe Pro Gly  Thr Pro Gly
    1115                1120                1125

Pro Pro  Gly Pro Lys Gly Ile  Ser Gly Pro Pro Gly  Asn Pro Gly
    1130                1135                1140

Leu Pro  Gly Glu Pro Gly Pro  Val Gly Gly Gly Gly  His Pro Gly
    1145                1150                1155

Gln Pro  Gly Pro Pro Gly Glu  Lys Gly Lys Pro Gly  Gln Asp Gly
    1160                1165                1170

Ile Pro  Gly Pro Ala Gly Gln  Lys Gly Glu Pro Gly  Gln Pro Gly
    1175                1180                1185

Phe Gly  Asn Pro Gly Pro Pro  Gly Leu Pro Gly Leu  Ser Gly Gln
    1190                1195                1200

Lys Gly  Asp Gly Gly Leu Pro  Gly Ile Pro Gly Asn  Pro Gly Leu
    1205                1210                1215

Pro Gly  Pro Lys Gly Glu Pro  Gly Phe His Gly Phe  Pro Gly Val
    1220                1225                1230

Gln Gly  Pro Pro Gly Pro Pro  Gly Ser Pro Gly Pro  Ala Leu Glu
    1235                1240                1245

Gly Pro  Lys Gly Asn Pro Gly  Pro Gln Gly Pro Pro  Gly Arg Pro
    1250                1255                1260

Gly Leu  Pro Gly Pro Glu Gly  Pro Pro Gly Leu Pro  Gly Asn Gly
    1265                1270                1275

Gly Ile  Lys Gly Glu Lys Gly  Asn Pro Gly Gln Pro  Gly Leu Pro
    1280                1285                1290

-continued

```
Gly Leu  Pro Gly Leu Lys Gly  Asp Gln Gly Pro Pro  Gly Leu Gln
    1295             1300              1305

Gly Asn  Pro Gly Arg Pro Gly  Leu Asn Gly Met Lys  Gly Asp Pro
    1310             1315              1320

Gly Leu  Pro Gly Val Pro Gly  Phe Pro Gly Met Lys  Gly Pro Ser
    1325             1330              1335

Gly Val  Pro Gly Ser Ala Gly  Pro Glu Gly Glu Pro  Gly Leu Ile
    1340             1345              1350

Gly Pro  Pro Gly Pro Pro Gly  Leu Pro Gly Pro Ser  Gly Gln Ser
    1355             1360              1365

Ile Ile  Ile Lys Gly Asp Ala  Gly Pro Pro Gly Ile  Pro Gly Gln
    1370             1375              1380

Pro Gly  Leu Lys Gly Leu Pro  Gly Pro Gln Gly Pro  Gln Gly Leu
    1385             1390              1395

Pro Gly  Pro Thr Gly Pro Pro  Gly Asp Pro Gly Arg  Asn Gly Leu
    1400             1405              1410

Pro Gly  Phe Asp Gly Ala Gly  Gly Arg Lys Gly Asp  Pro Gly Leu
    1415             1420              1425

Pro Gly  Gln Pro Gly Thr Arg  Gly Leu Asp Gly Pro  Pro Gly Pro
    1430             1435              1440

Asp Gly  Leu Gln Gly Pro Pro  Gly Pro Pro Gly Thr  Ser Ser Val
    1445             1450              1455

Ala His  Gly Phe Leu Ile Thr  Arg His Ser Gln Thr  Thr Asp Ala
    1460             1465              1470

Pro Gln  Cys Pro Gln Gly Thr  Leu Gln Val Tyr Glu  Gly Phe Ser
    1475             1480              1485

Leu Leu  Tyr Val Gln Gly Asn  Lys Arg Ala His Gly  Gln Asp Leu
    1490             1495              1500

Gly Thr  Ala Gly Ser Cys Leu  Arg Arg Phe Ser Thr  Met Pro Phe
    1505             1510              1515

Met Phe  Cys Asn Ile Asn Asn  Val Cys Asn Phe Ala  Ser Arg Asn
    1520             1525              1530

Asp Tyr  Ser Tyr Trp Leu Ser  Thr Pro Glu Pro Met  Pro Met Ser
    1535             1540              1545

Met Gln  Pro Leu Lys Gly Gln  Ser Ile Gln Pro Phe  Ile Ser Arg
    1550             1555              1560

Cys Ala  Val Cys Glu Ala Pro  Ala Val Val Ile Ala  Val His Ser
    1565             1570              1575

Gln Thr  Ile Gln Ile Pro His  Cys Pro Gln Gly Trp  Asp Ser Leu
    1580             1585              1590

Trp Ile  Gly Tyr Ser Phe Met  Met His Thr Ser Ala  Gly Ala Glu
    1595             1600              1605

Gly Ser  Gly Gln Ala Leu Ala  Ser Pro Gly Ser Cys  Leu Glu Glu
    1610             1615              1620

Phe Arg  Ser Ala Pro Phe Ile  Glu Cys His Gly Arg  Gly Thr Cys
    1625             1630              1635

Asn Tyr  Tyr Ala Asn Ser Tyr  Ser Phe Trp Leu Ala  Thr Val Asp
    1640             1645              1650

Val Ser  Asp Met Phe Ser Lys  Pro Gln Ser Glu Thr  Leu Lys Ala
    1655             1660              1665

Gly Asp  Leu Arg Thr Arg Ile  Ser Arg Cys Gln Val  Cys Met Lys
    1670             1675              1680

Arg Thr
```

-continued

1685

<210> SEQ ID NO 4
<211> LENGTH: 5013
<212> TYPE: DNA
<213> ORGANISM: Artificial Sequence
<220> FEATURE:
<223> OTHER INFORMATION: exemplary COL4A3 transgene sequence

<400> SEQUENCE: 4

```
atgagcgccc ggaccgcccc caggccgcag gtgctcctgc tgccgctcct gctggtgctc          60
ctggcggcgg cgcccgcagc cagcaagggt tgtgtctgta aagacaaagg ccagtgcttc         120
tgtgacgggg ccaaagggga gaagggggag aagggctttc ctggacccc cggttctcct         180 ggccagaaag gattcacagg tcctgaaggc ttgcctggac cgcagggacc caagggcttt         240
ccaggacttc caggactcac gggttccaaa ggtgtaaggg gaataagtgg attgccagga         300
ttttctggtt ctcctggact tccaggcacc ccaggcaata ccgggcctta cggacttgtc         360
ggtgtaccag gatgcagtgg ttctaagggt gagcaggggt ttccaggact cccagggaca         420
ctgggctacc cagggatccc gggtgctgct ggtttgaaag acaaaaggg tgctcctgct         480 aaagaagaag atatagaact tgatgcaaaa ggcgacccgg ggttgccagg ggctccagga         540
ccccagggtt tgccaggccc tccaggtttt cctgggcctg ttggcccacc tggtcctccg         600
ggattctttg gctttccagg agccatggga cctagaggac ctaagggtca catgggtgaa         660
agagtgatag gacataaagg agagcggggt gtgaaagggt taacaggacc cccgggacca         720
ccaggaacag ttattgtgac cctaactggc ccagataaca gaacgacct caaggggaa          780 aagggagaca agggagcaat gggcgagcct ggacctcctg gaccctcagg actgcctgga         840
gaatcatatg gatctgaaaa gggtgctcct ggagaccctg gcctgcaggg aaaacccgga         900
aaagatggtg ttcctggctt ccctggaagt gagggagtca agggcaacag gggtttccct         960
gggttaatgg gtgaagatgg cattaaggga cagaaagggg acattggccc tccaggattt        1020
cgtggtccaa cagaatatta tgacacatac caggaaaagg gagatgaagg cactccaggc        1080
ccaccagggc ccagaggagc tcgtggccca caaggtccca gtggtccccc cggagttcct        1140
ggaagtcctg gatcatcaag gcctggcctc agaggagccc ctggatggcc aggcctgaaa        1200
ggaagtaaag gggaacgagg ccgcccagga aaggatgcca tggggactcc tgggtcccca        1260
ggttgtgctg gttcaccagg tcttccagga tcaccgggac ctccaggacc gccaggtgac        1320
atcgtttttc gcaagggtcc acctggagat cacggactgc caggctatct agggtctcca        1380
ggaatcccag gagttgatgg gcccaaagga gaaccaggcc tcctgtgtac acagtgccct        1440
tatatcccag ggcctccgg tctcccagga ttgccaggt acatggtgt aaaaggaatc          1500 ccaggaagac aaggcgcagc tggcttgaaa ggaagcccag ggtccccagg aaatacaggt        1560
cttccaggat ttccaggttt cccaggtgcc caggtgacc caggacttaa aggagaaaaa         1620
ggtgaaacac ttcagcctga ggggcaagtg ggtgtcccag gtgacccggg gctcagaggc        1680
caacctggga gaaagggctt ggatggaatt cctggaactc cgggagtgaa aggattacca        1740
ggacctaaag gcgaactggc tctgagtggt gagaaagggg accaaggtcc tccaggggat        1800
cctggctccc ctgggtcccc aggacctgca ggaccagctg gaccacctgg ctacggaccc        1860
caaggagaac ctggtctcca gggcacgcaa ggagttcctg agcccccgg accaccggga        1920 gaagccggcc ctagggggaga gctcagtgtt tcaacaccag ttccaggccc accaggacct        1980
ccagggcccc ctggccatcc tggccccaa ggtccacctg gtatccctgg atccctgggg        2040
```

```
aaatgtggag atcctggtct tccagggcct gatggtgaac caggaattcc aggaattgga   2100
tttcctgggc ctcctggacc taagggagac caaggttttc caggtacaaa aggatcactg   2160
ggttgtcctg gaaaaatggg agagcctggg ttacctggaa agccaggcct cccaggagcc   2220
aagggagaac cagcagtagc catgcctgga ggaccaggaa caccaggttt tccaggagaa   2280
agaggcaatt ctggggaaca tggagaaatt ggactccctg gacttccagg tctccctgga   2340
actccaggaa atgaagggct tgatggacca cgaggagatc cagggcagcc tggaccacct   2400
ggagaacaag gaccccccagg aaggtgcata gagggtccca ggggagccca aggacttcca   2460
ggcttaaatg gattgaaagg gcaacaaggc agaagaggta aaacggggcc aaagggagac   2520
ccaggaattc caggcttgga tagatcagga tttcctggag aaactggatc accaggaatt   2580
ccaggtcatc aaggtgaaat gggaccactg ggtcaaagag gatatccagg aaatccggga   2640
attttagggc caccaggtga agatggagtg attgggatga tgggctttcc tggagccatt   2700
ggccctccag ggccccctgg gaacccaggc acaccagggc agagggggag ccctggaatt   2760
ccaggagtaa agggccagag aggaaccccca ggagccaagg gggaacaagg agataaagga   2820
aatcccgggc cttcagagat atcccacgta ataggggaca aaggagaacc aggtctcaaa   2880
ggattcgcag gaaatccagg tgagaaagga aacagaggcg ttccagggat gccaggttta   2940
aagggcctca aaggactacc cggaccagca ggaccaccag gccccagagg agatttgggc   3000
agcactggga atcctggaga accaggactg cgtggtatac caggaagcat ggggaacatg   3060
ggcatgccag gttctaaagg aaaaagggga actttgggat tcccaggtcg agcaggaaga   3120
ccaggcctcc caggtattca tggtctccag ggagataagg gagagccagg ttattcagaa   3180
ggtacaaggc caggaccacc gggaccaacg ggggatccag gactgccggg tgatatggga   3240
aagaaaggag aaatggggca acctggccca cctggacatt tggggcctgc tggacctgag   3300
ggagcccctg gaagtcctgg aagtcctggc ctcccaggaa agccaggtcc tcatggtgat   3360
ttgggtttta aaggaatcaa aggcctcctg ggccctccag gaatcagagg ccctccaggt   3420
cttccaggat ttccaggatc tcctggacca atgggtataa gaggtgacca aggacgtgat   3480
ggaattcctg gtcagccggg agaaaaggga gaaacgggtt tattgagggc ccctccaggc   3540
ccaagaggga accctggtgc tcaaggagcc aaaggagaca ggggagcccc aggtttttcct   3600 ggcctcccgg gcagaaaagg ggccatggga gatgctggac tcgaggacc cacaggcata   3660 gaaggattcc cagggccacc aggtctgccc ggtgcaatta ccctggcca gacaggaaat   3720 cgtggtccac caggctcaag aggaagccca ggtgcgcctg gtcccctgg acctccaggg   3780 agtcatgtaa taggcataaa aggagacaaa gggtctatgg ccaccctgg cccaaaaggt   3840 ccacctggaa ctgcaggaga catgggacca ccaggtcgtc tgggagcacc aggtactcca   3900
ggtcttccag acccagagg tgatcctgga ttccaggggt ttccaggcgt gaaaggagaa   3960
aagggtaatc ctggatttct aggatccatt ggacctccag gaccaattgg gccaaaagga   4020
ccacctggtg tacgtggaga ccctggcaca cttaagatta tctcccttcc aggaagccca   4080
gggccacctg gcacacctgg agaaccaggg atgcagggag aacctgggcc accagggcca   4140 cctggaaaacc taggaccctg tgggccaaga ggtaagccag gcaaggatgg aaaaccagga   4200
actcctggac cagctggaga aaaaggcaac aaaggttcta aaggagagcc aggaccagct   4260
ggatcagatg gattgccagg tttgaaagga aaacgtggag acagtggatc acctgcaacc   4320
tggacaacga gaggctttgt cttcacccga cacagtcaaa ccacagcaat tccttcatgt   4380
```

-continued

```
ccagagggga cagtgccact ctacagtggg ttttcttttc tttttgtaca aggaaatcaa      4440
cgagcccacg gacaagacct tggaactctt ggcagctgcc tgcagcgatt taccacaatg      4500
ccattcttat tctgcaatgt caatgatgta tgtaattttg catctcgaaa tgattattca      4560
tactggctgt caacaccagc tctgatgcca atgaacatgg ctcccattac tggcagagcc      4620
cttgagcctt atataagcag atgcactgtt tgtgaaggtc ctgcgatcgc catagccgtt      4680
cacagccaaa ccactgacat tcctccatgt cctcacggct ggatttctct ctggaaagga      4740
ttttcattca tcatgttcac aagtgcaggt tctgagggca ccgggcaagc actggcctcc      4800
cctggctcct gcctggaaga attccgagcc agcccatttc tagaatgtca tggaagagga      4860
acgtgcaact actattcaaa ttcctacagt ttctggctgg cttcattaaa cccagaaaga      4920
atgttcagaa agcctattcc atcaactgtg aaagctgggg aattagaaaa aataataagt      4980
cgctgtcagg tgtgcatgaa gaaaagacac tga                                    5013
```

<210> SEQ ID NO 5
<211> LENGTH: 5073
<212> TYPE: DNA
<213> ORGANISM: Artificial Sequence
<220> FEATURE:
<223> OTHER INFORMATION: exemplary COL4A4 transgene sequence

<400> SEQUENCE: 5

```
atgtggtctc tgcacatagt actaatgagg tgctccttca gattgaccaa gtccttggcc        60
acaggtccct ggtcacttat actcattctc ttttctgtac aatatgtata tgggagtgga       120
aagaaataca ttggtccttg tggaggaaga gattgctctg tttgccactg tgttcctgaa       180
aaggggtctc ggggtccacc aggaccacca gggccacagg gtccaattgg acccctggga       240
gccccaggac ccattgggct ttcaggagag aaaggaatga gaggggaccg cggccctcct       300
ggagcagcag gggacaaagg agataagggt ccaactggtg ttcctggatt ccaggtttta       360
gatggcatac ctgggcaccc agggcctcct ggacccagag caaacctgg tatgagtggc        420 cacaatggct caagaggtga cccagggttt ccaggaggaa gaggagctct tggcccagga       480
ggccccctag gccatcctgg ggaaaaggga gaaaaaggaa attcagtgtt cattttaggt       540
gccgttaaag gtattcaggg agacagaggg gacccaggac tgcctggctt accaggatct       600
tggggtgcag gaggaccggc aggtcccaca ggatatcctg gagagccagg gttagtggga       660
cctccgggcc aaccagggcg tccaggtttg aagggaaatc ccggtgtggg agtaaagggg       720
caaatgggag acccgggtga ggttggtcag caaggttctc ctggacccac cctgttggta       780
gagccacctg acttttgtct ctataaagga gaaaagggta taaaaggaat tcctggaatg       840
gttggactgc caggaccacc aggacgcaag ggagaatctg gtattggggc aaaaggagaa       900
aaaggtattc ctggatttcc agggcctcgg ggggatcctg gttcctatgg atctccaggt       960
tttccaggat taaagggaga actaggactg gttggagatc ctgggctatt tggattaatt      1020
ggcccaaagg gggatcctgg aaatcgaggg cacccaggac caccaggtgt tttggtgact      1080
ccacctcttc cactcaaagg cccaccaggg gacccagggt ccctggccg ctatggagaa       1140 acaggggatt ttgaccacc tggtcccca ggtctcttgg gcagaccagg gaagcctgt        1200 gcaggcatga taggaccccc tgggccacaa ggatttcctg gtcttcctgg gcttccagga      1260
gaagctggta ttcctgggag acctgattct gctccaggaa aaccagggaa gccaggatca      1320
cctggcttgc ctggagcacc aggcctgcag ggcctcccag gatcaagtgt gatatactgt      1380
agtgttggga accccggacc acaaggaata aaaggcaaag ttggtccccc aggaggaaga      1440
```

```
ggcccaaaag gagaaaaagg aaatgaagga ctctgtgcct gtgagcctgg acccatgggc       1500
ccccctggcc ctccaggact tcctgggagg caggggagta agggagactt ggggctccct       1560
ggctggcttg gaacaaaagg tgacccagga cctcctggtg ctgaaggacc tccagggcta       1620
ccaggaaagc atggtgcctc tggaccacct ggcaacaaag gggcgaaggg tgacatggtt       1680
gtatcaagag ttaaagggca caaaggagaa agaggtcctg atgggccccc aggatttcca       1740
gggcagccag gatcacatgg tcgggatgga catgctggag aaaaagggga tccaggacct       1800 ccagggatc atgaagatgc gaccccaggt ggtaaaggat ttcctggacc tctgggcccc        1860
ccaggcaaag caggacctgt gggggccccca ggactgggat ttcctggtcc accaggagag      1920
cgaggccacc caggagttcc aggccaccca ggtgtgaggg ccctgatgg cttgaagggt        1980 cagaaaggtg acacaatttc ttgcaacgta acctaccctg ggaggcatgg ccctccaggt       2040
tttgatggac ctccaggtcc gaagggattt ccaggtcccc aaggtgcccc tgggctgagt       2100
ggttcagatg ggcataaagg cagacctggc acaccaggaa cagcggaaat accaggtcca       2160
cctggttttc gtggtgacat gggagatccg ggttttggag gtgaaaaggg gtcctcccct       2220
gttgggcccc caggccctcc cggctcacca ggagtgaatg gtcagaaagg aatcccggga       2280
gaccctgcat ttggtcacct gggacccccg ggaaagaggg gtctttcagg agtgccaggg       2340
ataaaaggac ccagaggtga tccgggatgt ccagggctg aagggccagc tggcattcct        2400
ggattcctag gtctcaaagg tcccaaaggc agagagggac atgctgggtt tccaggtgtc       2460
ccaggtccac ctggccattc ctgtgaaaga ggtgctccag ggataccagg caaccgggga       2520
ctccctgggt atccaggtag cccaggtgct ccaggtggga aggacagcc gggagatgtg        2580 gggcctcccg ggccagctgg aatgaaaggc ctccccggac tcccaggacg gcctggggca       2640
catggtcccc caggcctccc aggaatccca ggtcccttttg gagatgatgg ctacctggt      2700 cctccaggtc caaagggacc ccgggggctg cctggtttcc caggttttcc cggagaaaga       2760
ggaaagcctg gtgcagaggg atgtcctggc gcaaagggag aacctggaga gaagggcatg       2820
tctggccttc ctggagaccg gggactgaga ggggccaaag gagccatagg acctcccgga       2880
gatgaaggag aaatggctat catttcacaa aagggaacac ctggggaacc tggacctcct       2940
ggagatgatg gattcccagg agaaagaggt gataaaggaa ctcccgggat gcaagggaga       3000
agaggagagc cggaagata cggaccacct ggatttcaca gaggggaacc tggtgagaaa        3060
ggtcagccag ggcctcctgg accccaggc cctccaggct caactggtct aagagggttc        3120
attggttttc caggacttcc aggtgaccag ggtgagccag gttctccagg tccccctgga       3180
ttttcaggaa ttgatggagc aagaggacct aaaggaaaca aggtgaccc tgccagtcac        3240 tttggtccac ctggtccaaa gggtgagcca ggtagccctg gatgtccagg gcattttgga       3300
gcatccggag agcagggctt gcctggtatt caagggccca gaggatcacc tggaaggcca       3360
gggccacctg gctcctctgg accaccaggg tgcccaggtg atcacgggat gcctgggctg       3420
aggggacagc caggagaaat gggagaccct gggccaagag gcctccaggg ggatccaggg       3480
ataccaggtc ctccgggaat aaaaggtccc tccggatcac ctggcctgaa cggcttgcat       3540
ggattgaaag tcagaaagg aactaaaggt gcttcaggtt tgcatgatgt ggggccacct        3600
ggtccagtgg gaatacctgg gctaaaaggg gagagaggag accctgggag cccaggaatc       3660
tctcctccag gtcctcgtgg aaagaaaggt ccccccaggac ccccagggga ttcaggacca      3720
cctggtcctg caggtgccac aggaagagct cctaaggaca ttcctgaccc gggtccacct       3780
```

```
ggagatcagg gacctcctgg tcctgatggc ccaagaggag cacctgggcc tccaggcctc   3840
cctgggagtg ttgaccttct gagaggggag ccaggtgact gtggtctacc agggccacca   3900
ggtccccctg gcccaccagg ccctccagga tacaaaggct ttccaggatg tgatggaaaa   3960
gatggccaga aaggaccagt gggattcccg ggaccgcagg gaccacatgg atttcctggg   4020
ccacctggag agaagggttt acctggacct ccagggagaa aagggcccac tggtcttccg   4080
ggtcccagag gtgaaccggg gccacctgca gatgtggatg actgtccccg aatcccaggc   4140
cttcctgggg cgccaggcat gagaggacca gaaggagcca tggggctccc tggaatgaga   4200
ggcccctcag gaccagggtg caaaggagag cctgggctgg atggcaggag gggtgtggat   4260
ggcgtccctg ggtctcctgg gcctcccgga cgtaaaggtg acacaggaga agacggctac   4320
cctggaggac cagggcctcc tggtcccatt ggggatcctg ggcccaaagg gtttggccct   4380
ggatacctcg gtggcttcct cctggttctc cacagtcaga cggaccagga gcccacctgc   4440
cccctgggca tgcccaggct ctggactggg tatagtctgt tatacctgga agggcaagag   4500
aaagctcaca atcaagacct tggtctggca gggtcttgcc ttcccgtatt tagcacgctg   4560 cccctttgcct actgcaacat ccaccaggtg tgccactatg cccagagaaa cgacagatcc   4620
tactggctgg ccagcgctgc gcccctcccc atgatgccac tctctgaaga ggcgatccgc   4680
ccctatgtca gccgctgtgc ggtatgcgag gccccggccc aggcggtggc ggtgcacagc   4740
caggaccagt ccatccccc atgtccgcag acctggagga gcctctggat cgggtattca   4800
ttcctgatgc acacaggagc tggggaccaa ggaggagggc aggcccttat gtcacctggc   4860
agctgcctgg aagatttcag agcagcacca ttccttgaat gccagggccg gcagggaact   4920
tgccactttt tcgcaaataa gtatagcttc tggctcacaa cggtgaaagc agacttgcag   4980
ttttcctctg ctccagcacc agacacctta aaagaaagcc aggcccaacg ccagaaaatc   5040
agccggtgcc aggtctgcgt gaagtatagc tag                                5073
```

```
<210> SEQ ID NO 6
<211> LENGTH: 5058
<212> TYPE: DNA
<213> ORGANISM: Artificial Sequence
<220> FEATURE:
<223> OTHER INFORMATION: exemplary COL4A5 transgene sequence

<400> SEQUENCE: 6
```

```
atgaaactgc gtggagtcag cctggctgcc ggcttgttct tactggccct gagtctttgg   60
gggcagcctg cagaggctgc ggcttgctat gggtgttctc caggatcaaa gtgtgactgc   120
agtggcataa aaggggaaaa gggagagaga gggtttccag gtttggaagg acacccagga   180
ttgcctggat ttccaggtcc agaagggcct ccggggcctc ggggacaaaa gggtgatgat   240
ggaattccag ggccaccagg accaaaagga atcagaggtc ctcctggact tcctggattt   300
ccagggacac caggtcttcc tggaatgcca ggccacgatg gggccccagg acctcaaggt   360
attcccggat gcaatggaac caagggagaa cgtggatttc aggcagtcc cggttttcct   420 ggtttacagg gtcctccagg accccctggg atcccaggta tgaagggtga accaggtagt   480
ataattatgt catcactgcc aggaccaaag ggtaatccag gatatccagg tcctcctgga   540
atacaaggcc tacctggtcc cactggtata ccagggccaa ttggtccccc aggaccacca   600
ggtttgatgg gccctcctgg tccaccagga cttccaggac ctaaggggaa tatgggctta   660
aatttccagg gacccaaagg tgaaaaaggt gagcaaggtc ttcagggccc acctgggcca   720
cctgggcaga tcagtgaaca gaaaagacca attgatgtag agtttcagaa aggagatcag   780
```

-continued

```
ggacttcctg gtgaccgagg gcctcctgga cctccaggga tacgtggtcc tccaggtccc      840
ccaggtggtg agaaaggtga gaagggtgag caaggagagc caggcaaaag aggtaaacca      900
ggcaaagatg gagaaaatgg ccaaccagga attcctggtt tgcctggtga tcctggttac      960
cctggtgaac ccggaaggga tggtgaaaag ggccaaaaag gtgacactgg cccacctgga     1020
cctcctggac ttgtaattcc tagacctggg actggtataa ctataggaga aaaaggaaac     1080
attgggttgc ctgggttgcc tggagaaaaa ggagagcgag gatttcctgg aatacagggt     1140
ccacctggcc ttcctggacc tccaggggct gcagttatgg gtcctcctgg ccctcctgga     1200
tttcctggag aaaggggtca gaaaggtgat gaaggaccac ctggaatttc cattcctgga     1260
cctcctggac ttgacggaca gcctggggct cctgggcttc cagggcctcc tggccctgct     1320
ggccctcaca ttcctcctag tgatgagata tgtgaaccag ccctccagg ccccccagga      1380 tctccaggtg ataaaggact ccaaggagaa caaggagtga aaggtgacaa aggtgacact     1440
tgcttcaact gcattggaac tggtatttca gggcctccag gtcaacctgg tttgccaggt     1500
ctcccaggtc ctccaggatc tcttggtttc cctggacaga aaggggaaaa aggacaagct     1560
ggtgcaactg gtcccaaagg attaccaggc attccaggag ctccaggtgc tccaggcttt     1620
cctggatcta aaggtgaacc tggtgatatc ctcacttttc caggaatgaa gggtgacaaa     1680
ggagagttgg gttccctgg agctccaggg cttcctggtt tacctggcac tcctggacag     1740
gatggattgc cagggcttcc tggcccgaaa ggagagcctg gtggaattac ttttaagggt     1800
gaaagaggtc cccctgggaa cccaggttta ccaggcctcc cagggaatat agggcctatg     1860 ggtcccctg gtttcggccc tccaggccca gtaggtgaaa aaggcataca aggtgtggca      1920
ggaaatccag gccagccagg aataccaggt cctaaagggg atccaggtca gactataacc     1980
cagccgggga gcctggctt gcctggtaac ccaggcagag atggtgatgt aggtcttcca       2040
ggtgaccctg gacttccagg gcaaccaggc ttgccaggga tacctggtag caaaggagaa     2100
ccaggtatcc ctggaattgg gcttcctgga ccacctggtc ccaaaggctt tcctggaatt     2160
ccaggacctc caggagcacc tgggacacct ggaagaattg gtctagaagg ccctcctggg     2220
ccacccggct ttccaggacc aaaagggtgaa ccaggatttg cattacctgg gccacctggg     2280
ccaccaggac ttccaggttt caaaggagca cttggtccaa aaggtgatcg tggtttccca      2340
ggacctccgg gtcctccagg acgcactggc ttagatgggc tccctggacc aaaaggtgat     2400
gttggaccaa atggacaacc tggaccaatg ggacctcctg ggctgccagg aatagtgtt      2460 cagggaccac caggaccacc agggattcct gggccaatag tcaacctgg tttacatgga       2520 ataccaggag agaaggggga tccaggacct cctggacttg atgttccagg accccagtt       2580 gaaagaggca gtcagggat ccccggagca cctggtccta taggacctcc aggatcacca       2640
gggcttccag aaaagcagg tgcctctgga tttccaggta ccaaaggtga atgggtatg        2700 atgggacctc caggcccacc aggaccttg ggaattcctg gcaggagtgg tgtacctggt       2760
cttaaaggtg atgatggctt gcagggtcag ccaggacttc ctggccctac aggagaaaaa     2820
ggtagtaaag gagagcctgg ccttccaggc cctcctggac caatggatcc aaatcttctg     2880
ggctcaaaag gagagaaggg ggaacctggc ttaccaggta tacctggagt ttcagggcca     2940
aaaggttatc agggtttgcc tggagaccca gggcaacctg gactgagtgg acaacctgga     3000
ttaccaggac caccaggtcc caaaggtaac cctggtctcc ctggacagcc aggtctatta     3060
ggacctcctg gacttaaagg aaccatcggt gatatgggtt ttccagggcc tcagggtgtg     3120
```

```
gaagggcctc ctggaccttc tggagttcct ggacaacctg gctccccagg attacctgga    3180
cagaaaggcg acaaaggtga tcctggtatt tcaagcattg gtcttccagg tcttcctggt    3240
ccaaagggtg agcctggtct gcctggatac ccagggaacc ctggtatcaa aggttctgtg    3300
ggagatcctg gtttgcccgg attaccagga acccctggag caaaaggaca accaggcctt    3360
cctggattcc caggaacccc aggccctcct ggaccaaaag gtattagtgg ccctcctggg    3420
aaccccggcc ttccaggaga acctggtcct gtaggtggtg gaggtcatcc tgggcaacca    3480
gggcctccag gcgaaaaagg caaacccggt caagatggta ttcctggacc agctggacag    3540
aagggtgaac caggtcaacc aggctttgga aacccaggac ccctggact tccaggactt     3600 tctggccaaa agggtgatgg aggattacct gggattccag gaaatcctgg ccttccaggt    3660
ccaaagggcg aaccaggctt tcacggtttc cctggtgtgc agggtccccc aggccctcct    3720
ggttctccgg gtccagctct ggaaggacct aaaggcaacc ctgggcccca aggtcctcct    3780
gggagaccag gtctaccagg tccagaaggt cctccaggtc tccctggaaa tggaggtatt    3840
aaaggagaga agggaaatcc aggccaacct gggctacctg gcttgcctgg tttgaaagga    3900
gatcaaggac caccaggact ccagggtaat cctggccggc cgggtctcaa tggaatgaaa    3960
ggagatcctg gtctccctgg tgttccagga ttcccaggca tgaaaggacc cagtggagta    4020
cctggatcag ctggccctga gggggaaccg ggacttattg gtcctccagg tcctcctgga    4080
ttacctggtc cttcaggaca gagtatcata attaaaggag atgctggtcc tccaggaatc    4140
cctggccagc ctgggctaaa gggtctacca ggaccccaag gacctcaagg cttaccaggt    4200
ccaactggcc ctccaggaga tcctggacgc aatggactcc ctggctttga tggtgcagga    4260
gggcgcaaag gagacccagg tctgccagga cagccaggta cccgtggttt ggatggtccc    4320
cctggtccag atggattgca aggtccccca ggtcccctg gaacctcctc tgttgcacat     4380
ggatttctta ttacacgcca cagccagaca acggatgcac cacaatgccc acaggaaca     4440 cttcaggtct atgaaggctt ttctctcctg tatgtacaag gaaataaaag agcccacggt    4500
caagacttgg ggacggctgg cagctgcctt cgtcgcttta gtaccatgcc tttcatgttc    4560
tgcaacatca ataatgtttg caactttgct tcaagaaatg actattctta ctggctctct    4620
accccagagc ccatgccaat gagcatgcaa cccctaaagg ccagagcat ccagccattc     4680 attagtcgat gtgcagtatg tgaagctcca gctgtggtga tcgcagttca cagtcagacg    4740
atccagattc cccattgtcc tcagggatgg gattctctgt ggattggtta ttccttcatg    4800
atgcatacaa gtgcaggggc agaaggctca ggtcaagccc tagcctcccc tggttcctgc    4860
ttggaagagt ttcgttcagc tcccttcatc gaatgtcatg ggaggggtac ctgtaactac    4920
tatgccaact cctacagctt ttggctggca actgtagatg tgtcagacat gttcagtaaa    4980
cctcagtcag aaacgctgaa agcaggagac ttgaggacac gaattagccg atgtcaagtg    5040
tgcatgaaga ggacataa                                                  5058
```

<210> SEQ ID NO 7
<211> LENGTH: 1192
<212> TYPE: DNA
<213> ORGANISM: Artificial Sequence
<220> FEATURE:
<223> OTHER INFORMATION: exemplary minimal NPHS1 promoter

<400> SEQUENCE: 7

```
cacctgaggt caggagttcg agaccagcgt ggccaacatg atgaaacccc gtctctagta      60
aaaatacaaa aattagccag gcatggtgct atatacctgt agcaccagct acttgggaga     120
```

-continued

```
cagaggtggg agaattactt gaacctggga ggttcaagcc atgggaggtg gaagttgcag      180
tgagccgaga tgccactgca ctccagcctg agcaacagag caagactatc tcaagaaaag      240
aaagaaagaa agaaagagac ttgccaaggt catgtatcag ggcaaggaag agctgggggc      300
ccagctggct gctccctgc tgagctggga gaccaccttg atctgacttc tcccatcttc       360
ccagcctaag ccaggccctg gggtcacgga ggctggggag gcaccgagga acgcgcctgg      420
catgtgctga cagggggattt tatgctccag ctgggccagc tgggaggagc ctgctgggca     480
gaggccagag ctggggggctc tggaaggtac ctgggggaggg ttgcactgtg agaatgagct    540
caagctgggt cagagagcag ggctgactct gccagtgcct gcatcagcct catcgctctc     600
ctaggctcct ggcctgctgg actctgggct gcaggtcctt cttgaaaggc tgtgagtagt     660
gagacaagga gcaggagtga ggggtggcag gagagaagat agagattgag agagagagag    720
agagagagac agagagagag gaagagacag agacaaaagg agagagaacg gcttagacaa     780
ggagagaaat atggaaagat aaagagactg ggcgcagtgg ctcacgcctg taatcccaac    840
acttggggag gccaaggtgg gaggatggct tgaaggaaag agtctgagat caacctggcc    900
aacatagtga gacccgtct ctaaaaaaaa aagaaaaaaa aaagaaaaaa gaaaaaaaag      960 ttttttaaa gagacagaga aagagactca gagattgaga ctgagagcaa gacagagaga    1020
gatactcaca gggaagaggg gaagaggaaa acgagaaagg gaggagagta acggaaagag    1080
ataaaaaaga aaagcaggtg gcagagacac acagagaggg acccagagaa agccagacag    1140
acgcaggtgg ctggcagcgg gcgctgtggg ggtcacagta gggggacctg tg             1192
```

<210> SEQ ID NO 8
<211> LENGTH: 1249
<212> TYPE: DNA
<213> ORGANISM: Artificial Sequence
<220> FEATURE:
<223> OTHER INFORMATION: exemplary minimal NPHS1 promoter

<400> SEQUENCE: 8

```
cctgcagggc ccactagtct gtaatcccag cattttggga ggctgaggca gatggatcac      60
ctgaggtcag gagttcgaga ccagcctggc caacatgatg aaaccccgtc tctagtaaaa      120
atacaaaaat tagccaggca tggtgctata tacctgtagt accagctact gggagacag      180 aggtgggaga attacttgaa cctgggaggt tcaagccatg ggaggtggaa gttgcagtga      240
gccgagatgc cactgcactc cagcctgagc aacagcaa gactatctca agaaaaaaaa       300
gaaagaaaga aaggggacttg ccaaggtcat gtatcagggc aaggaagagc tgggggccca     360
gctggctgct ccctgctga ctgggagac caccttgatc tgacttctcc catcttccca        420
gcctaagcca ggccctgggg tcacggaggc tggggaggca ccgaggaacg cgcctggcat      480
gtgctgacag ggaattttat gctccagctg gccagctgg gaggagcctg ctgggcagag      540
gccagagctg ggggctctgg aaggtacctg ggggaggttg cactgtgaga atgagctcaa     600
gctgggtcag agagcagggc tgactctgcc agtgcctgca tcagcctcat cgctctccta     660
ggctcctggc ctgctggact ctgggctgca ggtccttctt gaaaggctgt gagtagtgag     720
acaaggagca ggagtgaggg gtggcaggag agaagataga gattgagaga gagagagaga    780
gagacagaga gaggaagaga gacagagaca aaggagagag aacggcttta gacaaggaga    840
gaaagatgga aagataaaga gactgggcgc agtggctcac gcctgtaatc ccaacacttg    900
gggaggccaa ggtgggagga tggcttgaag gaaagagtct gagatcaacc tggccaacat    960
```

-continued

```
agtgagaccc cgtctctaaa aaaaaaaaag aaaaaaaaaa gaaaaaagaa aaaaaagttt      1020
ttttaaagag acagagaaag agactcagag attgagactg agagcaagac agagagagac      1080
actcacaggg aagaggggaa gaggaaaacg agaaagggag gagagtaacg gaaagagata      1140
aaaaagaaaa gcaggtggca gagacacaga gagagggacc cagagaaagc cagacagacg      1200
caggtggctg gcagcgggcg ctgtgggggt cacagtaggg ggacctgtc                  1249

<210> SEQ ID NO 9
<211> LENGTH: 819
<212> TYPE: DNA
<213> ORGANISM: Artificial Sequence
<220> FEATURE:
<223> OTHER INFORMATION: exemplary minimal nephrin promoter

<400> SEQUENCE: 9
ggccctgggg tcacggaggc tggggaggca ccgaggaacg cgcctggcat gtgctgacag        60
ggaattttat gctccagctg ggccagctgg gaggagcctg ctgggcagag gccagagctg       120
ggggctctgg aaggtacctg ggggaggttg cactgtgaga atgagctcaa gctgggtcag       180
agagcagggc tgactctgcc agtgcctgca tcagcctcat cgctctccta ggctcctggc       240
ctgctggact ctgggctgca ggtccttctt gaaaggctgt gagtagtgag acaaggagca       300
ggagtgaggg gtggcaggag agaagataga gattgagaga gagagagaga gagacagaga       360
gagaggaaga gacagagaca aaaggagaga gaacggctta gacaaggaga gaaagatgga       420
aagataaaga gactgggcgc agtggctcac gcctgtaatc ccaacacttg gggaggccaa       480
ggtgggagga tggcttgaag gaaagagtct gagatcaacc tggccaacat agtgagaccc       540
cgtctctaaa aaaaaaaag aaaaaaaaaa gaaaaaagaa aaaaaagttt ttttaaagag        600
acagagaaag agactcagag attgagactg agagcaagac agagagagac actcacaggg       660
aagaggggaa gaggaaaacg agaaagggag gagagtaacg gaaagagata aaaaagaaaa       720
gcaggtggca gagacacaga gagagggacc cagagaaagc cagacagacg caggtggctg       780
gcagcgggcg ctgtgggggt cacagtaggg ggacctgtc                             819

<210> SEQ ID NO 10
<211> LENGTH: 265
<212> TYPE: DNA
<213> ORGANISM: Artificial Sequence
<220> FEATURE:
<223> OTHER INFORMATION: exemplary minimal nephrin promoter

<400> SEQUENCE: 10
ggccctgggg tcacggaggc tggggaggca ccgaggaacg cgcctggcat gtgctgacag        60
ggaattttat gctccaggag caagacagag agagacactc acaggaagag ggggaagagg       120
aaaacgagaa agggaggaga gtaacggaaa gagataaaaa agaaaagcag gtggcagaga       180
cacagagaga gggacccaga gaaagccaga cagacgcagg tggctggcag cgggcgctgt       240
gggggtcaca gtaggggggac ctgtc                                           265

<210> SEQ ID NO 11
<211> LENGTH: 628
<212> TYPE: DNA
<213> ORGANISM: Artificial Sequence
<220> FEATURE:
<223> OTHER INFORMATION: exemplary minimal NPHS2 promoter

<400> SEQUENCE: 11
ggaaagttgg ggatgaggcg aaatttctga ttttacctta aagtgaccct aattcgatga        60
```

```
ccttttgtgg ttttttttctt ttttcttttt tcttttttac ttggccctgc ccaagcagga     120
cctaaaaaca aacagacaaa aaaggttact aacaactgtt cctctccacg aaaatctgca     180
gtaaaaggta aaagatgtat tcgtttgaa gagaaaccag agcttgcgat gagcttctgt       240
atctccgtca gccctctagc atgacattag gaaccctcca ggagatgagt cttcacagcc     300
cgggttggca cctgcagaca cgcactttc aacgcccgca ccctgcccgg ggccggctct       360
cccacccagg cctctctctg cttcagcgcc gccccggccg tgggagtcgg cgggcgcagt     420
ccacagctcc accaagacac agctgtcggg gttccgggtg cgccccgccc gcggccccgg     480
tgtcccgccc ctcgccctca gcccccaccc gacggtcttt agggtccccc gggcacgcca     540
cgcggacccg cagcgactcc acagggactg cgctcccgtg ccctagcgc tcccgcgctg      600 ctgctccagc cgcccggcag ctctgacc                                        628
```

```
<210> SEQ ID NO 12
<211> LENGTH: 77
<212> TYPE: DNA
<213> ORGANISM: Artificial Sequence
<220> FEATURE:
<223> OTHER INFORMATION: exemplary proximal promoter region

<400> SEQUENCE: 12
ggccctgggg tcacggaggc tggggaggca ccgaggaacg cgcctggcat gtgctgacag      60
ggaattttat gctccag                                                      77
```

```
<210> SEQ ID NO 13
<211> LENGTH: 77
<212> TYPE: DNA
<213> ORGANISM: Artificial Sequence
<220> FEATURE:
<223> OTHER INFORMATION: exemplary variant proximal promoter region

<400> SEQUENCE: 13
ggccctgggg tcacggaggc tggggaggca ccgaggaacg cgcctggcat gtgctgacag      60
gggattttat gctccag                                                      77
```

```
<210> SEQ ID NO 14
<211> LENGTH: 32
<212> TYPE: DNA
<213> ORGANISM: Artificial Sequence
<220> FEATURE:
<223> OTHER INFORMATION: exemplary core promoter region

<400> SEQUENCE: 14
gagcaagaca gagagagaca ctcacaggga ag                                     32
```

```
<210> SEQ ID NO 15
<211> LENGTH: 156
<212> TYPE: DNA
<213> ORGANISM: Artificial Sequence
<220> FEATURE:
<223> OTHER INFORMATION: exemplary 5'UTR

<400> SEQUENCE: 15
aggggaagag gaaaacgaga aagggaggag agtaacggaa agagataaaa aagaaaagca      60
ggtggcagag acacagagag agggacccag agaaagccag acagacgcag gtggctggca     120
gcgggcgctg tggggggtcac agtaggggga cctgtc                                156
```

```
<210> SEQ ID NO 16
```

```
<211> LENGTH: 188
<212> TYPE: DNA
<213> ORGANISM: Artificial Sequence
<220> FEATURE:
<223> OTHER INFORMATION: exemplary core promoter region and 5'UTR

<400> SEQUENCE: 16
gagcaagaca gagagagaca ctcacaggga agaggggaag aggaaaacga gaaagggagg      60
agagtaacgg aaagagataa aaaagaaaag caggtggcag agacacagag agagggaccc     120
agagaaagcc agacagacgc aggtggctgg cagcgggcgc tgtgggggtc acagtagggg     180
gacctgtc                                                              188

<210> SEQ ID NO 17
<211> LENGTH: 32
<212> TYPE: DNA
<213> ORGANISM: Artificial Sequence
<220> FEATURE:
<223> OTHER INFORMATION: exemplary variant core promoter region

<400> SEQUENCE: 17
gagcaagaca gagagagata ctcacaggga ag                                    32

<210> SEQ ID NO 18
<211> LENGTH: 156
<212> TYPE: DNA
<213> ORGANISM: Artificial Sequence
<220> FEATURE:
<223> OTHER INFORMATION: exemplary variant 5'UTR

<400> SEQUENCE: 18
aggggaagag gaaaacgaga aagggaggag agtaacggaa agagataaaa aagaaaagca      60
ggtggcagag acacacagag agggacccag agaaagccag acagacgcag gtggctggca     120
gcgggcgctg tggggggtcac agtaggggga cctgtg                              156

<210> SEQ ID NO 19
<211> LENGTH: 188
<212> TYPE: DNA
<213> ORGANISM: Artificial Sequence
<220> FEATURE:
<223> OTHER INFORMATION: exemplary variant core promoter region and
      5'UTR

<400> SEQUENCE: 19
gagcaagaca gagagagata ctcacaggga agaggggaag aggaaaacga gaaagggagg      60
agagtaacgg aaagagataa aaaagaaaag caggtggcag agacacacag agagggaccc     120
agagaaagcc agacagacgc aggtggctgg cagcgggcgc tgtgggggtc acagtagggg     180
gacctgtg                                                              188

<210> SEQ ID NO 20
<211> LENGTH: 554
<212> TYPE: DNA
<213> ORGANISM: Artificial Sequence
<220> FEATURE:
<223> OTHER INFORMATION: exemplary optional promoter region

<400> SEQUENCE: 20
ctgggccagc tgggaggagc ctgctgggca gaggccagag ctgggggctc tggaaggtac      60
ctgggggagg ttgcactgtg agaatgagct caagctgggt cagagagcag ggctgactct     120
gccagtgcct gcatcagcct catcgctctc ctaggctcct ggcctgctgg actctgggct     180
```

-continued

```
gcaggtcctt cttgaaaggc tgtgagtagt gagacaagga gcaggagtga ggggtggcag      240
gagagaagat agagattgag agagagagag agagagacag agagagagga agagacagag      300
acaaaaggag agagaacggc ttagacaagg agagaaagat ggaaagataa agagactggg      360
cgcagtggct cacgcctgta atcccaacac ttggggaggc caaggtggga ggatggcttg      420
aaggaaagag tctgagatca acctggccaa catagtgaga ccccgtctct aaaaaaaaaa      480
aagaaaaaaa aaagaaaaaa gaaaaaaaag ttttttttaaa gagacagaga aagagactca      540
gagattgaga ctga                                                        554
```

```
<210> SEQ ID NO 21
<211> LENGTH: 430
<212> TYPE: DNA
<213> ORGANISM: Artificial Sequence
<220> FEATURE:
<223> OTHER INFORMATION: exemplary optional upstream promoter region

<400> SEQUENCE: 21
cctgcagggc ccactagtct gtaatcccag cattttggga ggctgaggca gatggatcac       60
ctgaggtcag gagttcgaga ccagcctggc caacatgatg aaaccccgtc tctagtaaaa      120
atacaaaaat tagccaggca tggtgctata tacctgtagt accagctact tgggagacag      180
aggtgggaga attacttgaa cctgggaggt tcaagccatg ggaggtggaa gttgcagtga      240
gccgagatgc cactgcactc cagcctgagc aacagagcaa gactatctca agaaaaaaaa      300
gaaagaaaga aagggacttg ccaaggtcat gtatcagggc aaggaagagc tggggggccca      360 gctggctgct cccctgctga gctgggagac caccttgatc tgacttctcc catcttccca      420
gcctaagcca                                                             430
```

```
<210> SEQ ID NO 22
<211> LENGTH: 7
<212> TYPE: DNA
<213> ORGANISM: Artificial Sequence
<220> FEATURE:
<223> OTHER INFORMATION: exemplary RAR binding site

<400> SEQUENCE: 22 ggggtca                                                                  7
```

```
<210> SEQ ID NO 23
<211> LENGTH: 17
<212> TYPE: DNA
<213> ORGANISM: Artificial Sequence
<220> FEATURE:
<223> OTHER INFORMATION: exemplary WT1 binding site

<400> SEQUENCE: 23
cggaggctgg ggaggca                                                      17
```

```
<210> SEQ ID NO 24
<211> LENGTH: 5
<212> TYPE: DNA
<213> ORGANISM: Artificial Sequence
<220> FEATURE:
<223> OTHER INFORMATION: exemplary enhancer box

<400> SEQUENCE: 24 atgtg                                                                    5
```

```
<210> SEQ ID NO 25
<211> LENGTH: 30
```

<212> TYPE: DNA
<213> ORGANISM: Artificial Sequence
<220> FEATURE:
<223> OTHER INFORMATION: exemplary transcription factor binding region

<400> SEQUENCE: 25
gagcaagaca gagagagaca ctcacaggga                                               30

<210> SEQ ID NO 26
<211> LENGTH: 589
<212> TYPE: DNA
<213> ORGANISM: Artificial Sequence
<220> FEATURE:
<223> OTHER INFORMATION: exemplary Woodchuck hepatitis
      post-transcriptional regulatory element (WPRE)

<400> SEQUENCE: 26
aatcaacctc tggattacaa aatttgtgaa agattgactg gtattcttaa ctatgttgct      60
ccttttacgc tatgtggata cgctgcttta atgcctttgt atcatgctat tgcttcccgt      120
atggctttca ttttctcctc cttgtataaa tcctggttgc tgtctcttta tgaggagttg      180
tggcccgttg tcaggcaacg tggcgtggtg tgcactgtgt ttgctgacgc aaccccact       240 ggttggggca ttgccaccac ctgtcagctc ctttccggga ctttcgcttt ccccctccct      300
attgccacgg cggaactcat cgccgcctgc cttgcccgct gctggacagg ggctcggctg      360
ttgggcactg acaattccgt ggtgttgtcg gggaaatcat cgtcctttcc ttggctgctc      420
gcctgtgttg ccacctggat tctgcgcggg acgtccttct gctacgtccc ttcggccctc      480
aatccagcgg accttccttc ccgcggcctg ctgccggctc tgcggcctct tccgcgtctt      540
cgccttcgcc ctcagacgag tcggatctcc ctttgggccg cctccccgc                  589

<210> SEQ ID NO 27
<211> LENGTH: 13
<212> TYPE: RNA
<213> ORGANISM: Artificial Sequence
<220> FEATURE:
<223> OTHER INFORMATION: exemplary Kozak sequence

<400> SEQUENCE: 27
gccgccacca ugg                                                                 13

<210> SEQ ID NO 28
<211> LENGTH: 225
<212> TYPE: DNA
<213> ORGANISM: Artificial Sequence
<220> FEATURE:
<223> OTHER INFORMATION: exemplary bovine growth hormone (bGH)
      polyadenylation signal sequence

<400> SEQUENCE: 28
ctgtgccttc tagttgccag ccatctgttg tttgcccctc ccccgtgcct tccttgaccc      60
tggaaggtgc cactcccact gtcctttcct aataaaatga ggaaattgca tcgcattgtc      120
tgagtaggtg tcattctatt ctggggggtg gggtggggca ggacagcaag ggggaggatt      180
gggaagacaa tagcaggcat gctggggatg cggtgggctc tatgg                      225

<210> SEQ ID NO 29
<211> LENGTH: 17
<212> TYPE: DNA
<213> ORGANISM: Artificial Sequence
<220> FEATURE:
<223> OTHER INFORMATION: exemplary soluble neuropilin-1 polyadenylation
      signal

<400> SEQUENCE: 29
aaataaaata cgaaatg                                                    17

<210> SEQ ID NO 30
<211> LENGTH: 135
<212> TYPE: DNA
<213> ORGANISM: Artificial Sequence
<220> FEATURE:
<223> OTHER INFORMATION: exemplary SV40pA signal sequence

<400> SEQUENCE: 30
aacttgttta ttgcagctta taatggttac aaataaagca atagcatcac aaatttcaca     60
aataaagcat tttttttcact gcattctagt tgtggtttgt ccaaactcat caatgtatct    120
tatcatgtct ggatc                                                     135

<210> SEQ ID NO 31
<211> LENGTH: 736
<212> TYPE: PRT
<213> ORGANISM: Artificial Sequence
<220> FEATURE:
<223> OTHER INFORMATION: exemplary AAV9 VP1 capsid protein

<400> SEQUENCE: 31

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

```
Tyr Lys Gln Ile Ser Asn Ser Thr Ser Gly Gly Ser Ser Asn Asp Asn
            260             265             270

Ala Tyr Phe Gly Tyr Ser Thr Pro Trp Gly Tyr Phe Asp Phe Asn Arg
        275             280             285

Phe His Cys His Phe Ser Pro Arg Asp Trp Gln Arg Leu Ile Asn Asn
    290             295             300

Asn Trp Gly Phe Arg Pro Lys Arg Leu Asn Phe Lys Leu Phe Asn Ile
305             310             315             320

Gln Val Lys Glu Val Thr Asp Asn Asn Gly Val Lys Thr Ile Ala Asn
            325             330             335

Asn Leu Thr Ser Thr Val Gln Val Phe Thr Asp Ser Asp Tyr Gln Leu
            340             345             350

Pro Tyr Val Leu Gly Ser Ala His Glu Gly Cys Leu Pro Pro Phe Pro
            355             360             365

Ala Asp Val Phe Met Ile Pro Gln Tyr Gly Tyr Leu Thr Leu Asn Asp
    370             375             380

Gly Ser Gln Ala Val Gly Arg Ser Ser Phe Tyr Cys Leu Glu Tyr Phe
385             390             395             400

Pro Ser Gln Met Leu Arg Thr Gly Asn Asn Phe Gln Phe Ser Tyr Glu
            405             410             415

Phe Glu Asn Val Pro Phe His Ser Ser Tyr Ala His Ser Gln Ser Leu
            420             425             430

Asp Arg Leu Met Asn Pro Leu Ile Asp Gln Tyr Leu Tyr Tyr Leu Ser
            435             440             445

Lys Thr Ile Asn Gly Ser Gly Gln Asn Gln Gln Thr Leu Lys Phe Ser
    450             455             460

Val Ala Gly Pro Ser Asn Met Ala Val Gln Gly Arg Asn Tyr Ile Pro
465             470             475             480

Gly Pro Ser Tyr Arg Gln Gln Arg Val Ser Thr Thr Val Thr Gln Asn
            485             490             495

Asn Asn Ser Glu Phe Ala Trp Pro Gly Ala Ser Ser Trp Ala Leu Asn
            500             505             510

Gly Arg Asn Ser Leu Met Asn Pro Gly Pro Ala Met Ala Ser His Lys
            515             520             525

Glu Gly Glu Asp Arg Phe Phe Pro Leu Ser Gly Ser Leu Ile Phe Gly
    530             535             540

Lys Gln Gly Thr Gly Arg Asp Asn Val Asp Ala Asp Lys Val Met Ile
545             550             555             560

Thr Asn Glu Glu Glu Ile Lys Thr Thr Asn Pro Val Ala Thr Glu Ser
            565             570             575

Tyr Gly Gln Val Ala Thr Asn His Gln Ser Ala Gln Ala Gln Ala Gln
            580             585             590

Thr Gly Trp Val Gln Asn Gln Gly Ile Leu Pro Gly Met Val Trp Gln
            595             600             605

Asp Arg Asp Val Tyr Leu Gln Gly Pro Ile Trp Ala Lys Ile Pro His
        610             615             620

Thr Asp Gly Asn Phe His Pro Ser Pro Leu Met Gly Gly Phe Gly Met
625             630             635             640

Lys His Pro Pro Pro Gln Ile Leu Ile Lys Asn Thr Pro Val Pro Ala
            645             650             655

Asp Pro Pro Thr Ala Phe Asn Lys Asp Lys Leu Asn Ser Phe Ile Thr
            660             665             670

Gln Tyr Ser Thr Gly Gln Val Ser Val Glu Ile Glu Trp Glu Leu Gln
```

-continued

```
            675             680             685

Lys Glu Asn Ser Lys Arg Trp Asn Pro Glu Ile Gln Tyr Thr Ser Asn
    690             695             700

Tyr Tyr Lys Ser Asn Asn Val Glu Phe Ala Val Asn Thr Glu Gly Val
705             710             715             720

Tyr Ser Glu Pro Arg Pro Ile Gly Thr Arg Tyr Leu Thr Arg Asn Leu
            725             730             735

<210> SEQ ID NO 32
<211> LENGTH: 736
<212> TYPE: PRT
<213> ORGANISM: Artificial Sequence
<220> FEATURE:
<223> OTHER INFORMATION: exemplary LK03 VP1 capsid protein

<400> SEQUENCE: 32

Met Ala Ala Asp Gly Tyr Leu Pro Asp Trp Leu Glu Asp Asn Leu Ser
1               5              10              15

Glu Gly Ile Arg Glu Trp Trp Ala Leu Gln Pro Gly Ala Pro Lys Pro
            20              25              30

Lys Ala Asn Gln Gln His Gln Asp Asn Ala Arg Gly Leu Val Leu Pro
        35              40              45

Gly Tyr Lys Tyr Leu Gly Pro Gly Asn Gly Leu Asp Lys Gly Glu Pro
    50              55              60

Val Asn Ala Ala Asp Ala Ala Ala Leu Glu His Asp Lys Ala Tyr Asp
65              70              75              80

Gln Gln Leu Lys Ala Gly Asp Asn Pro Tyr Leu Lys Tyr Asn His Ala
            85              90              95

Asp Ala Glu Phe Gln Glu Arg Leu Lys Glu Asp Thr Ser Phe Gly Gly
            100             105             110

Asn Leu Gly Arg Ala Val Phe Gln Ala Lys Lys Arg Leu Leu Glu Pro
        115             120             125

Leu Gly Leu Val Glu Glu Ala Ala Lys Thr Ala Pro Gly Lys Lys Arg
    130             135             140

Pro Val Asp Gln Ser Pro Gln Glu Pro Asp Ser Ser Ser Gly Val Gly
145             150             155             160

Lys Ser Gly Lys Gln Pro Ala Arg Lys Arg Leu Asn Phe Gly Gln Thr
            165             170             175

Gly Asp Ser Glu Ser Val Pro Asp Pro Gln Pro Leu Gly Glu Pro Pro
            180             185             190

Ala Ala Pro Thr Ser Leu Gly Ser Asn Thr Met Ala Ser Gly Gly Gly
        195             200             205

Ala Pro Met Ala Asp Asn Asn Glu Gly Ala Asp Gly Val Gly Asn Ser
    210             215             220

Ser Gly Asn Trp His Cys Asp Ser Gln Trp Leu Gly Asp Arg Val Ile
225             230             235             240

Thr Thr Ser Thr Arg Thr Trp Ala Leu Pro Thr Tyr Asn Asn His Leu
            245             250             255

Tyr Lys Gln Ile Ser Ser Gln Ser Gly Ala Ser Asn Asp Asn His Tyr
            260             265             270

Phe Gly Tyr Ser Thr Pro Trp Gly Tyr Phe Asp Phe Asn Arg Phe His
        275             280             285

Cys His Phe Ser Pro Arg Asp Trp Gln Arg Leu Ile Asn Asn Asn Trp
    290             295             300

Gly Phe Arg Pro Lys Lys Leu Ser Phe Lys Leu Phe Asn Ile Gln Val
```

```
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Asn Arg Thr
                435                 440                 445

Gln Gly Thr Thr Ser Gly Thr Thr Asn Gln Ser Arg Leu Leu Phe Ser
        450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
                500                 505                 510

Gly Arg Asp Ser Leu Val Asn Pro Gly Pro Ala Met Ala Ser His Lys
                515                 520                 525

Asp Asp Glu Glu Lys Phe Phe Pro Met His Gly Asn Leu Ile Phe Gly
        530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
                580                 585                 590

Thr Arg Thr Val Asn Asp Gln Gly Ala Leu Pro Gly Met Val Trp Gln
                595                 600                 605

Asp Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
        690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Pro Leu
                725                 730                 735
```

```
<210> SEQ ID NO 33
<211> LENGTH: 735
<212> TYPE: PRT
<213> ORGANISM: Artificial Sequence
<220> FEATURE:
<223> OTHER INFORMATION: exemplary AAV3B VP1 capsid protein

<400> SEQUENCE: 33

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
                20                  25                  30

Lys Ala Asn Gln Gln His Gln Asp Asn Arg Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Ile Leu Glu Pro
            115                 120                 125

Leu Gly Leu Val Glu Glu Ala Ala Lys Thr Ala Pro Gly Lys Lys Arg
        130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Ala Pro Thr Ser Leu Gly Ser Asn Thr Met Ala Ser Gly Gly Gly
            195                 200                 205

Ala Pro Met Ala Asp Asn Asn Glu Gly Ala Asp Gly Val Gly Asn Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365
```

```
Val Phe Met Val Pro Gln Tyr Gly Tyr Leu Thr Leu Asn Asn Gly Ser
    370             375             380

Gln Ala Val Gly Arg Ser Ser Phe Tyr Cys Leu Glu Tyr Phe Pro Ser
385             390             395             400

Gln Met Leu Arg Thr Gly Asn Asn Phe Gln Phe Ser Tyr Thr Phe Glu
            405             410             415

Asp Val Pro Phe His Ser Ser Tyr Ala His Ser Gln Ser Leu Asp Arg
            420             425             430

Leu Met Asn Pro Leu Ile Asp Gln Tyr Leu Tyr Tyr Leu Asn Arg Thr
            435             440             445

Gln Gly Thr Thr Ser Gly Thr Thr Asn Gln Ser Arg Leu Leu Phe Ser
    450             455             460

Gln Ala Gly Pro Gln Ser Met Ser Leu Gln Ala Arg Asn Trp Leu Pro
465             470             475             480

Gly Pro Cys Tyr Arg Gln Gln Arg Leu Ser Lys Thr Ala Asn Asp Asn
            485             490             495

Asn Asn Ser Asn Phe Pro Trp Thr Ala Ala Ser Lys Tyr His Leu Asn
            500             505             510

Gly Arg Asp Ser Leu Val Asn Pro Gly Pro Ala Met Ala Ser His Lys
            515             520             525

Asp Asp Glu Glu Lys Phe Phe Pro Met His Gly Asn Leu Ile Phe Gly
    530             535             540

Lys Glu Gly Thr Thr Ala Ser Asn Ala Glu Leu Asp Asn Val Met Ile
545             550             555             560

Thr Asp Glu Glu Glu Ile Arg Thr Thr Asn Pro Val Ala Thr Glu Gln
            565             570             575

Tyr Gly Thr Val Ala Asn Asn Leu Gln Ser Ser Asn Thr Ala Pro Thr
            580             585             590

Thr Arg Thr Val Asn Asp Gln Gly Ala Leu Pro Gly Met Val Trp Gln
            595             600             605

Asp Arg Asp Val Tyr Leu Gln Gly Pro Ile Trp Ala Lys Ile Pro His
    610             615             620

Thr Asp Gly His Phe His Pro Ser Pro Leu Met Gly Gly Phe Gly Leu
625             630             635             640

Lys His Pro Pro Pro Gln Ile Met Ile Lys Asn Thr Pro Val Pro Ala
            645             650             655

Asn Pro Pro Thr Thr Phe Ser Pro Ala Lys Phe Ala Ser Phe Ile Thr
            660             665             670

Gln Tyr Ser Thr Gly Gln Val Ser Val Glu Ile Glu Trp Glu Leu Gln
            675             680             685

Lys Glu Asn Ser Lys Arg Trp Asn Pro Glu Ile Gln Tyr Thr Ser Asn
    690             695             700

Tyr Asn Lys Ser Val Asn Val Asp Phe Thr Val Asp Thr Asn Gly Val
705             710             715             720

Tyr Ser Glu Pro Arg Pro Ile Gly Thr Arg Tyr Leu Thr Arg Asn
            725             730             735
```

<210> SEQ ID NO 34
<211> LENGTH: 819
<212> TYPE: DNA
<213> ORGANISM: Artificial Sequence
<220> FEATURE:
<223> OTHER INFORMATION: exemplary minimal nephrin promoter variant

<400> SEQUENCE: 34

-continued

```
ggccctgggg tcacggaggc tggggaggca ccgaggaacg cgcctggcat gtgctgacag      60
gggattttat gctccagctg ggccagctgg gaggagcctg ctgggcagag gccagagctg     120
ggggctctgg aaggtacctg ggggaggttg cactgtgaga atgagctcaa gctgggtcag     180
agagcagggc tgactctgcc agtgcctgca tcagcctcat cgctctccta ggctcctggc     240
ctgctggact ctgggctgca ggtccttctt gaaaggctgt gagtagtgag acaaggagca     300
ggagtgaggg gtggcaggag agaagataga gattgagaga gagagagaga gagagacaga     360
gagagaggaa gagacagaga caaaaggaga gagaacggct tagacaagga gagaaagatg     420
gaaagataaa gagactgggc gcagtggctc acgcctgtaa tcccaacact tggggaggcc     480
aaggtgggag gatggcttga aggaaagagt ctgagatcaa cctggccaac atagtgagac     540
cccgtctcta aaaaaaaaag aaaaaaaaaa gaaaaaagaa aaaaagtttt ttttaaagag     600
acagagaaag agactcagag attgagactg agagcaagac agagagagat actcacaggg     660
aagaggggaa gaggaaaacg agaaagggag gagagtaacg gaaagagata aaaaagaaaa     720
gcaggtggca gagacacaca gagagggacc cagagaaagc cagacagacg caggtggctg     780
gcagcgggcg ctgtgggggt cacagtaggg ggacctgtg                            819
```

```
<210> SEQ ID NO 35
<211> LENGTH: 265
<212> TYPE: DNA
<213> ORGANISM: Artificial Sequence
<220> FEATURE:
<223> OTHER INFORMATION: exemplary minimal nephrin promoter variant

<400> SEQUENCE: 35
ggccctgggg tcacggaggc tggggaggca ccgaggaacg cgcctggcat gtgctgacag      60
gggattttat gctccaggag caagacagag agagatactc acagggaaga ggggaagagg     120
aaaacgagaa agggaggaga gtaacggaaa gagataaaaa agaaaagcag gtggcagaga     180
cacagagaga gggacccaga gaaagccaga cagacgcagg tggctggcag cgggcgctgt     240
gggggtcaca gtaggggggac ctgtc                                          265
```

```
<210> SEQ ID NO 36
<211> LENGTH: 6
<212> TYPE: DNA
<213> ORGANISM: Artificial Sequence
<220> FEATURE:
<223> OTHER INFORMATION: transcription factor binding region

<400> SEQUENCE: 36 tacgat                                                                 6
```

```
<210> SEQ ID NO 37
<211> LENGTH: 6
<212> TYPE: DNA
<213> ORGANISM: Artificial Sequence
<220> FEATURE:
<223> OTHER INFORMATION: transcription factor binding region

<400> SEQUENCE: 37 tataat                                                                 6
```

```
<210> SEQ ID NO 38
<211> LENGTH: 6
<212> TYPE: DNA
<213> ORGANISM: Artificial Sequence
<220> FEATURE:
```

-continued

```
<223> OTHER INFORMATION: transcription factor binding region

<400> SEQUENCE: 38 gatact                                                              6

<210> SEQ ID NO 39
<211> LENGTH: 6
<212> TYPE: DNA
<213> ORGANISM: Artificial Sequence
<220> FEATURE:
<223> OTHER INFORMATION: transcription factor binding region

<400> SEQUENCE: 39 tatgat                                                              6

<210> SEQ ID NO 40
<211> LENGTH: 6
<212> TYPE: DNA
<213> ORGANISM: Artificial Sequence
<220> FEATURE:
<223> OTHER INFORMATION: transcription factor binding region

<400> SEQUENCE: 40 tatgtt                                                              6

<210> SEQ ID NO 41
<211> LENGTH: 50
<212> TYPE: DNA
<213> ORGANISM: Artificial Sequence
<220> FEATURE:
<223> OTHER INFORMATION: exemplary chicken beta-globin polyadenylation
      signal

<400> SEQUENCE: 41
caataaaaga tctttatttt cattagatct gtgtgttggt tttttgtgtg            50
```